(12) United States Patent
Wagner et al.

(10) Patent No.: US 9,187,477 B2
(45) Date of Patent: Nov. 17, 2015

(54) AZABENZIMIDAZOLE DERIVATIVES

(71) Applicant: Boehringer Ingelheim International GmbH, Ingelheim am Rhein (DE)

(72) Inventors: Holger Wagner, Mettenberg (DE); Frank Himmelsbach, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/525,950

(22) Filed: Oct. 28, 2014

(65) Prior Publication Data
US 2015/0119393 A1 Apr. 30, 2015

(30) Foreign Application Priority Data

Oct. 31, 2013 (EP) .................... 13191195

(51) Int. Cl.
A61K 31/535 (2006.01)
C07D 491/02 (2006.01)
C07D 471/04 (2006.01)
A61K 31/437 (2006.01)
A61K 31/5377 (2006.01)
A61K 45/06 (2006.01)
C07D 493/04 (2006.01)

(52) U.S. Cl.
CPC ............ *C07D 471/04* (2013.01); *A61K 31/437* (2013.01); *A61K 31/5377* (2013.01); *A61K 45/06* (2013.01); *C07D 493/04* (2013.01)

(58) Field of Classification Search
None
See application file for complete search history.

(56) References Cited

FOREIGN PATENT DOCUMENTS

| CA | 2841906 A1 | 1/2013 |
| WO | 2012116145 A1 | 8/2012 |
| WO | 2013011932 A1 | 1/2013 |
| WO | 2014031465 A1 | 2/2014 |

OTHER PUBLICATIONS

International Search Report for PCT/EP2014/072959 mailed on Jan. 14, 2015.

*Primary Examiner* — Heidi Reese
(74) *Attorney, Agent, or Firm* — Michael P. Morris; Usha R. Patel

(57) ABSTRACT

The present invention relates to compounds of general formula I,

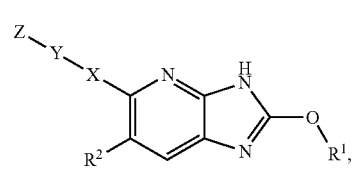

wherein the group $R^1$, $R^2$, X, Y and z are defined as in claim 1, which have valuable pharmacological properties, in particular bind to the AMP-activated protein kinase (AMPK) and modulate its activity. The compounds are suitable for treatment and prevention of diseases which can be influenced by this receptor, such as metabolic diseases, in particular diabetes type 2.

11 Claims, No Drawings

AZABENZIMIDAZOLE DERIVATIVES

FIELD OF THE INVENTION

The present invention relates to novel azabenzimidazole derivatives that are agonists of the AMP-activated protein kinase (AMPK), to processes for their preparation, to pharmaceutical compositions containing these compounds and to their medical use for the prophylaxis and/or treatment of diseases which can be influenced by the modulation of the function of AMPK. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common antidiabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

Sensing and regulating cellular the energy status in response to environmental and/or nutritional stress is highly important and AMP-activated protein kinase (AMPK) is a major contributor for this task (Hardie et al. (2001) Bioessays 23: 1112; Kemp et al. (2003) Biochem. Soc. Transactions 31: 162). Cellular energy depletion leads to the activation of AMP-activated protein kinase (AMPK) thereby inhibiting ATP consuming and upregulating ATP generating pathways. On a cellular level several substrates are regulated by AMP-activated protein kinase (AMPK) such as acetyl-CoA-carboxylase (ACC) and HMG-CoA-reductase (Carling et al. (1987) FEBS Letters 223: 217), hormone-sensitive lipase (Garton et al. (1989) Eur. J. Biochem. 179: 249), malonyl-CoA-decarboxylase (Saha et al. (2000) J. Biol. Chem. 275: 24279) and glycerol-3-phosphate acyltransferase (Muoio et al. (1999) Biochem. J. 338: 783).

AMP-activated protein kinase (AMPK) mediated phosphorylation of ACC leads to inhibition of ACC, which then results in a decrease of fatty acid synthesis while fatty acid oxidation is increased. AMP-activated protein kinase (AMPK) mediated phosphorylation and inhibition of HMG-CoA-reductase leads to a decrease in cholesterol synthesis. Triacylglycerol synthesis and fatty acid oxidation is regulated by AMP-activated protein kinase (AMPK) via glycerol-3-phosphate acyltransferase. In addition AMP-activated protein kinase (AMPK) stimulates glucose transport in skeletal muscle and regulates the expression of genes involved in fatty acid and glucose metabolism (Hardie et al. (2001) Bioessays 23: 1112; Kemp et al. (2003) Biochem. Soc. Transactions 31: 162). Glucose homeostasis is mediated in liver and muscle by AMP-activated protein kinase (AMPK), wherein activation of AMP-activated protein kinase (AMPK) leads to an increase in GLUT 4-dependent glucose uptake (Sakamoto et al. (2008) Am. J. Physiol. Endocrinol. Metab. 295: E29-E37; Karagounis et al. (2009) Int. J. Biochem. Cell Biol. 41: 2360-2363; Pehmøller et al. (2009) Am. J. Physiol. Endocrinol. Metab. 297: E665-E675).

Besides energy regulation on a cellular level AMP-activated protein kinase (AMPK) also regulates whole body energy metabolism. Independently of the cellular AMP level AMP-activated protein kinase (AMPK) can be activated by the adipocyte derived hormones leptin (Minokoski et al. (2002) Nature 415: 339) and adiponectin (Yamauchi et al. (2002) Nature Medicine 8: 1288).

From the points discussed above activation of AMP-activated protein kinase (AMPK) in vivo is expected to result in hepatic stimulation of fatty acid oxidation; inhibition of cholesterol synthesis, lipogenesis and triglyceride synthesis; stimulation of skeletal muscle fatty acid oxidation and glucose uptake; improved insulin action; increase in energy expenditure and hence a decrease body weight.

OBJECT OF THE PRESENT INVENTION

The object of the present invention is to provide new compounds, hereinafter described as compounds of formula I, in particular new azabenzimidazole derivatives, which are active with regard to the AMP-activated protein kinase (AMPK), notably are agonists of the AMP-activated protein kinase (AMPK).

A further object of the present invention is to provide new compounds, in particular new azabenzimidazole derivatives, which have an activating effect on the AMP-activated protein kinase (AMPK) in vitro and/or in vivo and possess suitable pharmacological and pharmacokinetic properties to use them as medicaments.

A further object of the present invention is to provide effective agonists of AMP-activated protein kinase (AMPK), in particular for the treatment of metabolic disorders, for example diabetes, dyslipidemia and/or obesity.

A further object of the present invention is to provide methods for treating a disease or condition mediated by the activation the AMP-activated protein kinase (AMPK) in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

AMP-activated protein kinase (AMPK) modulators are known in the art, for example, the compounds disclosed in WO 2012033149 and WO 2012116145. The azabenzimidazole derivatives of the present invention may provide several advantages, such as enhanced potency, high metabolic and/or chemical stability, high selectivity and/or tolerability and in consequence low toxicity, reduced risk to cause adverse events or undesirable side effects, and enhanced solubility.

SUMMARY OF THE INVENTION

In a first aspect the invention relates to compounds of formula I

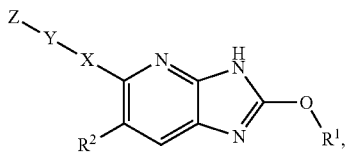

wherein
R$^1$ is selected from the group R$^1$-G1 consisting of C$_{3-10}$-cycloalkyl and heterocyclyl, both optionally substituted with 1 to 3 groups independently selected from HO—, NC—, HO$_2$C—, HO$_2$C—H$_2$C—, C$_{1-4}$-alkyl, C$_{1-4}$-alkyl-O—, and HO—C$_{1-4}$-alkyl-,
  wherein heterocyclyl denotes a saturated mono-, bi- or spirocyclic ring system having 5 to 10 ring member atoms of which 1 or 2 not vicinal ring members are O atoms;
R$^2$ is selected from the group R$^2$-G1 consisting of F, Cl, Br, C$_{1-4}$-alkyl, and C$_{1-4}$-alkyl-O—,
  wherein any alkyl group and subgroup is optionally substituted with 1 or more F atoms;
X is selected from the group X-G1 consisting of an arylene, and a heteroarylene group,
  wherein said arylene and heteroarylene groups are optionally substituted with 1 to 3 groups independently selected from F, Cl, Br, I, NC—, HO—, HO$_2$C—, C$_{1-4}$-alkyl, C$_{1-4}$-alkyl-O—, F$_3$C—, and F$_3$CO—;
Y is selected from the group Y-G1 consisting of a C$_{4-7}$-cycloalkylene, C$_{5-7}$-cycloalkenylene and heterocycloalkylene, wherein said cycloalkylene, cycloalkenylene and heterocycloalkylene groups are optionally substituted with 1 to 3 groups independently selected from F, NC—, C$_{1-4}$-alkyl and C$_{1-4}$-alkyl-O—;
and wherein heterocycloalkylene denotes a 5- to 12-membered bivalent saturated monocyclic or bicyclic fused, bridged or spiro group wherein one ring member is N or NR$^N$ and any other ring members are C atoms, preferably one ring member is N in the position linked to group X,
  wherein R$^N$ is selected from H, C$_{1-4}$-alkyl, C$_{3-7}$-cycloalkyl, C$_{3-7}$-cycloalkyl-CH$_2$—, heterocyclyl, and heterocyclyl-CH$_2$—,
  wherein any alkyl, cycloalkyl and heterocyclyl group or subgroup is optionally substituted with 1 to 3 groups independently selected from C$_{1-3}$-alkyl-O—, (C$_{1-3}$-alkyl)$_2$-N—, HO$_2$C—, C$_{1-3}$-alkyl-C(O)—, and C$_{1-3}$-alkyl-S(O)$_2$—,
Z is selected from the group Z-G1 consisting of (R$^N$R$^{N'}$)N—C(O)—O— and R$^O$O—C(O)—N(R$^{N''}$)—,
  wherein R$^N$ and R$^{N'}$ independently are selected from H, C$_{1-4}$-alkyl, C$_{3-7}$-cycloalkyl, C$_{3-7}$-cycloalkyl-CH$_2$—, heterocyclyl, and heterocyclyl-CH$_2$—, with the proviso that only one of R$^N$ and R$^{N'}$ denotes H,
  wherein any alkyl, cycloalkyl and heterocyclyl group or subgroup is optionally substituted with 1 to 3 groups independently selected from C$_{1-3}$-alkyl-O—, (C$_{1-3}$-alkyl)$_2$-N—, HO$_2$C—, C$_{1-3}$-alkyl-C(O)—, and C$_{1-3}$-alkyl-S(O)$_2$—, or
  wherein the group R$^N$(R$^{N'}$)N forms a heterocyclyl group linked via the N atom to the —C(O)—O— moiety,
  wherein said heterocyclyl group is optionally substituted with a group selected from F, H$_3$C— and CN,
  wherein R$^O$ is selected from C$_{2-4}$-alkyl, C$_{3-7}$-cycloalkyl, C$_{3-7}$-cycloalkyl-CH$_2$—, heterocyclyl, and heterocyclyl-CH$_2$—,
  wherein any alkyl, cycloalkyl and heterocyclyl group or subgroup is optionally substituted with 1 to 3 groups independently selected from C$_{1-3}$-alkyl-O—, (C$_{1-3}$-alkyl)$_2$N—, HO$_2$C—, C$_{1-3}$-alkyl-C(O)—, and C$_{1-3}$-alkyl-S(O)$_2$—, and
  wherein R$^{N''}$ is selected from H, H$_3$O—, H$_5$C$_2$—, and cyclopropyl;
wherein any heterocyclyl group mentioned hereinbefore, if not specified otherwise, denotes a saturated or partially unsaturated monocyclic or bicyclic fused, bridged or spiro group having 5 to 12 ring member atoms of which 4 to 11 ring members are C atoms and 1 to 3 ring members are heteroatoms selected from N and NR$^{N'''}$, or
1 or 2 ring members are heteroatoms selected from N and NR$^{N'''}$ and 1 ring member is selected from O and S(=O)$_r$ with r=0, 1 or 2, or
1 ring member is N and 2 ring members are independently selected from O and S(=O)$_r$ with r=0, 1 or 2, with the proviso that no O—O, S—S or S—O bond is formed,
  wherein 1 CH$_2$ ring member attached to a ring member N atom is optionally replaced by a —C(=O)— group,
  and wherein R$^{N'''}$ is selected from H, H$_3$C—, H$_5$C$_2$—, cyclopropyl, H$_3$C—C(O)—, and H$_3$C—S(O)$_2$—;
wherein any arylene group mentioned hereinbefore denotes a bivalent aryl group;
wherein any heteroarylene group mentioned hereinbefore denotes a bivalent heteroaryl group;
wherein any cycloalkylene group mentioned hereinbefore denotes a bivalent cycloalkyl group;
wherein any cycloalkenylene group mentioned hereinbefore denotes a bivalent cycloalkenyl group;

wherein any aryl group mentioned hereinbefore, if not specified otherwise, denotes a carbocyclic aromatic monocyclic group containing 6 carbon atoms which may be further fused to a second 5- or 6-membered carbocyclic group which may be aromatic, saturated or unsaturated;

wherein any heteroaryl group mentioned hereinbefore, if not specified otherwise, denotes
tetrazolyl,
a 5-membered heteroaromatic ring containing
1 ring member selected from $NR^{N'''}$, O and S, or
1 N and 1 ring member selected from $NR^{N'''}$, O and S, or
1 $NR^{N'''}$, O or S and 2 N,
wherein $R^{N'''}$ is defined as mentioned hereinbefore, or
a 6-membered heteroaromatic ring containing 1 to 3 N atoms; and
wherein in any definition mentioned hereinbefore and if not specified otherwise, any alkyl group or sub-group may be straight-chained or branched,
the isoforms, tautomers, stereoisomers, metabolites, prodrugs, solvates, hydrates, and the salts thereof, particularly the physiologically acceptable salts thereof with inorganic or organic acids or bases, or the combinations thereof.

The expression "optionally substituted with 1 or more F atoms" means that none or one up to successively all H atoms bound to carbon atoms of the respective group or submoiety may be replaced by F atoms, preferably 1 to 5 H atoms or, more preferred, 1 to 3 H atoms may be replaced by F atoms.

The extension -Gn used within the definitions is meant to identify genus n of the respective substituent. For example, $R^1$-G1 defines genus 1 of the substituent $R^1$.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the AMP-activated protein kinase (AMPK) in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the AMP-activated protein kinase (AMPK) in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the AMP-activated protein kinase (AMPK).

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^2$, X, Y and Z are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

According to one embodiment the group $R^1$ is selected from the group $R^1$-G2 consisting of

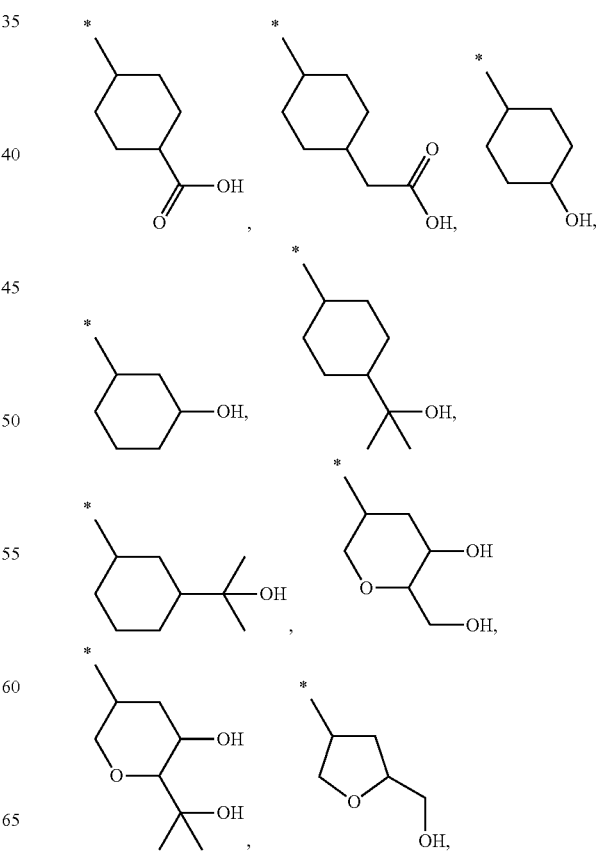

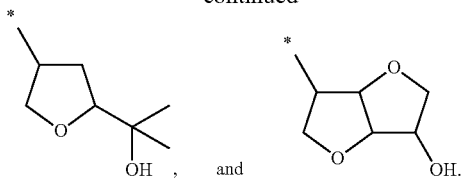

R¹-G3:

According to one embodiment the group $R^1$ is selected from the group R¹-G3 consisting of

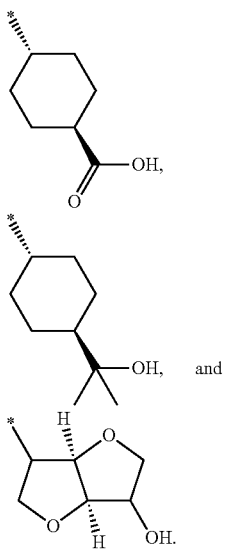

R¹-G4:

According to embodiment R¹-G4 the group $R^1$ is

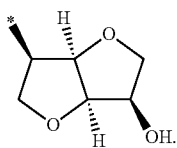 [SMILES: *[C@@H]1CO[C@H]2[C@@H]1OC[C@H]2O]

R²:

R²-G1:

The group $R^2$ is preferably selected from the group R²-G1 as defined hereinbefore.

R²-G2:

In another embodiment the group $R^2$ is selected from the group R²-G2 consisting of F, Cl, $H_3C-$.

R²-G3:

In another embodiment the group $R^2$ is Cl.

X:

X-G1:

The group X is preferably selected from the group X-G1 as defined hereinbefore.

X-G2:

In another embodiment the group X is selected from the group X-G2 consisting of a phenylene, pyridinylene, pyrimidinylene, and pyridazinylene group, wherein said phenylene, pyridinylene, pyrimidinylene, and pyridazinylene groups are optionally substituted with F, Cl, Br, NC—, $HO_2C-$, $H_3C-$, $H_3C-O-$, $F_3C-$, or $F_3CO-$.

X-G3:

In another embodiment the group X is selected from the group X-G3 consisting of a phenylene, and a pyridinylene group, bound via para positions and optionally substituted with F or $H_3C-$.

X-G4:

In another embodiment the group X is selected from the group X-G4 consisting of a phenylene group bound via para positions.

Y:

Y-G1:

The group Y is preferably selected from the group Y-G1 as defined hereinbefore.

Y-G2:

In another embodiment the group Y is selected from the group Y-G2 consisting of cyclobutylene, cyclopentylene, cyclohexylene, cyclohexenylene, azetidinylene, pyrrolidinylene, piperidinylene,

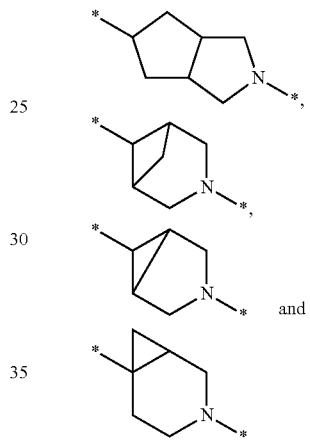

wherein any group containing an N atom as ring member is linked via the N-atom to group X, and wherein said cyclobutylene, cyclopentylene, cyclohexylene, cyclohexenylene, azetidinylene, pyrrolidinylene, and piperidinylene groups are optionally substituted with $H_3C-$.

Y-G3:

In another embodiment the group Y is selected from the group Y-G3 consisting of cyclobutylene, cyclopentylene, cyclohexylene,

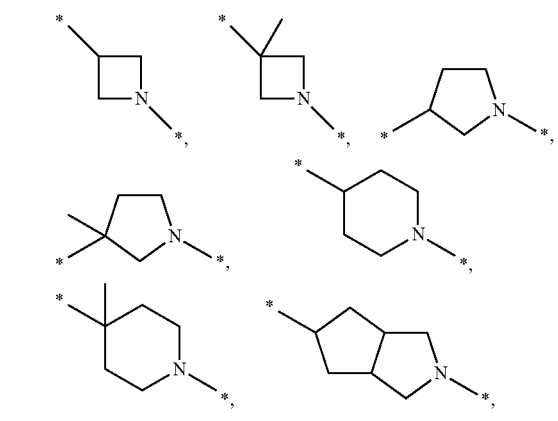

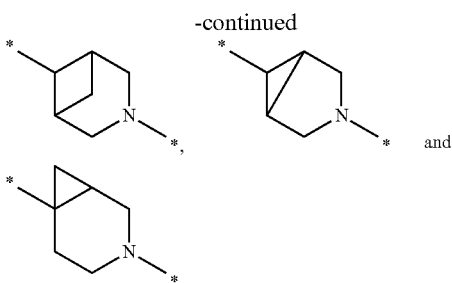

wherein any group containing an N atom as ring member is linked via the N-atom to group X.

Y-G4:
According to embodiment Y-G4 the group Y is

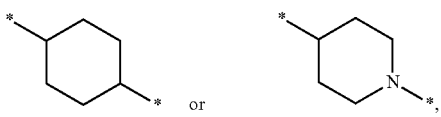

linked via the N-atom to group X.

Z:
Z-G1:
The group Z is preferably selected from the group Z-G1 as defined hereinbefore.

Z-G1a:
According to embodiment Z-G1a the group Z is $(R^N R^{N'})N-C(O)-O-$, wherein $R^N$ and $R^{N'}$ are defined as mentioned under Z-G1.

Z-G1b:
According to embodiment Z-G1b the group Z is $R^O O-C(O)-N(R^{N''})-$, wherein $R^O$ and $R^{N''}$ are defined as mentioned under Z-G1.

Z-G2a:
According to embodiment Z-G2a the group Z is $(R^N R^{N'})N-C(O)-O-$,
wherein $R^N$ and $R^{N'}$ independently are selected from H, $C_{1-4}$-alkyl, $C_{3-6}$-cycloalkyl, tetrahydrofuranyl, tetrahydrofuranyl-$CH_2-$, tetrahydropyranyl, tetrahydropyranyl-$CH_2-$, pyrrolidinyl, pyrrolidinyl-$CH_2-$, piperidinyl, and piperidinyl-$CH_2-$, with the proviso that only one of $R^N$ and $R^{N'}$ denotes H,
wherein any $C_{1-4}$-alkyl, $C_{3-6}$-cycloalkyl, tetrahydrofuranyl, tetrahydrofuranyl-$CH_2-$, tetrahydropyranyl, tetrahydropyranyl-$CH_2-$, pyrrolidinyl, pyrrolidinyl-$CH_2-$, piperidinyl, and piperidinyl-$CH_2$-group is optionally substituted with $H_3C-O-$, $(H_3C)_2N-$, $HO_2C-$, $H_3C-C(O)-$, or $H_3C-S(O)_2-$, or
wherein the group $R^N(R^{N'})N$ forms a azetidinyl-, pyrrolidinyl-, piperidinyl-, morpholinyl-, thiomorpholinyl-, or S,S-dioxomorpholinyl-group,
wherein said azetidinyl-, pyrrolidinyl-, or piperidinyl-groups are optionally substituted with $H_3C-$, $H_5C_2-$, cyclopropyl, $H_3C-C(O)-$, or $H_3C-S(O)_2-$.

Z-G2b:
According to embodiment Z-G2b the group Z is $R^O O-C(O)-N(R^{N''})-$,
wherein $R^O$ is selected from $C_{2-4}$-alkyl, $C_{3-6}$-cycloalkyl, tetrahydrofuranyl, tetrahydrofuranyl-$CH_2-$, tetrahydropyranyl, tetrahydropyranyl-$CH_2-$, pyrrolidinyl, pyrrolidinyl-$CH_2-$, piperidinyl, and piperidinyl-$CH_2-$,
wherein any $C_{2-4}$-alkyl, $C_{3-6}$-cycloalkyl, tetrahydrofuranyl, tetrahydrofuranyl-$CH_2-$, tetrahydropyranyl, tetrahydropyranyl-$CH_2-$, pyrrolidinyl, pyrrolidinyl-$CH_2-$, piperidinyl, and piperidinyl-$CH_2$-group is optionally substituted with $H_3C-O-$, $(H_3C)_2N-$, $HO_2C-$, $H_3C-C(O)-$, or $H_3C-S(O)_2-$, and
wherein $R^{N''}$ is selected from H, $H_3C-$, $H_5C_2-$, and cyclopropyl.

Z-G3a:
According to embodiment Z-G3a the group Z is $(R^N R^{N'})N-C(O)-O-$,
wherein $R^N$ and $R^{N'}$ independently are selected from H, $H_3C-$, $H_5C_2-$, $H_3C-(CH_2)_2-$, $(H_3C)_2CH-$, $H_3C-(CH_2)_3-$, $(H_3C)_2CH-CH_2-$, $(H_3C)_3C-$, $H_3CO-(CH_2)_2-$, $(H_3C)_2N-(CH_2)_2-$, cyclopropyl, cyclobutyl, cyclopentyl, cyclohexyl, tetrahydrofuranyl, tetrahydropyranyl, pyrrolidinyl, and piperidinyl, with the proviso that only one of $R^N$ and $R^{N'}$ denotes H
wherein any cyclobutyl, cyclopentyl and cyclohexyl group is optionally substituted with 1 or 2 groups independently selected from $H_3C-$, $H_3C-O-$, and $(H_3C)_2N-$, and
wherein any pyrrolidinyl and piperidinyl group is optionally substituted with $H_3C-$, $H_3C-C(O)-$, or $H_3C-S(O)_2-$, or
wherein the group $R^N(R^{N'})N$ forms an azetidinyl-, pyrrolidinyl-, or piperidinyl-, morpholinyl-group,
wherein said azetidinyl-, pyrrolidinyl-, or piperidinyl-groups are optionally substituted with $H_3C-$, $H_5C_2-$, cyclopropyl, $H_3C-C(O)-$, or $H_3C-S(O)_2-$.

Z-G3b:
According to embodiment Z-G3b the group Z is $R^O O-C(O)-N(R^{N''})-$,
wherein $R^O$ is selected from $H_5C_2-$, $H_3C-(CH_2)_2-$, $(H_3C)_2CH-$, $H_3C-(CH_2)_3-$, $(H_3C)_2CH-CH_2-$, $(H_3C)_3C-$, $H_3CO-(CH_2)_2-$, $(H_3C)_2N-(CH_2)_2-$, cyclopropyl, cyclobutyl, cyclopentyl, cyclohexyl, tetrahydrofuranyl, tetrahydropyranyl, pyrrolidinyl, and piperidinyl,
wherein any cyclobutyl, cyclopentyl and cyclohexyl group is optionally substituted with 1 or 2 groups independently selected from $H_3C-$, $H_3C-O-$, and $(H_3C)_2N-$, and
wherein any pyrrolidinyl and piperidinyl group is optionally substituted with $H_3C-$, $H_3C-C(O)-$, or $H_3C-S(O)_2-$, and
wherein $R^{N''}$ is selected from H, and $H_3C-$.

Z-G4a:
According to embodiment Z-G4a the group Z is $(R^N R^{N'})N-C(O)-O-$,
wherein $R^N$ and $R^{N'}$ independently are selected from H, $H_3C-$, $H_5C_2-$, $(H_3C)_2CH-$, cyclopentyl, cyclohexyl,

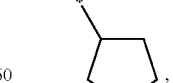

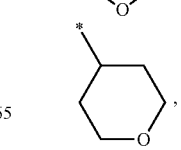

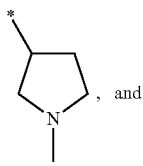, and

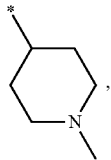, with the proviso that only one of $R^N$ and $R^{N'}$ denotes H, or wherein the group $R^N(R^{N'})$N altogether is selected from

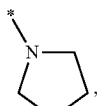,

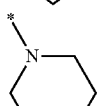,

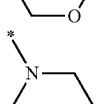, and

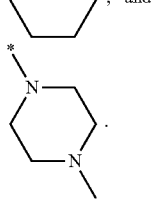.

Z-G4b:

According to embodiment Z-G4b the group Z is $R^OO$—C(O)—N(H)—,
wherein $R^O$ is selected from $H_5C_2$—, $(H_3C)_2CH$—, cyclopentyl, cyclohexyl,

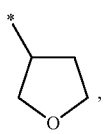,

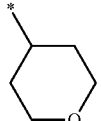,

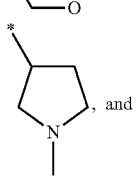, and

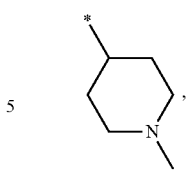,

Z-G5a:

According to embodiment Z-G5a the group Z is $(R^NR^{N'})$N—C(O)—O—,
wherein $R^N$ and $R^{N'}$ independently are selected from H, $H_3C$—, $H_5C_2$— and $(H_3C)_2CH$—,
with the proviso that only one of $R^N$ and $R^{N'}$ denotes H, or
wherein the group $R^N(R^{N'})$N altogether is selected from

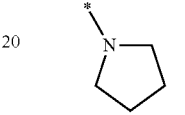 and 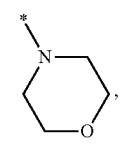,

Z-G5b:

According to embodiment Z-G5b the group Z is $R^OO$—C(O)—N(H)—,
wherein $R^O$ is selected from $H_5C_2$—, $(H_3C)_2CH$—, cyclopentyl and

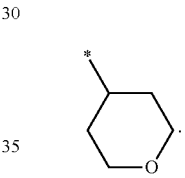.

Examples of preferred subgeneric embodiments (E) according to the present invention are set forth in the following table, wherein each substituent group of each embodiment is defined according to the definitions set forth hereinbefore and wherein all other substituents of the formula I are defined according to the definitions set forth hereinbefore:

TABLE 1

| Embodiment | $R^1$- | $R^2$- | X- | Y- | Z- |
|---|---|---|---|---|---|
| E-1 | $R^1$-G1 | $R^2$-G1 | X-G1 | Y-G1 | Z-G1a |
| E-2 | $R^1$-G2 | $R^2$-G1 | X-G1 | Y-G2 | Z-G1a |
| E-3 | $R^1$-G2 | $R^2$-G1 | X-G2 | Y-G1 | Z-G2a |
| E-4 | $R^1$-G3 | $R^2$-G2 | X-G1 | Y-G2 | Z-G3a |
| E-5 | $R^1$-G3 | $R^2$-G2 | X-G2 | Y-G2 | Z-G3a |
| E-6 | $R^1$-G3 | $R^2$-G2 | X-G2 | Y-G2 | Z-G4a |
| E-7 | $R^1$-G3 | $R^2$-G2 | X-G3 | Y-G3 | Z-G5a |
| E-8 | $R^1$-G3 | $R^2$-G3 | X-G3 | Y-G3 | Z-G5a |
| E-9 | $R^1$-G4 | $R^2$-G3 | X-G3 | Y-G4 | Z-G4a |
| E-10 | $R^1$-G4 | $R^2$-G3 | X-G4 | Y-G4 | Z-G5a |
| E-11 | $R^1$-G1 | $R^2$-G1 | X-G1 | Y-G1 | Z-G1b |
| E-12 | $R^1$-G2 | $R^2$-G1 | X-G1 | Y-G2 | Z-G1b |
| E-13 | $R^1$-G2 | $R^2$-G1 | X-G2 | Y-G1 | Z-G2b |
| E-14 | $R^1$-G3 | $R^2$-G2 | X-G1 | Y-G2 | Z-G3b |
| E-15 | $R^1$-G3 | $R^2$-G2 | X-G2 | Y-G2 | Z-G3b |
| E-16 | $R^1$-G3 | $R^2$-G2 | X-G2 | Y-G2 | Z-G4b |
| E-17 | $R^1$-G3 | $R^2$-G2 | X-G3 | Y-G3 | Z-G5b |
| E-18 | $R^1$-G3 | $R^2$-G3 | X-G3 | Y-G3 | Z-G5b |
| E-19 | $R^1$-G4 | $R^2$-G3 | X-G3 | Y-G4 | Z-G4b |
| E-20 | $R^1$-G4 | $R^2$-G3 | X-G4 | Y-G4 | Z-G5b |

According to embodiment E-8 those compounds of formula I are preferred, wherein

R¹ is selected from the group consisting of

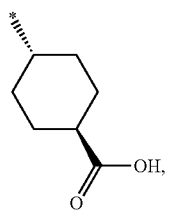

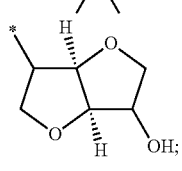 and

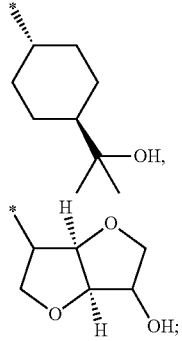

R² is Cl;
X is selected from the group consisting of a phenylene, and a pyridinylene group, bound via para positions and optionally substituted with F or H₃C—;
Y is selected from the group consisting of cyclobutylene, cyclopentylene, cyclohexylene,

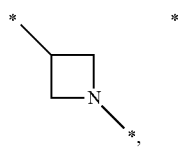 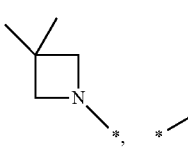 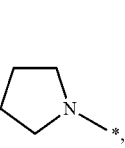

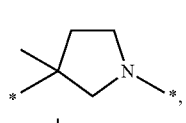 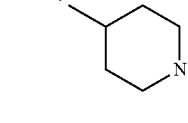

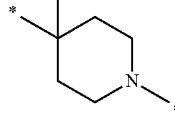 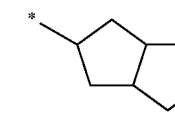

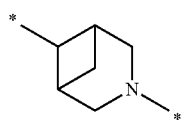 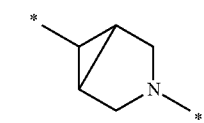 and

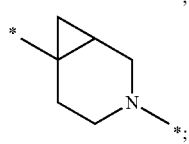

wherein any group containing an N atom as ring member is linked via the N-atom to group X,
Z is (R^N R^N')N—C(O)—O—,
wherein R^N and R^N' independently are selected from H, H₃C—, H₅C₂— and (H₃C)₂CH—,
with the proviso that only one of R^N and R^N' denotes H, or wherein the group R^N(R^N')N altogether is selected from

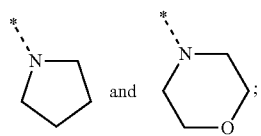

and the pharmaceutically acceptable salts thereof.

According to embodiment E-18 those compounds of formula I are preferred, wherein R¹ is selected from the group consisting of

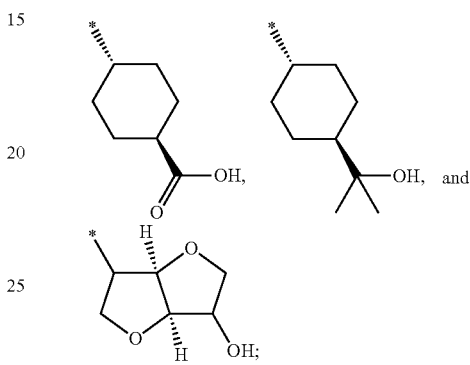

R² is Cl;
X is selected from the group consisting of a phenylene, and a pyridinylene group, bound via para positions and optionally substituted with F or H₃C—;
Y is selected from the group consisting of cyclobutylene, cyclopentylene, cyclohexylene,

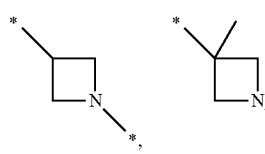 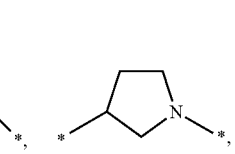

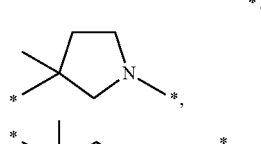 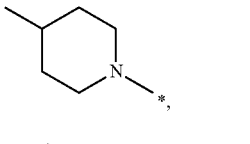

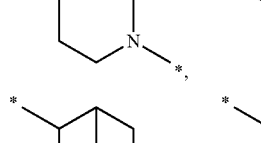 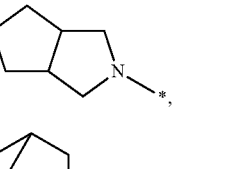

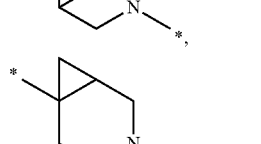 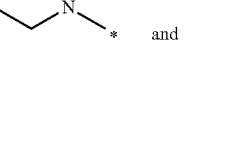 and wherein any group containing an N atom as ring member is linked via the N-atom to group X, Z is $R^O$—O—C(O)—N(H)—,
wherein $R^O$ is selected from $H_5C_2$—, $(H_3C)_2CH$—, cyclopentyl and

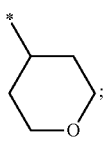

and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of the invention I are preferably accessed from a precursor 1 that bears the protected imidazopyridine-nitrogen (Scheme 1); $R^1$, $R^2$, X, Y and Z have the meaning as defined hereinbefore and hereinafter. The benzyl protecting group is cleaved advantageously using hydrogen in the presence of a transition metal, preferably palladium on carbon in a solvent such as methanol, ethanol, tetrahydrofurane, 1,4-dioxane. Benzyl groups bearing electron donating groups on the phenyl ring, such as methoxy, may also be removed under acidic conditions such as $H_2SO_4$, $CF_3CO_2H$, $MeSO_3H$. Amino-acetal derivatives can be cleaved under acidic conditions such as HCl, $H_2SO_4$, $CF_3CO_2H$, $MeSO_3H$, $KHSO_4$, $HCO_2H$, $BF_3xOEt_2$ in a solvent such as dichloromethane, water, tetrahydrofurane, 1,4-dioxane or mixtures thereof at −10 to 100° C. In addition to cleavage under acidic conditions, amino-acetal derivatives bearing a $Si(CH_3)_3$ group can also be cleaved in the presence of tetrabutylammonium fluoride.

Scheme 1

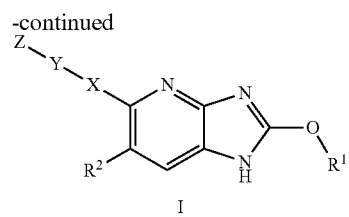

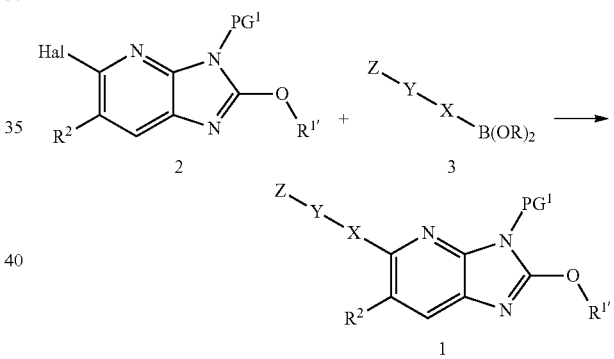

$PG^1=CH_2$-phenyl, wherein phenyl is optionally substituted with one or two $OCH_3$ groups;
$CH_2$—O—$C_{1-3}$-alkyl, wherein alkyl is optionally substituted with $Si(CH_3)_3$
$R^{1'}=R^1$ or $R^1$—$PG^2$ Carboxylic acid groups or hydroxy groups within $R^1$ might be protected with a suitable protecting group $PG^2$, e.g. a methyl- or ethyl group for carboxylic acids or a $tBu(CH_3)_2Si$-group for alcohols giving $R^{1'}$. The protecting group $PG^2$ is either removed together with $PG^1$ in one reaction step or in an additional deprotection step, depending on the nature of $PG^1$ and $PG^2$.

Compounds 1 can be prepared from imidazopyridine derivatives 2 and boronic acid derivatives 3 (Scheme 2); $R^2$, X, Y and Z have the meaning defined hereinbefore and hereinafter.

Scheme 2

Hal=Cl, Br, I
$B(OR)_2=B(OH)_2$,

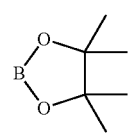

$R^{1'}$ and $PG^1$=as defined in Scheme 1

The reaction is preferably conducted with a palladium derived catalyst, e.g. [1,1'-bis(diphenylphosphino)-ferrocene]-dichloropalladium(II)-$CH_2Cl_2$-complex ($PdCl_2$ (dppf)$xCH_2Cl_2$) in the presence of a base, e.g. sodium carbonate, in a mixture of water and tetrahydrofurane, 1,4-dioxane or N,N-dimethylformamide at 40 to 120° C.

Compounds 1' bearing a carbamate linked via the oxygen to Y can be prepared from alcohols 4 (Scheme 3); $R^2$, X, Y, $R^N$ and $R^{N'}$ have the meaning as defined hereinbefore and hereinafter.

Scheme 3

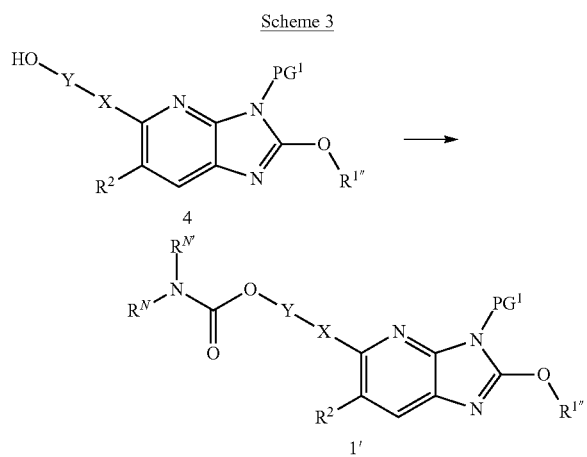

PG¹=as defined in Scheme 1
R¹''=R¹—PG²

In this reaction alcohols 4 are reacted with aminocarbamoylchlorides (($R^N R^{N'}$)NC(O)Cl) or isocyanates ($R^N$N=C=O) in the presence of a base, e.g. triethylamine, pyridine, sodium hydride, and optionally in the presence of a catalyst like 4-dimethylamino-pyridine (DMAP), in a solvent, e.g. dichloromethane, tetrahydrofurane, 1,4-dioxane, N,N-dimethylformamide, pyridine, at 0-140° C.

Compounds 1'' bearing a carbamate linked via the nitrogen to Y can be prepared from amines 5 (Scheme 4); $R^2$, X, Y, $R^O$ and $R^{N''}$ have the meaning as defined hereinbefore and hereinafter.

Scheme 4

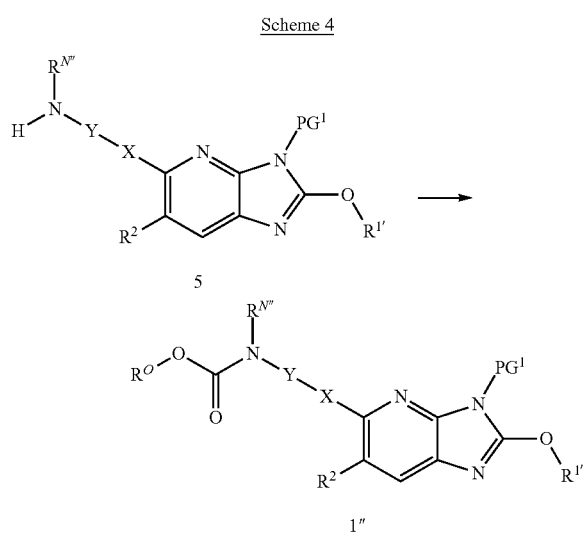

R¹' and PG¹=as defined in Scheme 1

In this reaction amines 5 are reacted with chloroformiates ($R^O$OC(O)Cl) in the presence of a base, e.g. triethylamine, pyridine, and optionally in the presence of a catalyst like 4-dimethylamino-pyridine (DMAP), in a solvent, e.g. dichloromethane, tetrahydrofurane, 1,4-dioxane, N,N-dimethylformamide, pyridine, at 0-140° C. Alternatively this transformation is achieved by reacting the amine with phosgene, diphosgene or triphosgene in a solvent like dichloromethane, tetrahydrofurane, or toluene at 0-100° C. to form the isocyanate and further treatment with a alcohol at 20-100° C. for formation of the carbamate.

The preparation of compounds 4' is shown in Scheme 5; $R^2$, X and Y have the meaning as defined hereinbefore and hereinafter.

Scheme 5

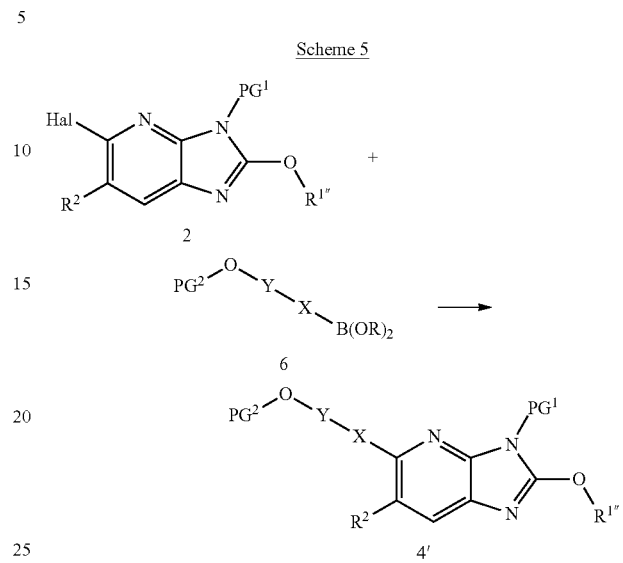

Hal=Cl, Br, I
B(OR)₂ and PG¹=as defined in Scheme 1
R¹''=R¹—PG²
PG²=H, protecting group Reaction of imidazopyridine derivatives 2 with boronic acid derivatives 6 gives compounds 4', wherein PG² denotes H or a suitable protecting group. The reaction is preferably conducted with a palladium derived catalyst, e.g. [1,1'-bis(diphenylphosphino)-ferrocene]-dichloropalladium(II)-CH₂Cl₂-complex (PdCl₂(dppf)xCH₂Cl₂), in the presence of a base, e.g. sodium carbonate, in a mixture of water and tetrahydrofurane, 1,4-dioxane or N,N-dimethylformamide at 40-120° C. In the case that PG² denotes a protecting group, cleavage of the protecting group by procedures well known to the one skilled in the art and described in the literature of organic synthesis gives compounds 4', wherein PG² denotes H.

The preparation of compounds 5' is shown in Scheme 6; $R^2$, X, Y and $R^{N''}$ have the meaning as defined hereinbefore and hereinafter.

Scheme 6

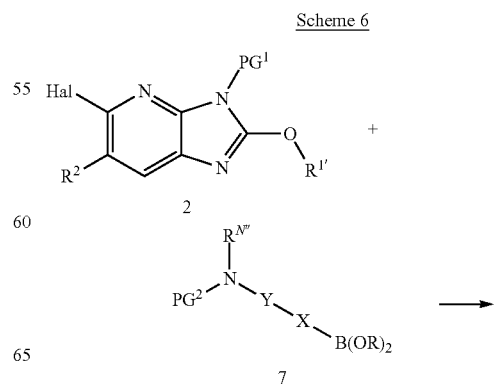

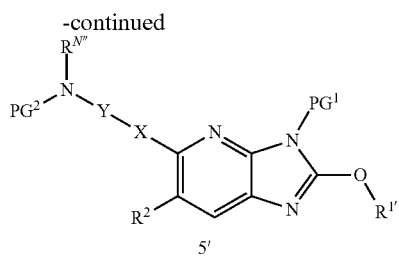

Hal=Cl, Br, I
R¹' and PG¹=as defined in Scheme 1
PG³=H, protecting group

Reaction of imidazopyridine derivatives 2 with boronic acid derivatives 7 gives compounds 5', wherein PG³ denotes H or a suitable protecting group. The reaction is preferably conducted with a palladium derived catalyst, e.g. [1,1'-bis(diphenylphosphino)-ferrocene]-dichloropalladium(II)-CH$_2$Cl$_2$-complex (PdCl$_2$(dppf)xCH$_2$Cl$_2$), in the presence of a base, e.g. sodium carbonate, in a mixture of water and tetrahydrofurane, 1,4-dioxane or N,N-dimethylformamide at 40-120° C. In the case that PG³ denotes a protecting group, cleavage of the protecting group by procedures well known to the one skilled in the art and described in the literature of organic synthesis gives compounds 5', wherein PG² denotes H.

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the AMP-activated protein kinase (AMPK) with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii)

prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

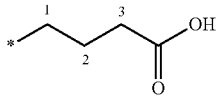

wherein the carboxy group is attached to the third carbon atom of the propyl group. The terms "1-methylpropyl-", "2,2-dimethylpropyl-" or "cyclopropylmethyl-" group represent the following groups:

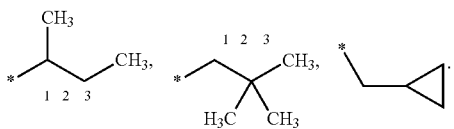

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-4}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, and $H_3C$—$C(CH_3)_2$—.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spiro-cyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "heterocyclyl", unless specified otherwise, means a saturated or unsaturated mono-, bi-, tri- or spirocarbocyclic, preferably mono-, bi- or spirocyclic-ring system containing one or more heteroatoms selected from N, O or $S(O)_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or $S(O)_r$ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

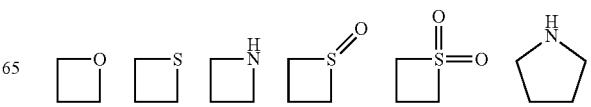

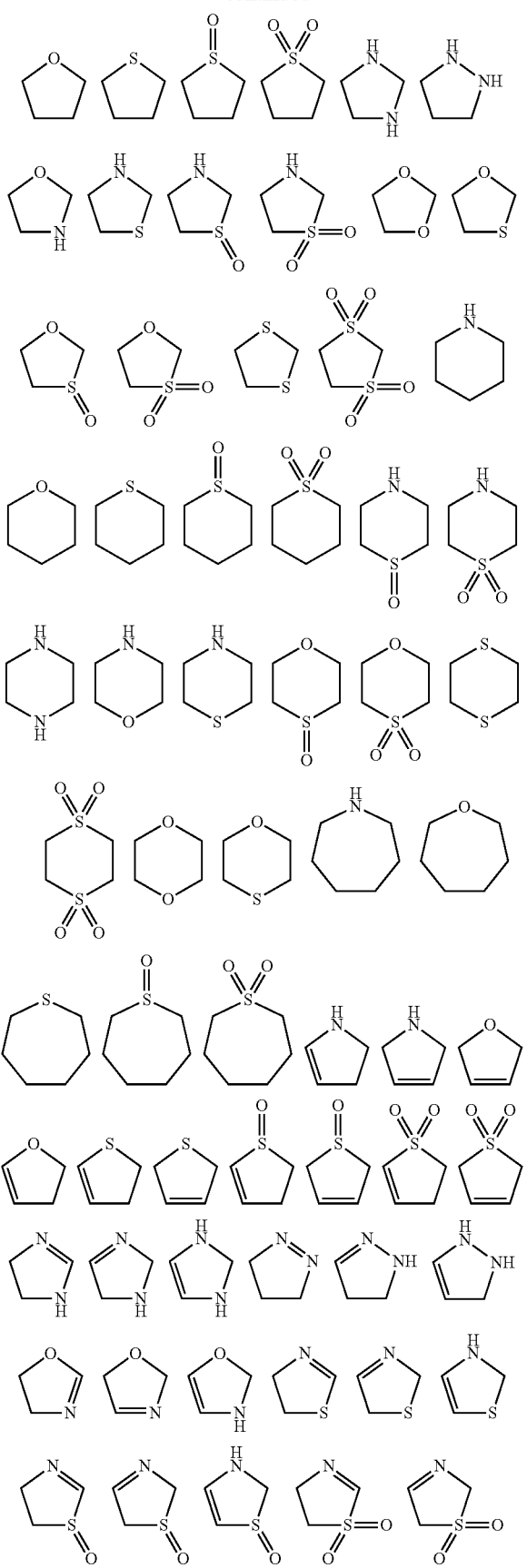
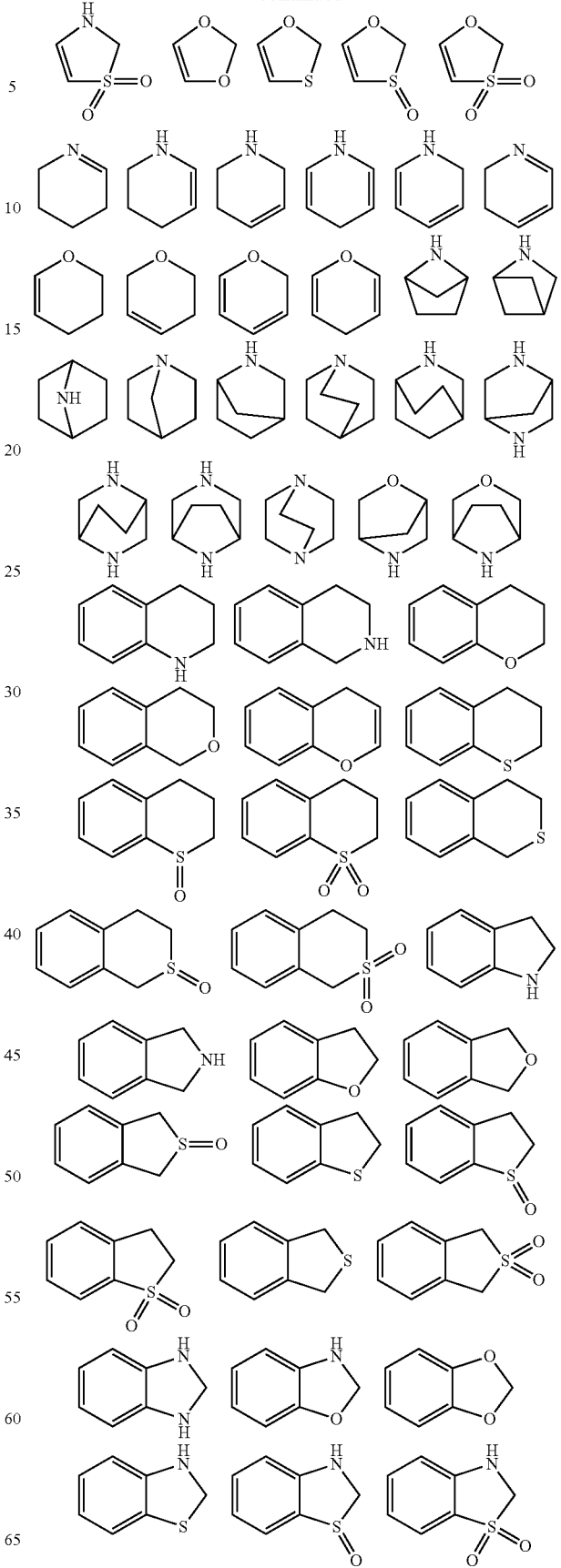

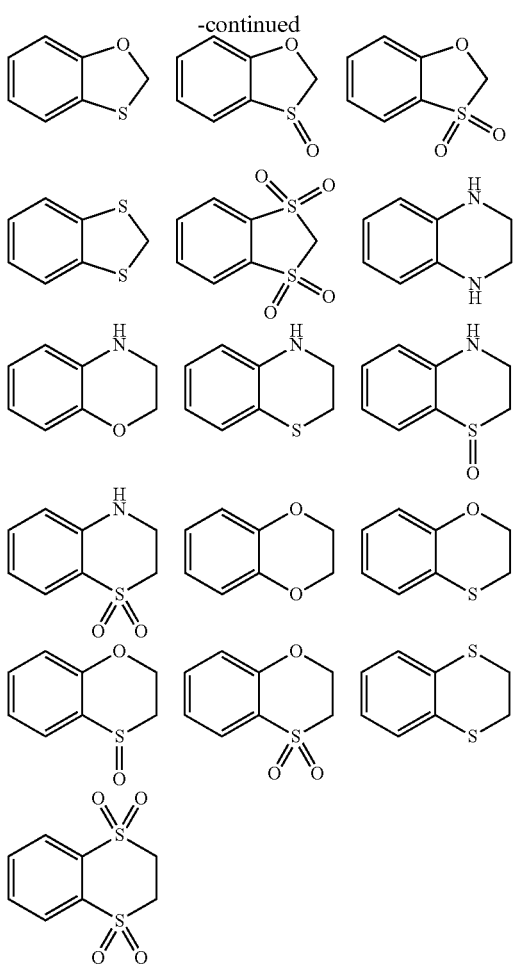

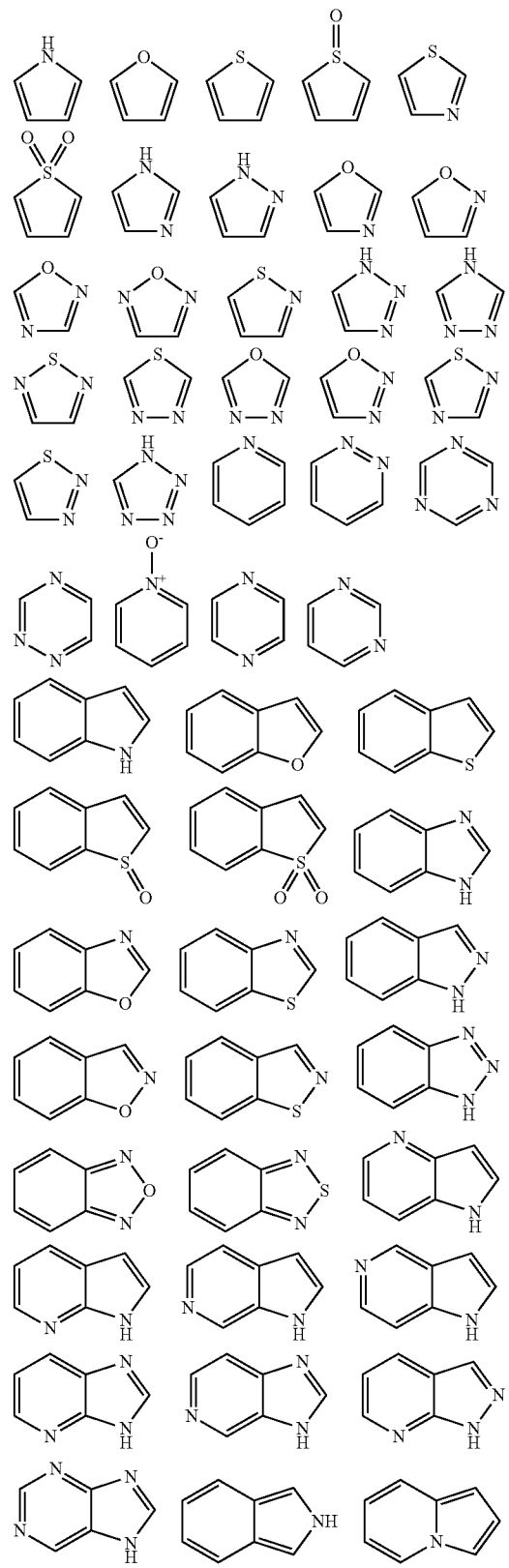

The term "aryl" as used herein, either alone or in combination with another radical, unless specified otherwise, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heteroaryl" or heteroaromatic group, unless specified otherwise, means a mono- or polycyclic, preferably mono- or bicyclic-ring system containing one or more heteroatoms selected from N, NH, NR$^N$, O or S(O)$_r$ with r=0, 1 or 2 wherein at least one of the heteroatoms is part of an aromatic ring, R$^N$ preferably is a C$_{1-3}$-alkyl group, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, NH, NR$^N$, O or S(O)$_r$ with r=0, 1 or 2 wherein at least one of the heteroatoms is part of an aromatic ring, R$^N$ preferably is a methyl group, and wherein said ring system may have a carbonyl group. The term "heteroaryl" is intended to include all the possible isomeric forms.

Thus, the term "heteroaryl" or heteroaromatic group includes the following exemplary structures which are not depicted as radicals as each form may be attached through a covalent bond to any atom so long as appropriate valences are maintained:

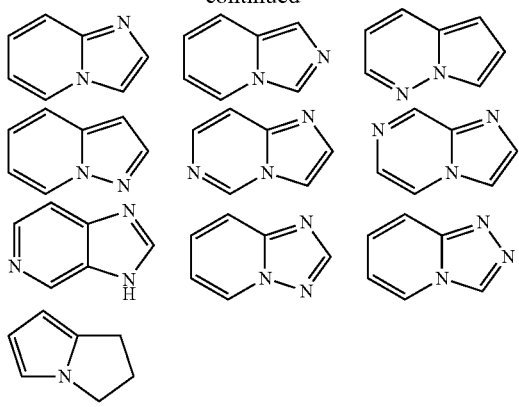

Many of the terms given above may be used repeatedly in the definition of a formula or group and in each case have one of the meanings given above, independently of one another.

Metabolic Stability

The metabolic degradation of the test compound is assayed at 37° C. with pooled human liver microsomes. The final incubation volume of 100 µl per time point contains TRIS buffer pH 7.6 at room temperature (0.1 M), magnesium chloride (5 mM), microsomal protein (1 mg/ml) and the test compound at a final concentration of 1 µM.

Following a short preincubation period at 37° C., the reactions were initiated by addition of beta-nicotinamide adenine dinucleotide phosphate, reduced form (NADPH, 1 mM) and terminated by transferring an aliquot into solvent after different time points.

Additionally, the NADPH-independent degradation was monitored in incubations without NADPH, terminated at 2 hour time point. The [%] remaining test compound after NADPH independent incubation is reflected by the parameter c (control) (metabolic stability). A c (control) (metabolic stability) value around 100% excludes cofactor independent activities (e.g. from esterases).

The quenched incubations are pelleted by centrifugation (10000 g, 5 min).

An aliquot of the supernatant is assayed by LC-MS/MS for the amount of parent compound. The half-life ($t_{1/2}$ INVITRO) is determined by the slope of the semilogarithmic plot of the concentration-time profile.

TABLE 2

| Example | $t_{1/2}$ INVITRO [Minutes] | c (control) (metabolic stability) [%] after 2 hours |
| --- | --- | --- |
| 1 | >130 | 100 |
| 2 | 111 | 109 |
| 3 | 19 | 117 |
| 4 | >130 | 103 |
| 5 | 68 | 106 |
| 6 | >130 | 98 |
| 8 | >130 | 102 |
| 9 | >130 | 100 |
| 10 | >130 | 105 |
| 11 | 110 | 106 |

Pharmacological Activity

The activity of the compounds of the invention may be demonstrated using the following in vitro AMPK activation assay:

Activated AMPK complex 1 (containing alpha1beta1gamma1) was obtained from baculovirus expression system. The gene encoding AMPK alpha1 was cloned into the pACG2T vector (BD Biosciences) to obtain a N-terminal Glutathion S transferase (GST)-fusion protein. The genes encoding AMPK beta1 and gamma1 were cloned into the p2Bac dual multiple cloning site vector (Invitrogen) with beta1 under the control of the p10 promoter and gamma1 under the control of the PH promoter. The transfer vectors containing AMPK were co-transfected individually with AcPNV BacMagic-3 DNA (EMD Millipore) in Sf9 cells and the recombinant baculoviruses were harvested after 5 days, followed by 3 rounds of amplification of the virus stock in Sf9 cells. AMPK (alpha1beta1gamma1) was expressed in High Five 5 cells by co-infection of recombinant alpha1 virus and recombinant beta1/gamma1 virus for 72 h at 27° C. Cells were harvested by centrifugation and lysed by 3 freeze/thaw cycles in PBS with 10% glycerol and protease inhibitor cocktail (Roche). After centrifugation AMPK a1b1g1 in the supernatant was captured by immobilized glutathione (GE Healthcare), impurities were washed away with PBS and AMPK alpha1beta1gamma1 was eluted with PBS containing 20 mM reduced gluthathione. The protein buffer was then exchanged to PBS with 10% glycerol and protein concentration was determined by UV absorbance.

The white 384-well Optiplates (cat. no. 6007299) were purchased from PerkinElmer. The V9101 ADP-Glo Kinase Assay and ultra pure ATP (V915A) was purchased from Promega. The substrate for AMPK (NH2-HMRSAMS-GLHLVKRR_CONH2) was purchased from Upstate (12-355).

All other materials were of highest grade commercially available.

Compounds were tested in either serial dilutions or single dose concentrations. The serial compound dilutions were prepared in 100% DMSO automatically. The final DMSO concentration in the assay was 0.1%.

The Compound Stock Solutions were 10 mM in 100% DMSO. The compounds were solubilised at room temperature.

In the 384-well plates 1.25 ul of test compound in assay buffer was mixed with 1.25 ul of AMPK and 1.25 µl of the peptide (final concentration of 1 µM) and 1.25 µl of ATP (final concentration of 30 µM), both dissolved in assay buffer. This step was followed by an incubation time of 60 min. Then 5 µl of ADP Glo Reagent was added. This was followed by 40 min of incubation. Then 10 µl of Kinase Detection Reagent was admixed. The plates were sealed and after an incubation period of 30 min, the luminescence signal was measured in an Envision reader. All incubation steps were accomplished at room temperature.

Assay buffer:

20 mM HEPES pH 7.0, 0.025% BSA, 15 mM $MgCl_2$, 0.01% Brij

Each assay microtiter plate contained wells with vehicle controls instead of compound (0.1% DMSO in water) as reference for the low signal (100% CTL, low signal), and wells with serial dilutions of AMP (final 30 µM) as reference for high signals.

The luminescence signal generated was proportional to the ADP concentration produced and was correlated with AMPK activity. The analysis of the data was performed by the calculation of the percentage of ATP consumption of AMPK in the presence of the test compound compared to the consumption of ATP in the presence of AMPK without compound.

(RLU(sample)/RLU(low control))*100[RLU=relative luminescence units]

An activator of the AMPK enzyme gave values above 100% CTL.

EC50 values based on dose response curves are calculated with the XlFIT software using the 4 Parameter Logistic Model or Sigmoidal Dose-Response Model.

The compounds according to the invention typically have $EC_{50}$ values in the range from about 0.1 nM to about 10 μM, preferably less than 1 μM, more preferably less than 100 nM.

$EC_{50}$ values for compounds according to the invention are shown in the following table. The number of the compound corresponds to the number of the Example in the experimental section.

TABLE 3

| Example | $EC_{50}$ [nM] |
|---------|----------------|
| 1 | 1.2 |
| 2 | 32 |
| 3 | 108 |
| 4 | 12 |
| 5 | 119 |
| 6 | 6 |
| 7 | 468 |
| 8 | 339 |
| 9 | 17 |
| 10 | 26 |
| 11 | 35 |
| 12 | 1311 |
| 13 | 2043 |
| 14 | 578 |
| 15 | 133 |
| 16 | 290 |

In view of their ability to modulate the activity of the AMP-activated protein kinase (AMPK), in particular an agonistic activity, the compounds of general formula I according to the invention, including the corresponding salts thereof, are theoretically suitable for the treatment of all those diseases or conditions which may be affected or which are mediated by the activation of the AMP-activated protein kinase (AMPK).

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the AMP-activated protein kinase (AMPK) in a patient, preferably in a human.

In yet another aspect the present invention relates to a method for treating a disease or condition mediated by the activation of the AMP-activated protein kinase (AMPK) in a mammal that includes the step of administering to a patient, preferably a human, in need of such treatment a therapeutically effective amount of a compound or a pharmaceutical composition of the present invention.

Diseases and conditions mediated by agonists of the AMP-activated protein kinase (AMPK) embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the AMP-activated protein kinase (AMPK), in particular diseases or conditions as described hereinbefore and hereinafter.

In yet another aspect the present invention relates a method for treating a disease or condition mediated by the activation of the AMP-activated protein kinase (AMPK) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

Preliminary Remarks

As a rule, $^1$H-NMR and/or mass spectra have been obtained for the compounds prepared. The $R_f$ values are determined using Merck silica gel 60 $F_{254}$ plates and UV light at 254 nm.

The terms "ambient temperature" and "room temperature" are used interchangeably and designate a temperature of about 20° C.

Analytical HPLC parameters employed for characterization of products (TFA denotes trifluoroacetic acid and FA denotes formic acid):

| Method: | 1 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [Acetonitrile] | Flow [mL/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 2 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [Acetonitrile] | Flow [mL/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 3 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [CH$_3$CN] | Flow [mL/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 4 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [CH$_3$CN] | Flow [mL/min] | Temperature [° C.] |
| --- | --- | --- | --- | --- |
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 5 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [CH$_3$CN] | Flow [mL/min] | Temperature [° C.] |
| --- | --- | --- | --- | --- |
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

The Examples that follow are intended to illustrate the present invention without restricting it:

Intermediate 1

(3R,3aR,6R,6aR)-6-(6-Chloro-5-iodo-3-(2-trimethylsilanyl-ethoxymethyl)-3H-imidazo[4,5-b]pyridin-2-yloxy)hexahydrofuro[3,2-b]furan-3-ol

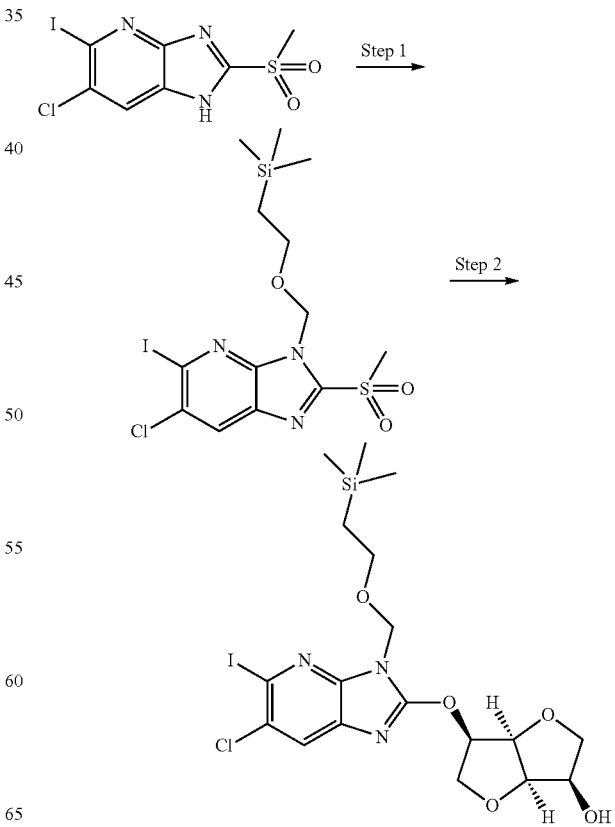

Step 1: 6-Chloro-5-iodo-2-(methylsulfonyl)-3-(2-trimethylsilanyl-ethoxymethyl)-3H-imidazo[4,5-b]pyridine 6-Chloro-5-iodo-2-(methylsulfonyl)-1H-imidazo[4,5-b]pyridine (for preparation see WO 2012116145; 1.5 g) and triethylamine (875 µL) are dissolved in tetrahydrofurane (12 mL), cooled to 0° C. and treated with (2-(chloromethoxy)ethyl)trimethylsilane (SEM-Cl; 890 µL). The mixture is stirred for 30 minutes while warming to room temperature. Then the mixture is partitioned between saturated aqueous NH$_4$Cl and ethylacetate. The organic phase is washed with water and brine. After drying (MgSO$_4$) the solvents are evaporated in vacuo to give the title compound. LC (method 1): t$_R$=1.22 min; Mass spectrum (ESI$^+$): m/z=488 [M+H]$^+$.

Step 2: (3R,3aR,6R,6aR)-6-(6-Chloro-5-iodo-3-(2-trimethylsilanyl-ethoxymethyl)-3H-imidazo[4,5-b]pyridin-2-yloxy)hexahydrofuro[3,2-b]furan-3-ol (3R,3aR,6R,6aR)-Hexahydrofuro[3,2-b]furan-3,6-diol (1.84 g) is dissolved in N,N-dimethylformamide (10 mL) and treated with 1,8-diazabicyclo[5.4.0]undec-7-ene (DBU; 1.9 mL). A solution of 6-chloro-5-iodo-2-(methylsulfonyl)-3-(2-trimethylsilanyl-ethoxymethyl)-3H-imidazo[4,5-b]pyridine (2.05 g) in N,N-dimethylformamide (20 mL) is added dropwise and the mixture is stirred for 2 hours at room temperature. The mixture is partitioned between water and ethylacetate and the organic phase is washed with brine and dried (MgSO$_4$). The solvents are evaporated in vacuo and the residue is chromatographed on silica gel (cyclohexane/ethyl acetate 80:20→0:100) to give the title compound. LC (method 1): t$_R$=1.17 min; Mass spectrum (ESI$^+$): m/z=554 [M+H]$^+$.

Intermediate 2

Ethyl 1-(4-(4,4,5,5-tetramethyl-1,3,2-dioxaborolan-2-yl)phenyl)piperidin-4-ylcarbamate

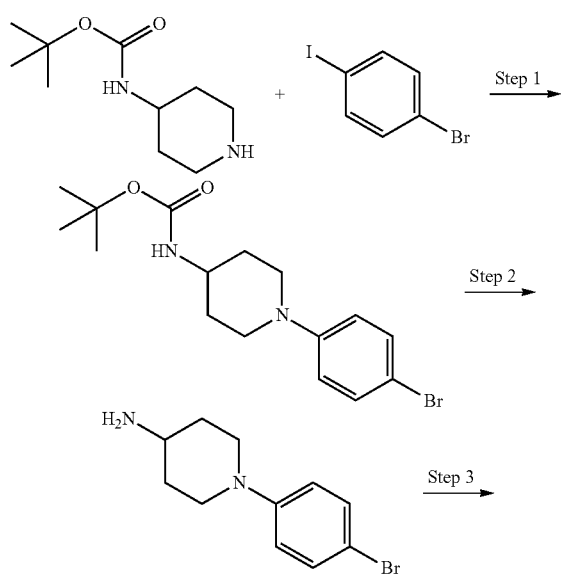

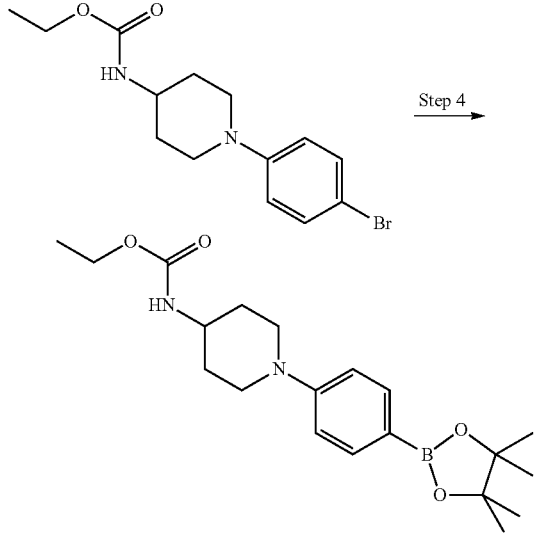

Step 1: tert-Butyl 1-(4-bromophenyl)piperidin-4-ylcarbamate tert-Butyl piperidin-4-ylcarbamate (500 mg), 1-bromo-4-iodobenzene (710 mg) and Cs$_2$CO$_3$ (1.2 g) are dissolved in 1,4-dioxane (15 mL) and purged for 10 minutes with argon. 4,5-Bis-(diphenylphosphino)-9,9-dimethylxanthen (Xantphos, 115 mg) and tris-(dibenzylideneacetone)-dipalladium-(0) (Pd$_2$(dba)$_3$, 45 mg) are added and the mixture is heated for 12 hours at 110° C. Then the mixture is partitioned between saturated aqueous NH$_4$Cl solution and ethylacetate and the organic phase is washed with brine and dried (MgSO$_4$). The solvents are evaporated in vacuo and the residue is chromatographed on silica gel (cyclohexane/ethyl acetate 99:1→70:30) to give the title compound. LC (method 2): t$_R$=1.14 min; Mass spectrum (ESI$^+$): m/z=355 [M+H]$^+$.

Step 2: 1-(4-Bromophenyl)piperidin-4-amine tert-Butyl 1-(4-bromophenyl)piperidin-4-ylcarbamate (365 mg) is dissolved in dichloromethane (10 mL), treated with trifluoroacetic acid (780 µL) and stirred for 6 hours at room temperature. Then the mixture is partitioned between dichloromethane and saturated aqueous K$_2$CO$_3$ solution and stirred vigorously for 30 minutes. The phases are separated and the organic phase is washed with saturated aqueous K$_2$CO$_3$ solution. The organic phase is dried (MgSO$_4$) and concentrated to give the title compound. LC (method 2): t$_R$=0.93 min; Mass spectrum (ESI$^+$): m/z=255 [M+H]$^+$.

Step 3: Ethyl 1-(4-bromophenyl)piperidin-4-ylcarbamate 1-(4-Bromophenyl)piperidin-4-amine (255 mg) and triethylamine (280 µL) are dissolved in dichloromethane (3 mL), treated with ethyl chloroformate (105 µL) and stirred for 2 hours. The mixture is partitioned between dichloromethane and water. The organic phase is washed with water and the combined aqueous phases are extracted with dichlo-

Step 4: Ethyl 1-(4-(4,4,5,5-tetramethyl-1,3,2-dioxaborolan-2-yl)phenyl)piperidin-4-ylcarbamate A microwave suited vial charged with a stir bar, ethyl 1-(4-bromophenyl)piperidin-4-ylcarbamate (235 mg), 4,4,4',4',5,5,5',5'-octamethyl-2,2'-bi(1,3,2-dioxaborolane) (225 mg), KOAc (210 mg) and dimethylsulfoxide (5 mL) is purged for 10 minutes with argon. [1,1'-Bis(diphenylphosphino)-ferrocene]-dichloropalladium(II)-CH$_2$Cl$_2$-complex (PdCl$_2$(dppf) (60 mg) is added, the vial is sealed and the mixture is stirred for 12 hours at 60° C. Then the mixture is partitioned between saturated aqueous NH$_4$Cl solution and ethylacetate and the organic phase is dried (MgSO$_4$). The solvents are evaporated in vacuo and the residue is chromatographed on silica gel (cyclohexane/ethyl acetate 80:20→50:50). The product thus obtained is further purified by HPLC on reversed phase to give the title compound. LC (method 2): $t_R$=1.09 min; Mass spectrum (ESI$^+$): m/z=375 [M+H]$^+$.

Intermediate 3

Ethyl 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-ylcarbamate

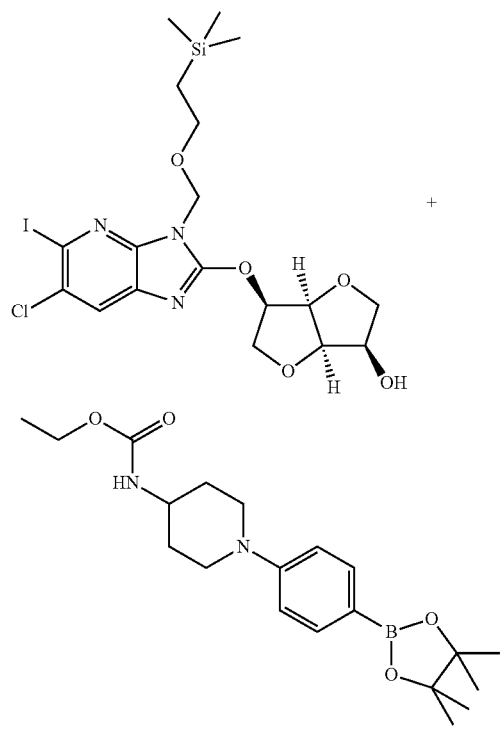

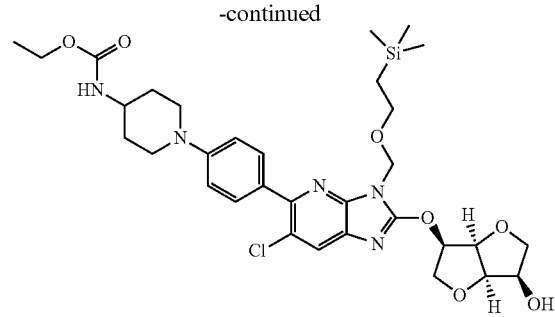

A microwave suited vial charged with a stir bar, (3R,3aR,6R,6aR)-6-(6-chloro-5-iodo-3-((2-(trimethylsilyl)ethoxy)methyl)-3H-imidazo[4,5-b]pyridin-2-yloxy)hexahydrofuro[3,2-b]furan-3-ol (60 mg), ethyl 1-(4-(4,4,5,5-tetramethyl-1,3,2-dioxaborolan-2-yl)phenyl)piperidin-4-ylcarbamate (45 mg), Na$_2$CO$_3$ (2 M aqueous solution, 163 μL) and 1,4-dioxane (2 mL) is purged for 15 minutes with argon. [1,1'-Bis(diphenylphosphino)-ferrocene]-dichloropalladium(II)-CH$_2$Cl$_2$-complex (PdCl$_2$(dppf)xCH$_2$Cl$_2$) (9 mg) is added, the vial is sealed and the mixture is stirred for 12 hours at 90° C. Then the mixture is partitioned between saturated aqueous NH$_4$Cl solution and ethylacetate. The phases are separated and the organic phase is dried (MgSO$_4$) and concentrated. The residue is chromatographed on silica gel (cyclohexane/ethyl acetate 60:40→20:80) to give the title compound. LC (method 1): $t_R$=1.01 min; Mass spectrum (ESI$^+$): m/z=674 [M+H]$^+$.

Intermediate 4

1-(4-(4,4,5,5-Tetramethyl-1,3,2-dioxaborolan-2-yl)phenyl)piperidin-4-yl dimethylcarbamate

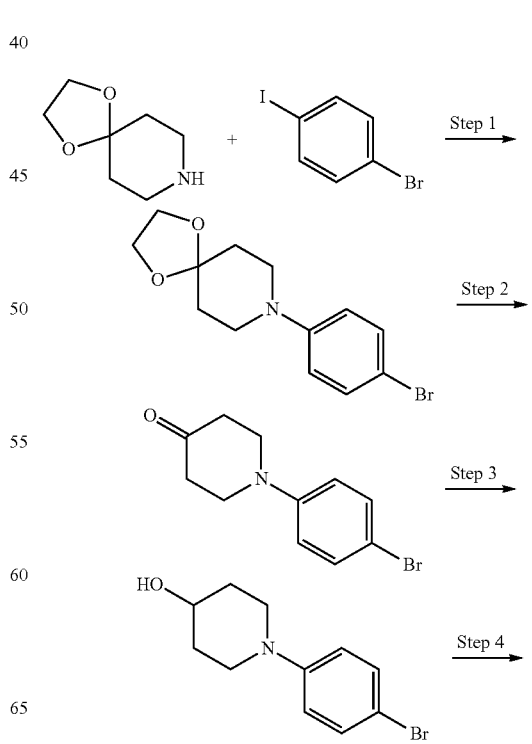

-continued

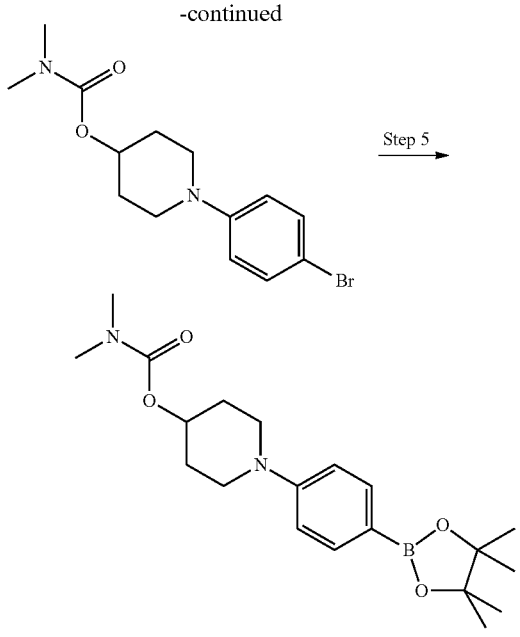

Step 1:
8-(4-Bromophenyl)-1,4-dioxa-8-azaspiro[4.5]decane 1,4-Dioxa-8-azaspiro[4.5]decane (1.63 mL) and 1-bromo-4-iodobenzene (3 g) are dissolved in toluene (75 mL), treated with sodium tert-butoxide (1.53 g) and purged for 10 minutes with argon. Acetato-(2'-di-tert.-butylphosphino-1,1'-biphenyl-2-yl)-palladium-(II) (245 mg) is added and the mixture is heated for 15 minutes at 140° C. Then the mixture is partitioned between saturated aqueous $NH_4Cl$ solution and ethylacetate. The organic phase is washed with brine and dried ($MgSO_4$). The solvents are evaporated in vacuo and the residue is chromatographed on silica gel (cyclohexane/ethyl acetate 99:1→70:30) to give the title compound. LC (method 2): $t_R$=1.06 min; Mass spectrum (ESI$^+$): m/z=298 [M+H]$^+$.

Step 2: 1-(4-Bromophenyl)piperidin-4-one

A mixture of 8-(4-bromophenyl)-1,4-dioxa-8-azaspiro[4.5]decane (1.02 g) and half concentrated hydrochloric acid is heated for 12 hours at 50° C., poured on ice and aqueous NaOH solution (4 M) is added until pH ~7-8. Then the mixture is extracted with ethylacetate and the organic phase is washed with brine and dried ($MgSO_4$). The solvents are evaporated in vacuo to give the title compound. LC (method 2): $t_R$=0.96 min; Mass spectrum (ESI$^+$): m/z=254 [M+H]$^+$.

Step 3: 1-(4-Bromophenyl)piperidin-4-ol 1-(4-Bromophenyl)piperidin-4-one (765 mg) is dissolved under argon in MeOH (8 mL), cooled to 0° C. and treated with $NaBH_4$ (145 mg). The mixture is stirred for 2 hours at 0° C., treated with saturated aqueous $NaHCO_3$ solution and stirred for 10 minutes. Then the mixture is extracted with ethylacetate and the organic phase is washed with brine and dried ($MgSO_4$). The solvents are evaporated to give the title compound. LC (method 2): $t_R$=0.92 min; Mass spectrum (ESI$^+$): m/z=256 [M+H]$^+$.

Step 4: 1-(4-Bromophenyl)piperidin-4-yl dimethylcarbamate 1-(4-Bromophenyl)piperidin-4-ol (200 mg) is dissolved under argon in tetrahydrofurane (4 mL), cooled to 0° C. and treated with NaH (60% in mineral oil, 36 mg). The mixture is stirred for 30 minutes, treated with dropwise with dimethylcarbamoylchloride (110 μL) and stirred for 4 hours at room temperature. Then the mixture is partitioned between water and ethylacetate. The organic phase is washed with water and brine and is dried ($MgSO_4$). The solvents are evaporated in vacuo and the residue is chromatographed on silica gel (cyclohexane/ethyl acetate 99:1→50:50) to give the title compound. LC (method 3): $t_R$=1.05 min; Mass spectrum (ESI$^+$): m/z=327 [M+H]$^+$.

Step 5: 1-(4-(4,4,5,5-Tetramethyl-1,3,2-dioxaborolan-2-yl)phenyl)piperidin-4-yl dimethylcarbamate A microwave suited vial charged with a stir bar, 1-(4-bromophenyl)piperidin-4-yl dimethylcarbamate (86 mg), 4,4,4',4',5,5,5',5'-octamethyl-2,2'-bi(1,3,2-dioxaborolane) (82 mg), KOAc (78 mg) and 1,4-dioxane (2 mL) is purged for 10 minutes with argon. [1,1'-Bis(diphenylphosphino)-ferrocene]-dichloropalladium(II) ($PdCl_2$(dppf) (11 mg) is added, the vial is sealed and the mixture is stirred for 12 hours at 90° C. Then the mixture is partitioned between water and ethylacetate and the organic phase is washed with water and brine. Then the organic phase is dried ($MgSO_4$) and concentrated. The residue is chromatographed on silica gel (cyclohexane/ethyl acetate 99:1→50:50). The product thus obtained is further purified by HPLC on reversed phase to give the title compound. LC (method 1): $t_R$=0.92 min; Mass spectrum (ESI$^+$): m/z=375 [M+H]$^+$.

Intermediate 5

1-(4-(6-Chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-yl dimethylcarbamate

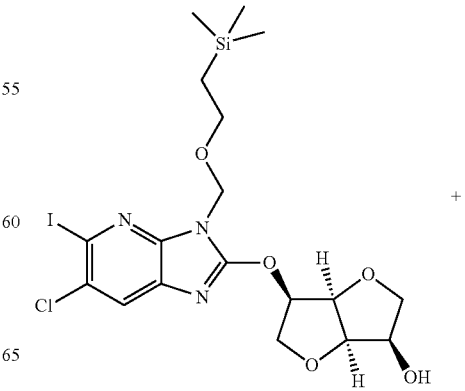

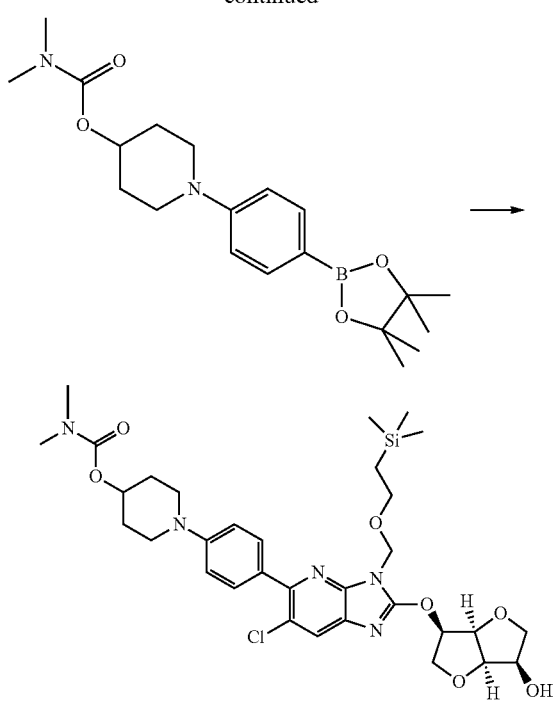

The title compound is prepared from (3R,3aR,6R,6aR)-6-(6-chloro-5-iodo-3-((2-(trimethylsilyl)ethoxy)methyl)-3H-imidazo[4,5-b]pyridin-2-yloxy)hexahydrofuro[3,2-b]furan-3-ol and 1-(4-(4,4,5,5-tetramethyl-1,3,2-dioxaborolan-2-yl)phenyl)piperidin-4-yl dimethylcarbamate following a procedure analogous to that described for Intermediate 3. LC (method 1): $t_R$=1.04 min; Mass spectrum (ESI$^+$): m/z=674 [M+H]$^+$.

Intermediate 6

2-(4-((cis)-4-Azidocyclohexyl)phenyl)-4,4,5,5-tetramethyl-1,3,2-dioxaborolane

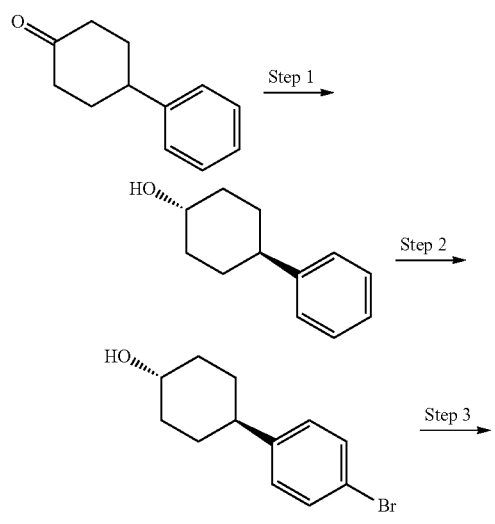

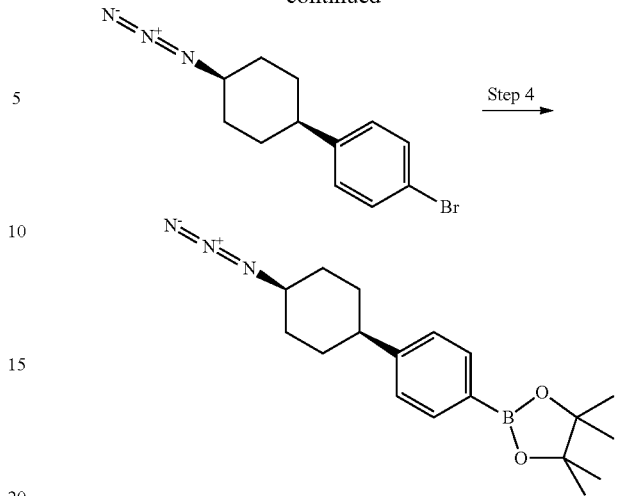

Step 1: (trans)-4-Phenylcyclohexanol

4-Phenylcyclohexanone (4 g) is dissolved under argon in MeOH (25 mL), cooled to 0° C. and treated portionwise with NaBH$_4$ (900 mg). The mixture is stirred for 12 hours while warming to room temperature. The mixture is concentrated and then treated dropwise with water (10 mL). Then concentrated hydrochloric acid (8 mL) is added dropwise. The mixture is extracted with ethylacetate and the organic phase is washed with brine and dried (Na$_2$SO$_4$). The solvents are evaporated and the residue is crystallized from cyclohexane to give the title compound. TLC: $r_f$=0.52 (silicagel, dichloromethane/ethanol 19:1).

Step 2: (trans)-4-(4-Bromophenyl)cyclohexanol (trans)-4-Phenylcyclohexanol (2 g) is dissolved in dichloromethane (40 mL) and cooled to −8° C. AlCl$_3$ (3 g) is added portionwise and the mixture is stirred for further 15 minutes after addition is complete. Then a solution of bromine (1.87 mL) in dichloromethane (10 mL) is added dropwise. The mixture is stirred for 10 minutes and is then partitioned between dichloromethane and ice-water. Concentrated hydrochloric acid (20 mL) is added, the phases are separated and the aqueous phase is extracted 3 times with dichloromethane. The combined organic phases are dried (Na$_2$SO$_4$) and concentrated. The residue is chromatographed on silica gel (cyclohexane/ethyl acetate 2:1) to give the title compound. TLC: $r_f$=0.3 (silicagel, cyclohexane/ethylacetate 2:1).

Step 3: 1-((cis)-4-Azidocyclohexyl)-4-bromobenzene (trans)-4-(4-Bromophenyl)cyclohexanol (500 mg) is dissolved under argon in tetrahydrofurane (8 mL) and cooled to −5° C. Triphenylphosphine (770 mg) and di-tert-butyl-azodicarboxylate (550 mg) are added and the mixture is stirred for 5 minutes. A solution of diphenylphosphorylazide (650 μL) in tetrahydrofurane (8 mL) is added dropwise during 2 hours and the mixture is stirred at 0° C. for 48 hours. Then the mixture is diluted with diethylether, washed with saturated aqueous NaHCO$_3$ solution and the organic phase is dried (MgSO$_4$) and concentrated. The residue is chromatographed on silica gel (petrole ether/ethyl acetate 99:1→70:30) to give the title compound. LC (method 4): $t_R$=0.97 min.

Step 4: 2-(4-((cis)-4-Azidocyclohexyl)phenyl)-4,4,5,5-tetramethyl-1,3,2-dioxaborolane A microwave suited vial charged with a stir bar, 1-((cis)-4-azidocyclohexyl)-4-bromobenzene (360 mg), 4,4,4',4',5,5,5',5'-octamethyl-2,2'-bi(1,3,2-dioxaborolane) (490 mg), KOAc (360 mg) and 1,4-dioxane (15 mL) is purged for 10 minutes with argon. Bis(di-tert-butyl(4-dimethylaminophenyl)phosphine)dichloropalladium-(II) (Pd(amphos)Cl$_2$ (45 mg) is added, the vial is sealed and the mixture is stirred for 1 hour at 100° C. Then the mixture is partitioned between saturated aqueous NH$_4$Cl solution and diethylether and the organic phase is dried (MgSO$_4$). The solvents are evaporated in vacuo and the residue is chromatographed on silica gel (cyclohexane/ethyl acetate 99:1→80:20) to give the title compound. LC (method 3): t$_R$=1.26 min; Mass spectrum (ESI$^+$): m/z=328 [M+H]$^+$.

Intermediate 7

Cyclopentyl (cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate

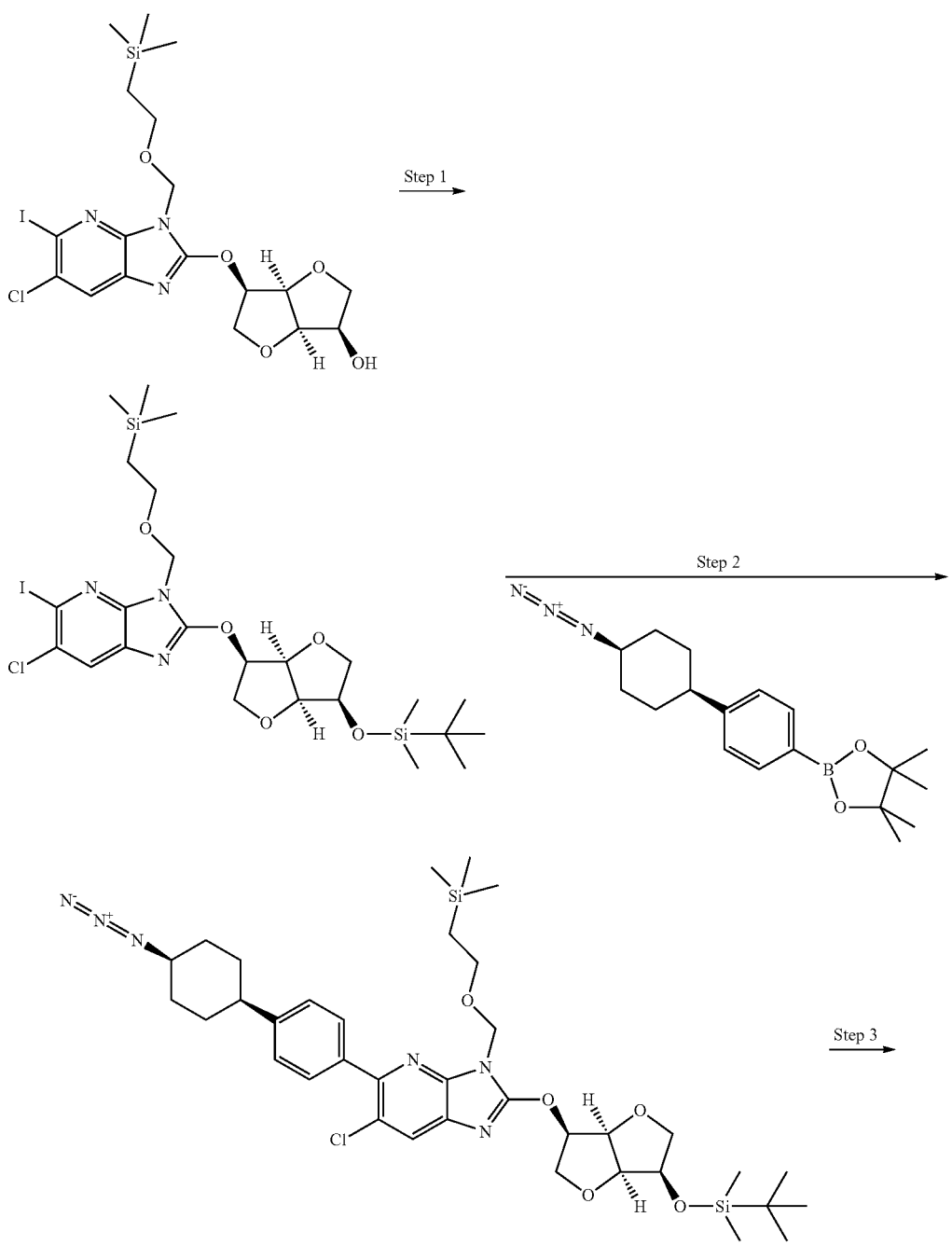

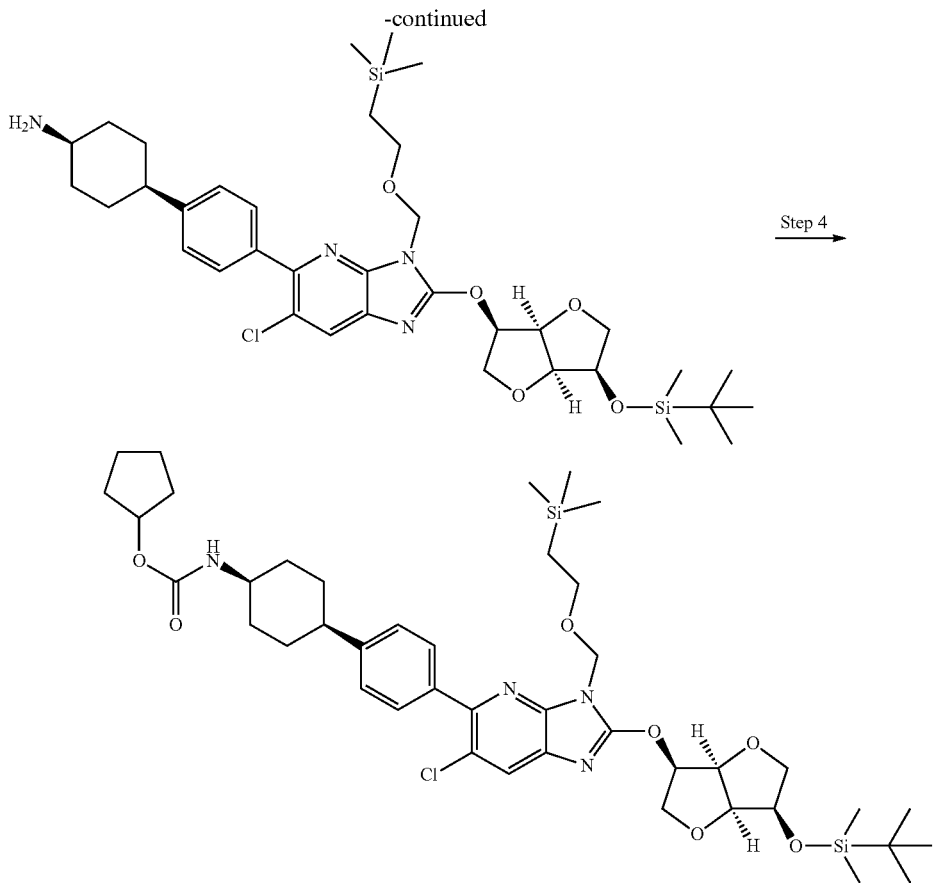

Step 1: 2-((3R,3aR,6R,6aS)-6-(tert-butyldimethylsilyloxy)hexahydrofuro[3,2-b]furan-3-yloxy)-6-chloro-5-iodo-3-((2-(trimethylsilyl)ethoxy)methyl)-3H-imidazo[4,5-b]pyridine (3R,3aR,6R,6aR)-6-(6-Chloro-5-iodo-3-((2-(trimethylsilyl)ethoxy)methyl)-3H-imidazo[4,5-b]pyridin-2-yloxy)hexahydrofuro[3,2-b]furan-3-ol (500 mg) and imidazol (120 mg) are dissolved in N,N-dimethylformamide (2 mL), treated with tert-butylchlorodimethylsilane (220 mg) and stirred for 4 hours. Then the mixture is partitioned between saturated aqueous NH$_4$Cl solution and diethylether. The phases are separated and the organic phase is dried (MgSO$_4$) and concentrated. The residue is chromatographed on silica gel (cyclohexane/ethyl acetate 99:1→70:30) to give the title compound. LC (method 3): t$_R$=1.35 min; Mass spectrum (ESI$^+$): m/z=668 [M+H]$^+$.

Step 2: 5-(4-((cis)-4-Azidocyclohexyl)phenyl)-2-((3R,3aR,6R,6aS)-6-(tert-butyldimethylsilyloxy)hexahydrofuro[3,2-b]furan-3-yloxy)-6-chloro-3-((2-(trimethylsilyl)-ethoxy)methyl)-3H-imidazo[4,5-b]pyridine A microwave suited vial charged with a stir bar, 2-((3R,3aR,6R,6aS)-6-(tert-butyldimethylsilyloxy)hexahydrofuro[3,2-b]furan-3-yloxy)-6-chloro-5-iodo-3-((2-(trimethylsilyl)ethoxy)methyl)-3H-imidazo[4,5-b]pyridine (250 mg), 2-(4-((cis)-4-azidocyclohexyl)phenyl)-4,4,5,5-tetramethyl-1,3,2-dioxaborolane (130 mg), K$_2$CO$_3$ (180 mg), ethanol (4 mL) and water (2 mL) is purged for 15 minutes with argon. Bis(di-tert-butyl(4-dimethylaminophenyl)phosphine) dichloropalladium-(11) (Pd(amphos)Cl$_2$ (13.5 mg) is added, the vial is sealed and the mixture is stirred for 1 hours at 80° C. Then the mixture is partitioned between saturated aqueous NH$_4$Cl solution and diethylether. The phases are separated and the organic phase is dried (MgSO$_4$) and concentrated. The residue is chromatographed on silica gel (cyclohexane/ethyl acetate 90:10→60:40) to give the title compound. LC (method 4): t$_R$=1.31 min; Mass spectrum (ESI$^+$): m/z=741 [M+H]$^+$.

Step 3: (cis)-4-(4-(2-((3R,3aR,6R,6aS)-6-(tert-Butyldimethylsilyloxy)hexahydrofuro-[3,2-b]furan-3-yloxy)-6-chloro-3-((2-(trimethylsilyl)ethoxy)methyl)-3H-imidazo[4,5-b]pyridin-5-yl)phenyl)cyclohexanamine 5-(4-((cis)-4-Azidocyclohexyl)phenyl)-2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridine (210 mg) is dissolved in tetrahydrofurane (1 mL) treated with triphenylphosphine (90 mg) and stirred for 4 hours at room temperature and for 12 hours at 40° C. Water (220 μL) is added and the mixture is stirred for further 12 hours at 80° C. Then the mixture is partitioned between hydrochloric acid (1 M) and diethylether. The organic phase is washed with aqueous NaOH solution (1 M), dried (MgSO$_4$) and concentrated. The residue is chromatographed over aluminium oxide (ethyl acetate/methanol 100:0→0:100) to give the title compound. LC (method 4): t$_R$=0.61 min; Mass spectrum (ESI$^+$): m/z=715 [M+H]$^+$.

Step 4: Cyclopentyl (cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate (cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanamine (30 mg) and triethylamine (12 μL) are dissolved in dichloromethane (2 mL), treated with cyclopentyl chloroformate (6.5 μL) and stirred for 2 hours. Triethylamine (12 μL) and cyclopentyl chloroformate (6.5 μL) are added and the mixture is stirred for 12 hours. Then triethylamine (24 μL) and cyclopentyl chloroformate (13 μL) are added and the mixture is stirred for 2 hours. The mixture is partitioned between dichloromethane and saturated aqueous NH$_4$Cl solution. The organic phase is dried (MgSO$_4$) and concentrated. The crude product is used directly in the next step.

Intermediate 8

Methyl (cis)-4-(4-(2-((3R,3aR,6R,6aS)-6-(tert-butyldimethylsilyloxy)hexahydrofuro-[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate

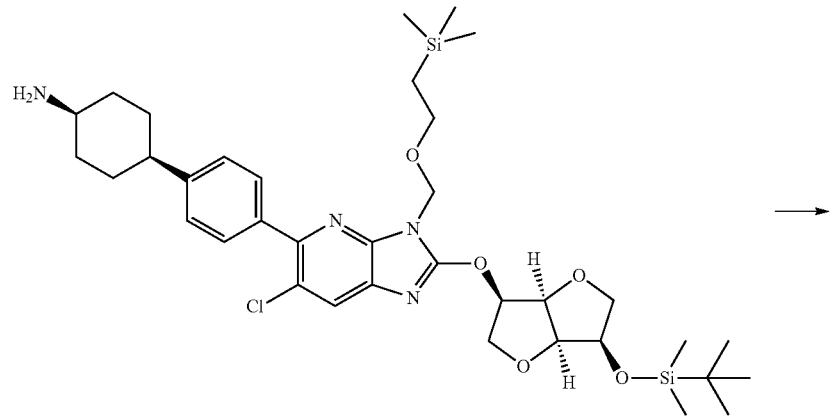

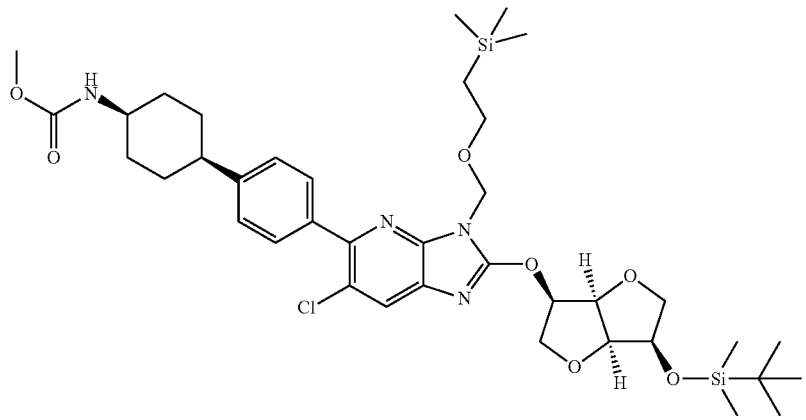

(cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanamine (50 mg) and triethylamine (30 μL) are dissolved in dichloromethane (2 mL), treated with methyl chloroformate (11 μL) and stirred for 2 hours. The mixture is partitioned between dichloromethane and saturated aqueous NH$_4$Cl solution. The organic phase is dried (MgSO$_4$) and concentrated. The crude product is used directly in the next step. LC (method 4): $t_R$=1.19 min; Mass spectrum (ESI$^+$): m/z=773 [M+H]$^+$.

Intermediate 9

Isopropyl (cis)-4-(4-(2-((3R,3aR,6R,6aS)-6-(tert-butyldimethylsilyloxy)hexahydrofuro-[3,2-b]furan-3-yloxy)-6-chloro-3-((2-(trimethylsilyl)ethoxy)methyl)-3H-imidazo[4,5-b]-pyridin-5-yl)phenyl)cyclohexylcarbamate

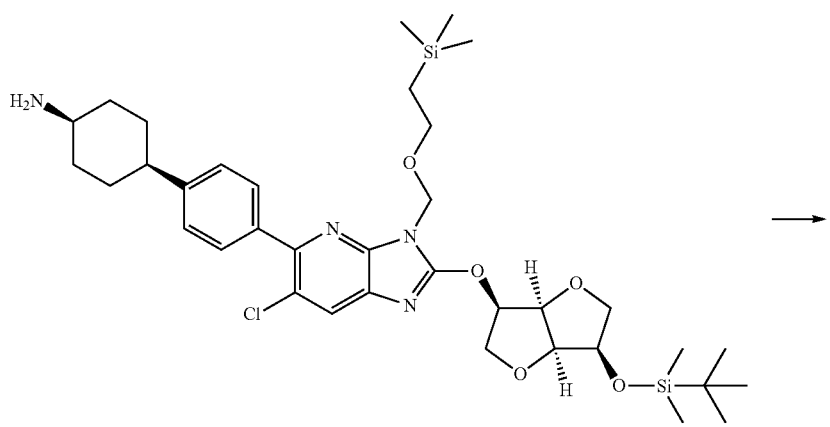

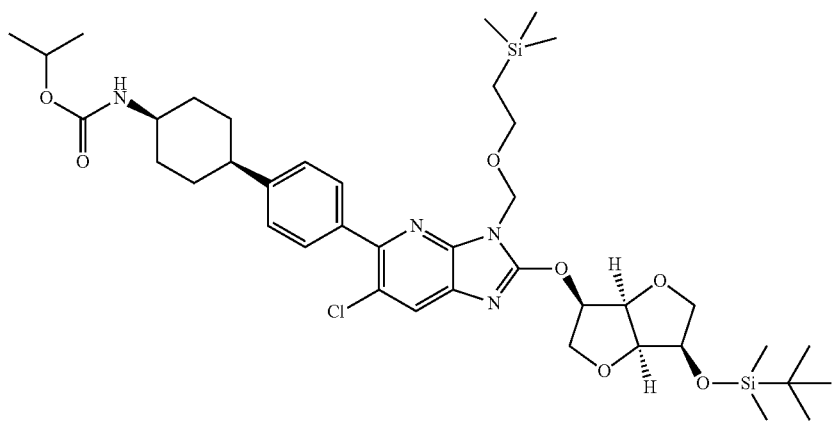

The title compound is prepared from (cis)-4-(4-(2-((3R, 3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanamine and isopropyl chloroformate following a procedure analogous to that described for Intermediate 8.

Intermediate 10

Tetrahydro-2H-pyran-4-yl (cis)-4-(4-(2-((3R,3aR, 6R,6aS)-6-(tert-butyldimethylsilyl-oxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate

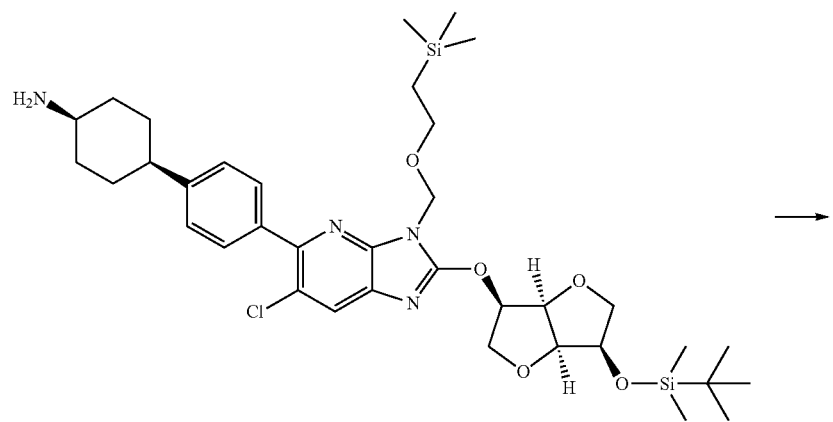

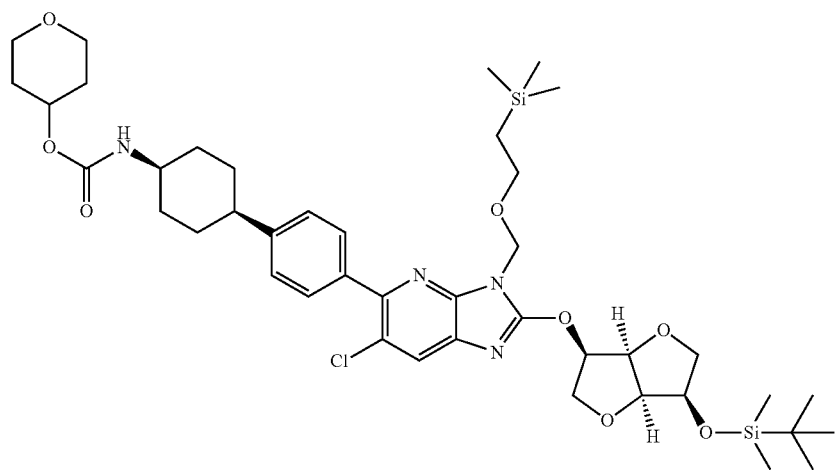

(cis)-4-(4-(2-((3R,3aR,6R,6aS)-6-(tert-Butyldimethylsilyloxy)hexahydrofuro[3,2-b]-furan-3-yloxy)-6-chloro-3-((2-(trimethylsilyl)ethoxy)methyl)-3H-imidazo[4,5-b]pyridin-5-yl)phenyl)cyclohexanamine (40 mg) is dissolved in toluene (2 mL), treated dropwise with a solution of diphosgene (6.8 µL) in toluene (2 mL), stirred for 10 minutes at room temperature and for 1.5 hours at 60° C. Then tetrahydro-2H-pyran-4-ol (5.3 µL) is added and the mixture is stirred for 48 hours at 60° C. The mixture is partitioned between ethylacetate and saturated aqueous NH$_4$Cl solution. The organic phase is dried (MgSO$_4$) and concentrated. The crude product is used directly in the next step.

Intermediate 11

(trans)-4-(4-(4,4,5,5-Tetramethyl-1,3,2-dioxaborolan-2-yl)phenyl)cyclohexanol

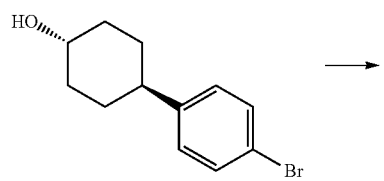

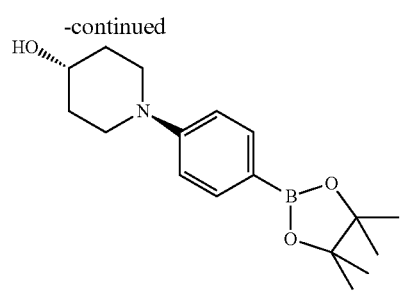

The title compound is prepared from (trans)-4-(4-bromophenyl)cyclohexanol and 4,4,4',4',5,5,5',5'-octamethyl-2,2'-bi(1,3,2-dioxaborolane) following a procedure analogous to that described for Intermediate 6 Step 4. LC (method 1): $t_R$=1.09 min; Mass spectrum (ESI$^+$): m/z=303 [M+H]$^+$.

Intermediate 12

(trans)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl morpholine-4-carboxylate

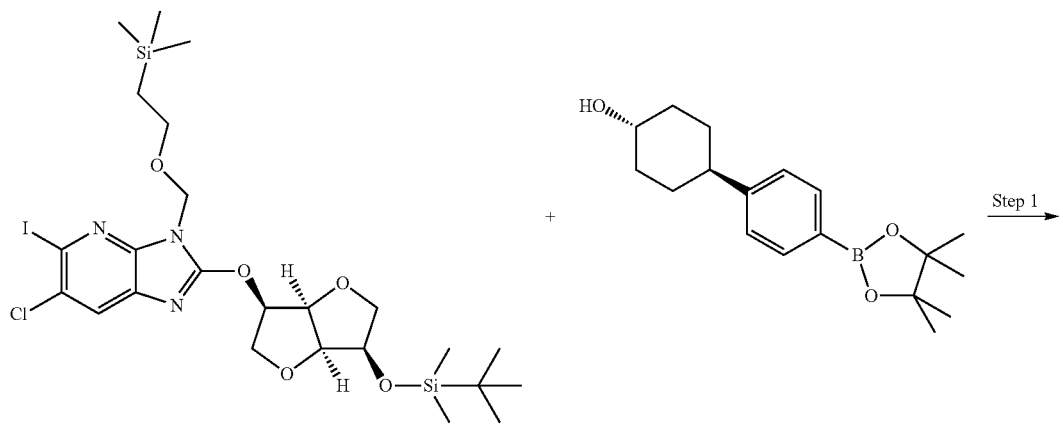

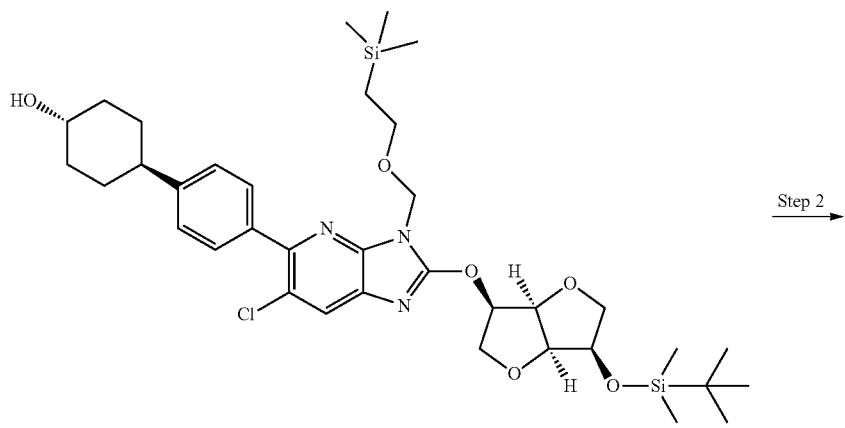

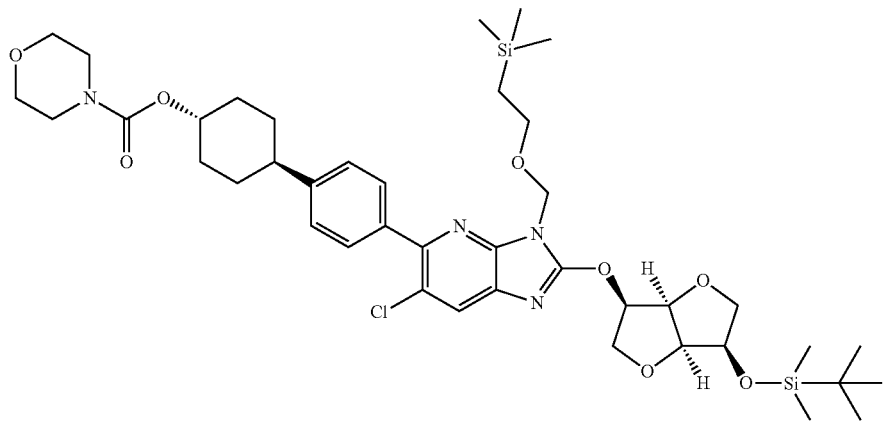

Step 1: (trans)-4-(4-(2-((3R,3aR,6R,6aS)-6-(tert-Butyldimethylsilyloxy)hexahydrofuro-[3,2-b]furan-3-yloxy)-6-chloro-3-((2-(trimethylsilyl)ethoxy)methyl)-3H-imidazo[4,5-b]-pyridin-5-yl)phenyl)cyclohexanol The title compound is prepared from 2-((3R,3aR,6R,6aS)-6-(tert-butyldimethylsilyloxy)hexahydrofuro[3,2-b]furan-3-yloxy)-6-chloro-5-iodo-3-((2-(trimethylsilyl)ethoxy)methyl)-3H-imidazo[4,5-b]pyridine and (trans)-4-(4-(4,4,5,5-tetramethyl-1,3,2-dioxaborolan-2-yl)phenyl)cyclohexanol following a procedure analogous to that described for Intermediate 7 Step 2. LC (method 5): $t_R$=1.16 min; Mass spectrum (ESI$^+$): m/z=716 [M+H]$^+$.

Step 2: (trans)-4-(4-(2-((3R,3aR,6R,6aS)-6-(tert-Butyldimethylsilyloxy)hexahydrofuro-[3,2-b]furan-3-yloxy)-6-chloro-3-((2-(trimethylsilyl)ethoxy)methyl)-3H-imidazo[4,5-b]-pyridin-5-yl)phenyl)cyclohexyl morpholine-4-carboxylate (trans)-4-(4-(2-((3R,3aR,6R,6aS)-6-(tert-Butyldimethylsilyloxy)hexahydrofuro[3,2-b]-furan-3-yloxy)-6-chloro-3-((2-(trimethylsilyl)ethoxy)methyl)-3H-imidazo[4,5-b]pyridin-5-yl)phenyl)cyclohexanol (50 mg) is dissolved in pyridine (1 mL), treated with morpholine-4-carbonyl chloride (25 μL) and stirred for 12 hours at 50° C. Morpholine-4-carbonyl chloride (25 μL) is added and the mixture is stirred for 2 hours at 50° C. Then morpholine-4-carbonyl chloride (75 μL) is added and the mixture is stirred for 48 hours at 70° C. The mixture is partitioned between ethylacetate and hydrochloric acid (1 M). The organic phase is dried (MgSO$_4$) and concentrated. The crude product is used directly in the next step.

Intermediate 13

(trans)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl ethylcarbamate

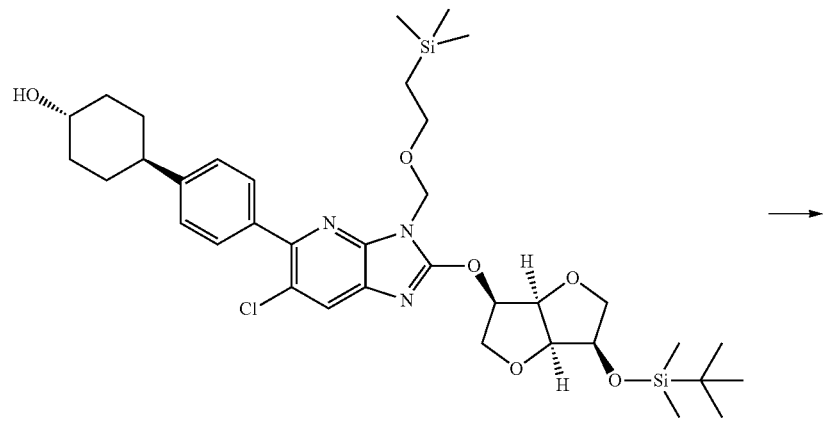

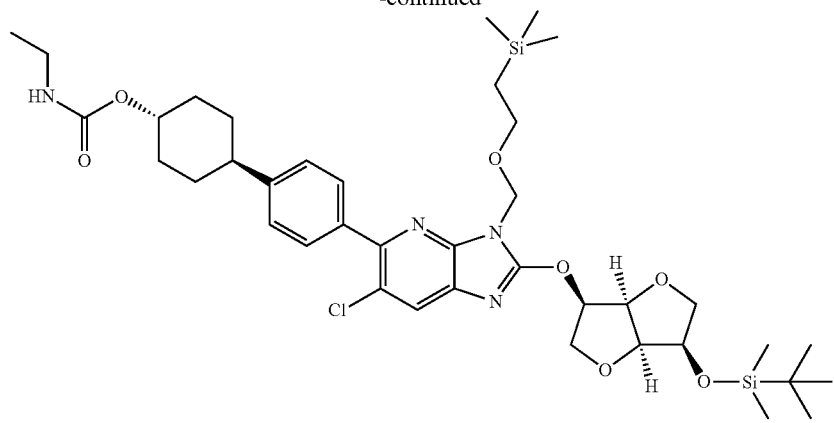

(trans)-4-(4-(2-((3R,3aR,6R,6aS)-6-(tert-Butyldimethylsilyloxy)hexahydrofuro[3,2-b]-furan-3-yloxy)-6-chloro-3-((2-(trimethylsilyl)ethoxy)methyl)-3H-imidazo[4,5-b]pyridin-5-yl)phenyl)cyclohexanol (50 mg) and triethylamine (20 μL) are dissolved in tetrahydrofurane (2 mL), treated with isocyanatoethane (8 μL) and stirred for 12 hours. Triethylamine (20 μL) and isocyanatoethane (8 μL) are added and the mixture is stirred for 48 hours. The mixture is partitioned between ethylacetate and saturated aqueous NH$_4$Cl solution. The organic phase is dried (MgSO$_4$) and concentrated. The residue is purified by HPLC on reversed phase to give the title compound. LC (method 5): $t_R$=1.26 min; Mass spectrum (ESI$^+$): m/z=787 [M+H]$^+$.

Intermediate 14

(trans)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl isopropylcarbamate

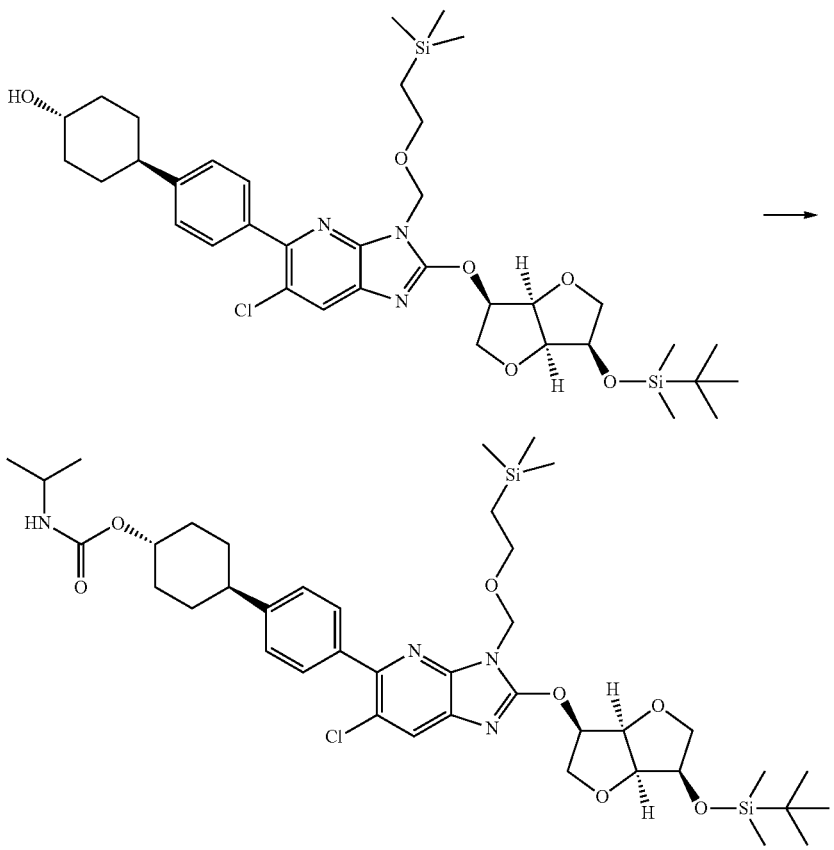

The title compound is prepared from (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanol and 2-isocyanatopropane following a procedure analogous to that described for Intermediate 13. LC (method 5): $t_R$=1.28 min.

Intermediate 15

(trans)-4-(4-(2-((3R,3aR,6R,6aS)-6-(tert-Butyldimethylsilyloxy)hexahydrofuro[3,2-b]-furan-3-yloxy)-6-chloro-3-((2-(trimethylsilyl)ethoxy)methyl)-3H-imidazo[4,5-b]pyridin-5-yl)phenyl)cyclohexyl pyrrolidine-1-carboxylate

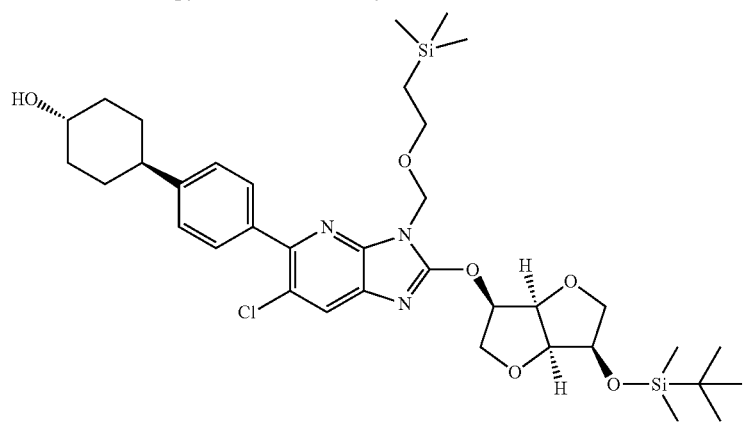

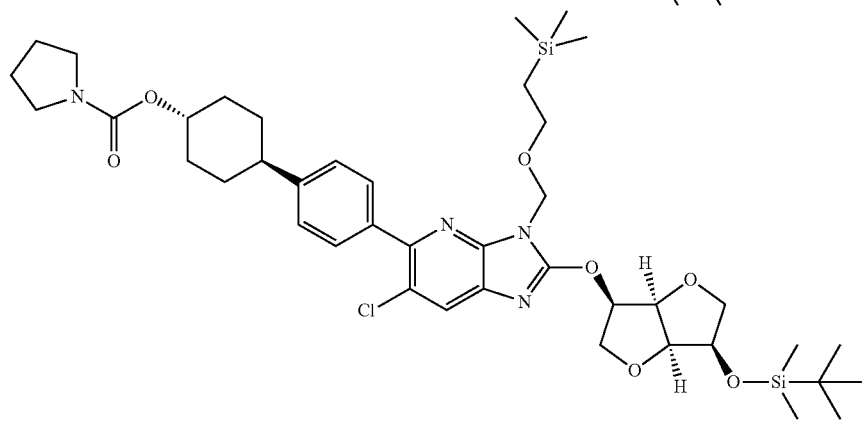

The title compound is prepared from (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanol and pyrrolidine-1-carbonyl chloride following a procedure analogous to that described for Intermediate 12 Step 2 but heating the mixture for 48 hours at 100° C. LC (method 5): $t_R$=1.32 min.

Intermediate 16

(cis)-4-(4-(4,4,5,5-Tetramethyl-1,3,2-dioxaborolan-2-yl)phenyl)cyclohexanol

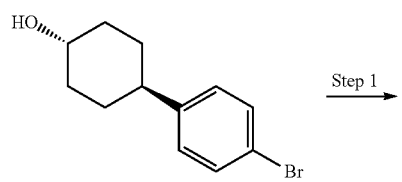

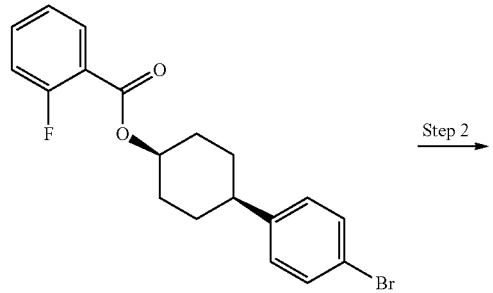

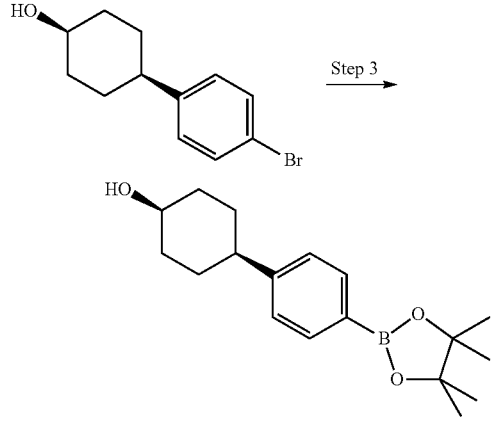

Step 1: (cis)-4-(4-Bromophenyl)cyclohexyl 2-fluorobenzoate (trans)-4-(4-Bromophenyl)cyclohexanol (100 mg), 2-fluorobenzoic acid (130 mg) and triphenylphosphine (225 mg) are dissolved in tetrahydrofurane (2 mL), treated dropwise with diisopropylazodicarboxylate (170 μL) and the mixture is stirred for 12 hours. Then the mixture is partitioned between ethylacetate and saturated aqueous NaHCO₃ solution. The organic phase is dried (MgSO₄) and concentrated. The residue is chromatographed on silica gel (cyclohexane/ethyl acetate 99:1→70:30) to give the title compound. LC (method 1): $t_R$=1.29 min; Mass spectrum (ESI⁺): m/z=399 [M+Na]⁺.

Step 2: (cis)-4-(4-bromophenyl)cyclohexanol (cis)-4-(4-Bromophenyl)cyclohexyl 2-fluorobenzoate (110 mg) is dissolved in methanol (2 mL), treated with aqueous NaOH solution (1 M, 875 μL) and the mixture is stirred for 48 hours at room temperature and for 5 hours at 40° C. Then the mixture is neutralized with hydrochloric acid (1 M), partitioned between ethylacetate and brine. The organic phase is dried (MgSO₄) and concentrated. The residue is chromatographed on silica gel (cyclohexane/ethyl acetate 90:10→70:30) to give the title compound. LC (method 1): $t_R$=1.04 min; Mass spectrum (ESI⁺): m/z=237 [M−H₂O+H]⁺.

Step 3: (cis)-4-(4-(4,4,5,5-Tetramethyl-1,3,2-dioxaborolan-2-yl)phenyl)cyclohexanol The title compound is prepared from (cis)-4-(4-bromophenyl)cyclohexanol and 4,4,4',4',5,5,5',5'-octamethyl-2,2'-bi(1,3,2-dioxaborolane) following a procedure analogous to that described for Intermediate 6 Step 4. LC (method 1): $t_R$=1.11 min; Mass spectrum (ESI⁺): m/z=303 [M+H]⁺.

Intermediate 17

(cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl ethylcarbamate

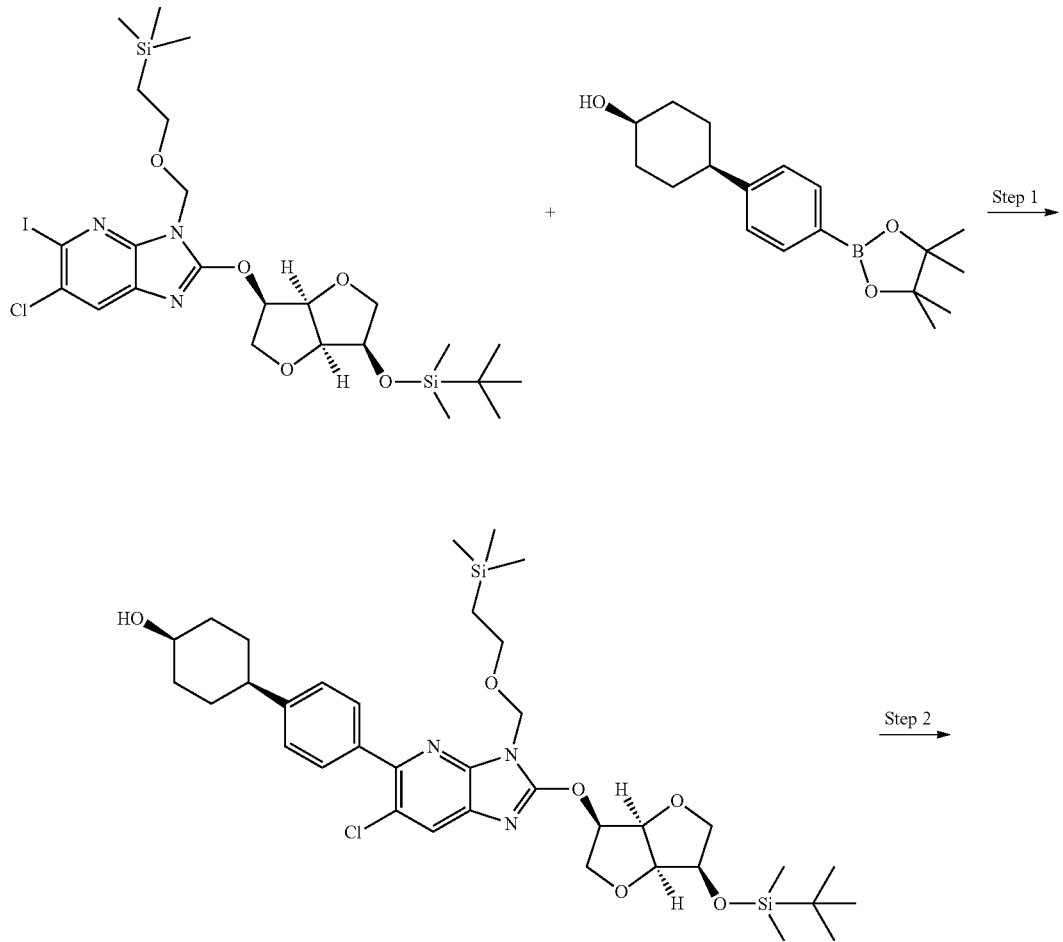

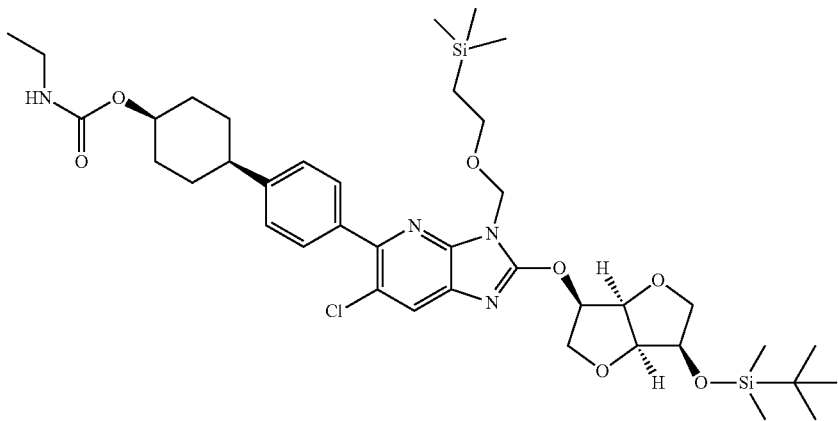

Step 1: (cis)-4-(4-(2-((3R,3aR,6R,6aS)-6-(tert-Butyldimethylsilyloxy)hexahydrofuro-[3,2-b]furan-3-yloxy)-6-chloro-3-((2-(trimethylsilyl)ethoxy)methyl)-3H-imidazo[4,5-b]-pyridin-5-yl)phenyl)cyclohexanol The title compound is prepared from 2-((3R,3aR,6R,6aS)-6-(tert-butyldimethylsilyloxy)hexahydrofuro[3,2-b]furan-3-yloxy)-6-chloro-5-iodo-3-((2-(tri-methylsilyl)ethoxy)methyl)-3H-imidazo[4,5-b]pyridine and (cis)-4-(4-(4,4,5,5-tetramethyl-1,3,2-dioxaborolan-2-yl)phenyl)cyclohexanol following a procedure analogous to that described for Intermediate 7 Step 2. LC (method 5): $t_R$=1.21 min; Mass spectrum (ESI$^+$): m/z=716 [M+H]$^+$.

Step 2: (cis)-4-(4-(2-((3R,3aR,6R,6aS)-6-(tert-Butyldimethylsilyloxy)hexahydrofuro-[3,2-b]furan-3-yloxy)-6-chloro-3-((2-(trimethylsilyl)ethoxy)methyl)-3H-imidazo[4,5-b]-pyridin-5-yl)phenyl) cyclohexyl ethylcarbamate (cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanol (50 mg), 4-dimethylaminopyridine (DMAP, 1 mg) and triethylamine (30 μL) are dissolved in tetrahydrofurane (1 mL), treated with isocyanatoethane (11 μL) and stirred for 6 hours. Triethylamine (60 μL) and isocyanatoethane (22 μL) are added and the mixture is stirred for 12 hours at 70° C. The mixture is partitioned between ethylacetate and saturated aqueous NH$_4$Cl solution. The organic phase is dried (MgSO$_4$) and concentrated. The residue is used directly in the next step. LC (method 4): $t_R$=1.20 min; Mass spectrum (ESI$^+$): m/z=787 [M+H]$^+$.

Intermediate 18

(cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl isopropylcarbamate

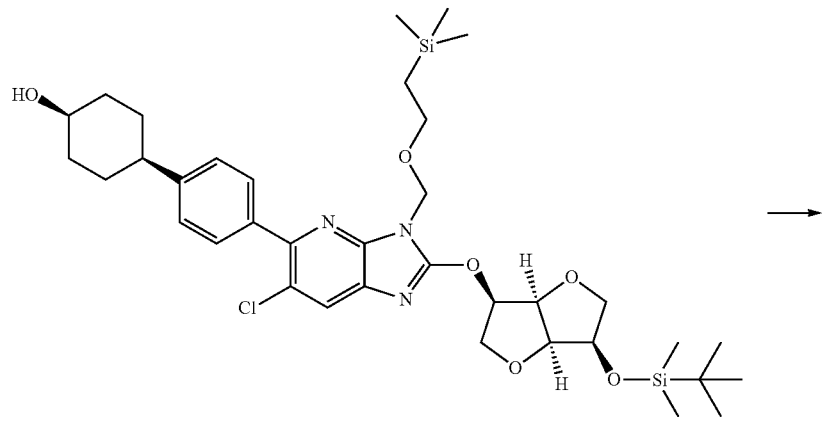

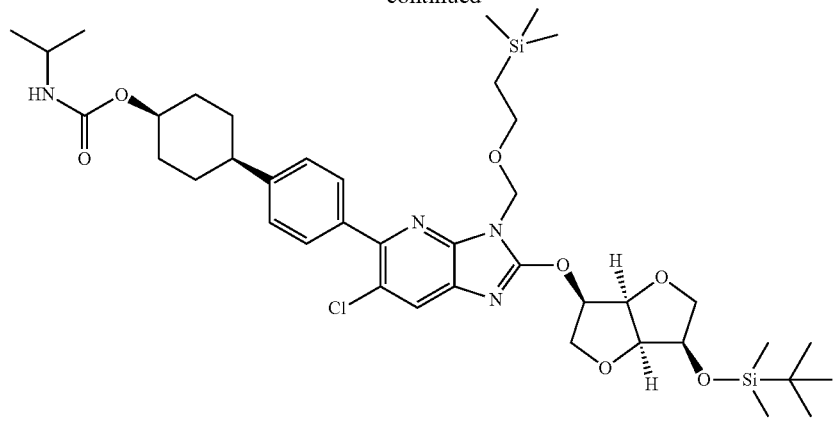

(cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanol (50 mg), 4-dimethylaminopyridine (DMAP, 1 mg) and triethylamine (30 µL) are dissolved in tetrahydrofurane (1 mL), treated with 2-isocyanatopropane (14 µL) and stirred for 12 hours. Triethylamine (60 µL) and isocyanatoethane (28 µL) are added and the mixture is stirred for 12 hours at 70° C. Again triethylamine (60 µL) and isocyanatoethane (28 µL) are added and the mixture is stirred for 12 hours at 70° C. The mixture is partitioned between ethylacetate and saturated aqueous NH₄Cl solution. The organic phase is dried (MgSO₄) and concentrated. The residue is used directly in the next step.

Intermediate 19

(cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl morpholine-4-carboxylate

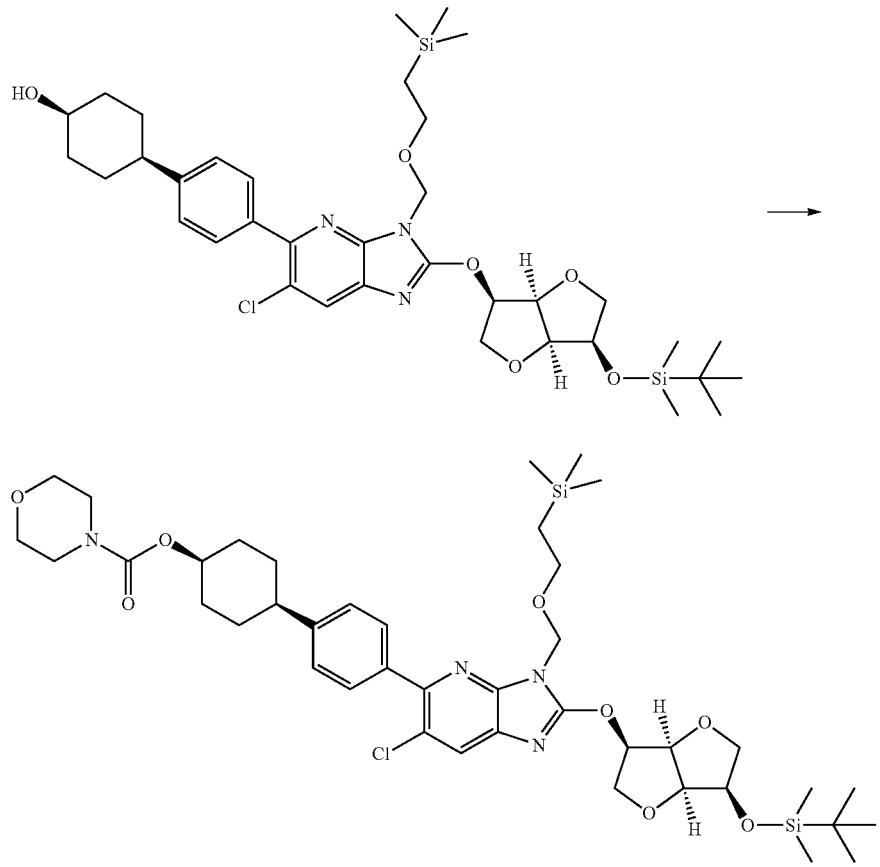

(cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanol (50 mg) is dissolved in pyridine (1 mL), treated with morpholine-4-carbonyl chloride (25 μL) and stirred for 6 hours at 50° C. Morpholine-4-carbonyl chloride (75 μL) is added and the mixture is stirred for 12 hours at 70° C. Morpholine-4-carbonyl chloride (75 μL) is added and the mixture is stirred for 6 hours at 70° C. Again morpholine-4-carbonyl chloride (250 μL) is added and the mixture is stirred for 12 hours at 70° C. The mixture is partitioned between ethylacetate and hydrochloric acid (1 M). The organic phase is dried (MgSO₄) and concentrated. The crude product is used directly in the next step.

Intermediate 20

(cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl pyrrolidine-1-carboxylate

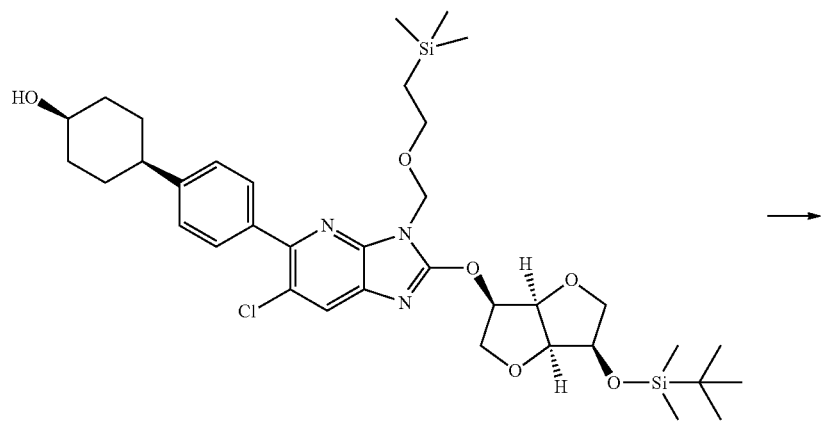

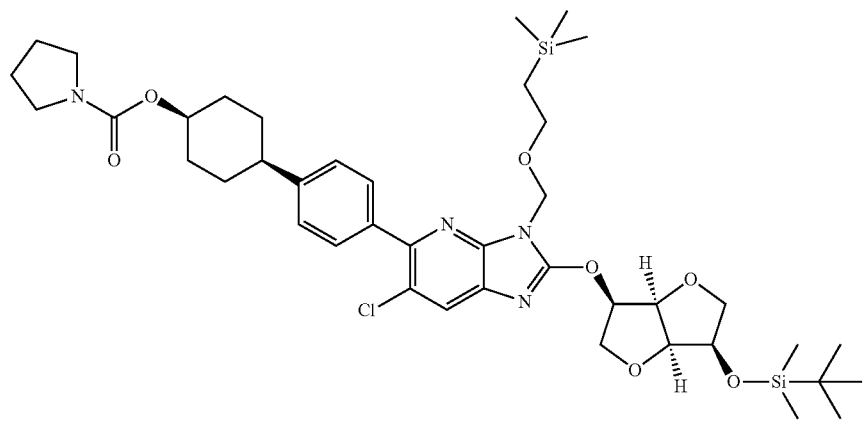

(cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanol (50 mg) is dissolved in pyridine (1 mL), treated with pyrrolidine-1-carbonyl chloride (80 µL) and stirred for 12 hours at 70° C. Pyrrolidine-1-carbonyl chloride (160 µL) is added and the mixture is stirred for 48 hours at 100° C.

The mixture is partitioned between ethylacetate and hydrochloric acid (1 M). The organic phase is dried (MgSO$_4$) and concentrated. The crude product is used directly in the next step.

Intermediate 21

(3R,3aR,6R,6aR)-6-(5-(4-Bromophenyl)-6-chloro-3-((2-(trimethylsilyl)ethoxy)methyl)-3H-imidazo[4,5-b]pyridin-2-yloxy)hexahydrofuro[3,2-b]furan-3-ol

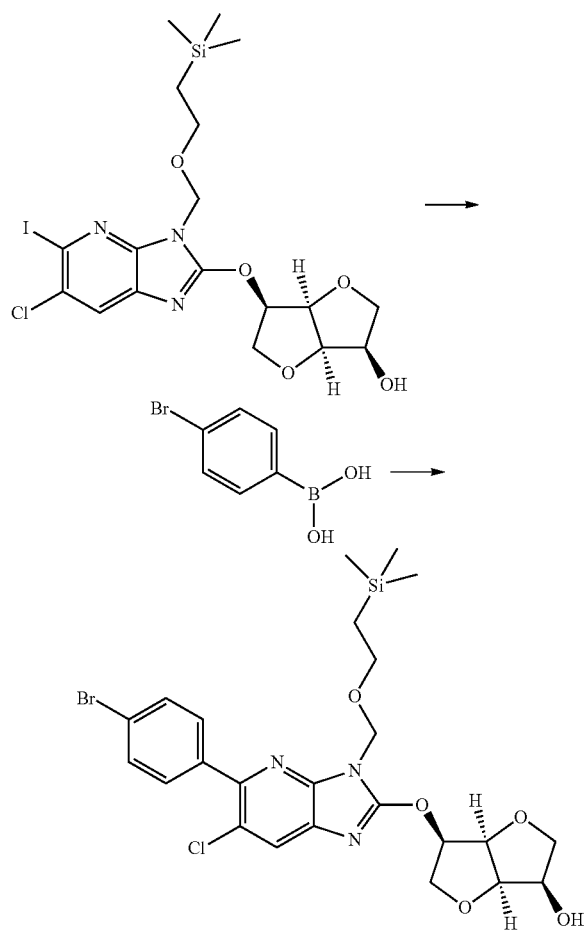

The title compound is prepared from (3R,3aR,6R,6aR)-6-(6-chloro-5-iodo-3-((2-(trimethylsilyl)ethoxy)methyl)-3H-imidazo[4,5-b]pyridin-2-yloxy)hexahydrofuro[3,2-b]furan-3-ol and 4-bromophenylboronic acid following a procedure analogous to that described for Intermediate 3. LC (method 2): $t_R$=1.24 min; Mass spectrum (ESI$^+$): m/z=582 [M+H]$^+$.

Intermediate 22

Piperidin-4-yl isopropylcarbamate

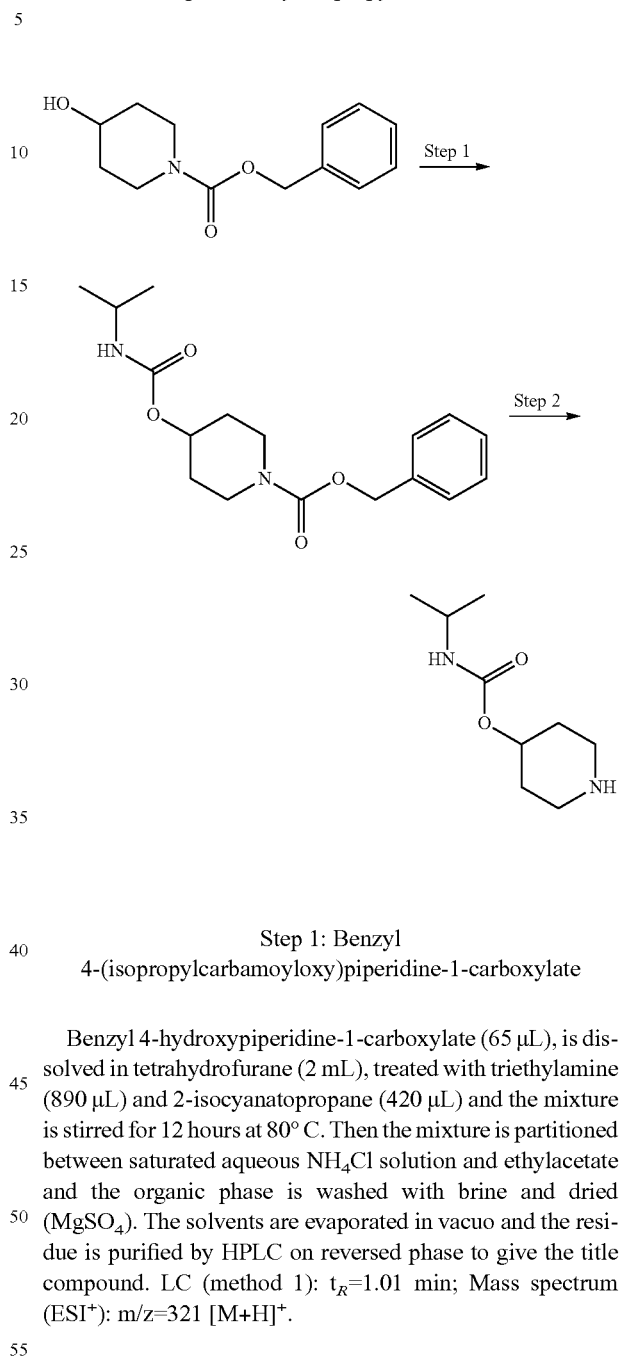

Step 1: Benzyl 4-(isopropylcarbamoyloxy)piperidine-1-carboxylate

Benzyl 4-hydroxypiperidine-1-carboxylate (65 µL), is dissolved in tetrahydrofurane (2 mL), treated with triethylamine (890 µL) and 2-isocyanatopropane (420 µL) and the mixture is stirred for 12 hours at 80° C. Then the mixture is partitioned between saturated aqueous NH$_4$Cl solution and ethylacetate and the organic phase is washed with brine and dried (MgSO$_4$). The solvents are evaporated in vacuo and the residue is purified by HPLC on reversed phase to give the title compound. LC (method 1): $t_R$=1.01 min; Mass spectrum (ESI$^+$): m/z=321 [M+H]$^+$.

Step 2: Piperidin-4-yl isopropylcarbamate

Benzyl 4-(isopropylcarbamoyloxy)piperidine-1-carboxylate (113 mg) is dissolved in ethanol (3 mL), treated with palladium on carbon (10%, 38 mg) and the mixture is hydrogenated at room temperature for 8 hours under 3 bar hydrogen pressure. Then the catalyst is filtered off and washed with ethanol. The combined mother liquours are concentrated to give the title compound, which is used directly in the next step.

Intermediate 23

1-(4-(6-Chloro-2-((3R,3aR,6R,6aR)-6-hydroxy-hexahydrofuro[3,2-b]furan-3-yloxy)-3-((2-(trimethylsilyl)ethoxy)methyl)-3H-imidazo[4,5-b]pyridin-5-yl)phenyl)piperidin-4-yl isopropylcarbamate

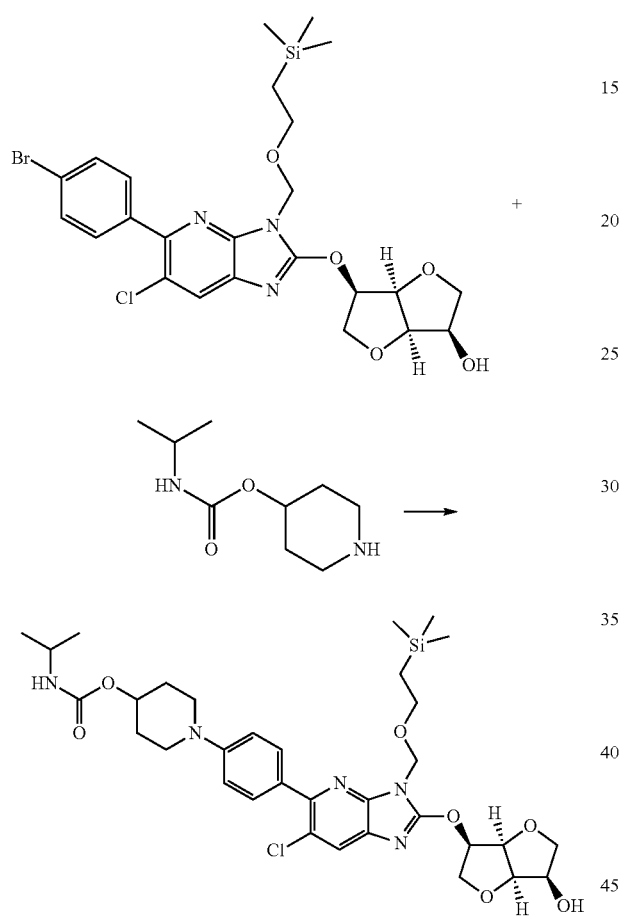

A microwave suited vial charged with a stir bar, (3R,3aR,6R,6aR)-6-(5-(4-Bromophenyl)-6-chloro-3-((2-(trimethylsilyl)ethoxy)methyl)-3H-imidazo[4,5-b]pyridin-2-yloxy)hexahydrofuro[3,2-b]furan-3-ol (75 mg), piperidin-4-yl isopropylcarbamate (31 mg) and $Cs_2CO_3$ (130 mg) in 1,4-dioxane (2 mL) is purged for 10 minutes with argon. Chloro-(2-dicyclohexylphosphino-2',6'-diisopropoxy-1,1'-biphenyl)[2-(2-aminoethyl)phenal]palladium(II) methyl-tert.-butyl-ether adduct (RuPhos-precatalyst, 11 mg) and 2-dicyclohexylphosphino-2',6'-diisopropoxybiphenyl (RuPhos, 6 mg) are added, the vial is sealed and the mixture is heated for 12 hours to 120° C. Then the mixture is partitioned between saturated aqueous $NH_4Cl$ solution and ethylacetate and the organic phase is dried ($MgSO_4$). The solvents are evaporated in vacuo and the residue is purified by HPLC on reversed phase to give the title compound. LC (method 1): $t_R$=1.05 min; Mass spectrum (ESI$^+$): m/z=688 [M+H]$^+$.

Intermediate 24

Piperidin-4-yl morpholine-4-carboxylate

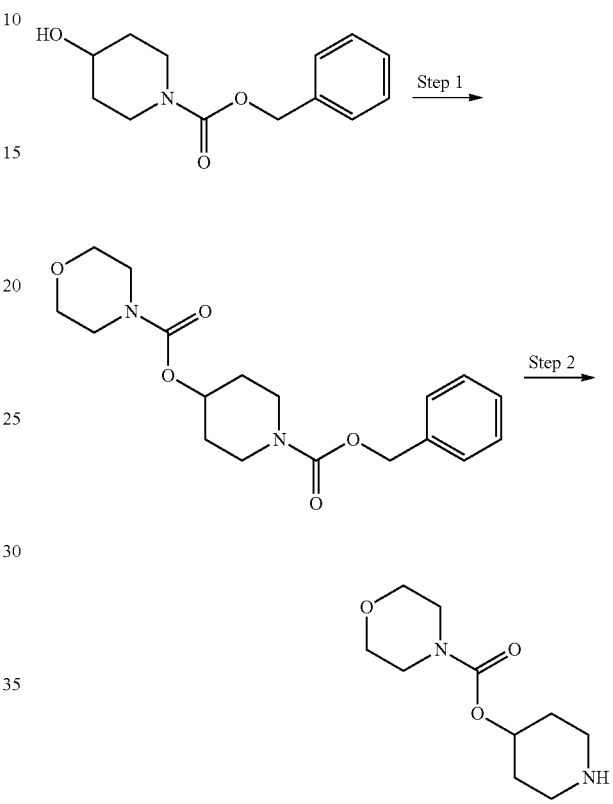

Step 1: 1-(Benzyloxycarbonyl)piperidin-4-yl morpholine-4-carboxylate

Benzyl 4-hydroxypiperidine-1-carboxylate (65 µL) is dissolved in pyridine (2 mL), treated with morpholine-4-carbonyl chloride (500 µL) and stirred for 6 hours at 50° C. Morpholine-4-carbonyl chloride (75 µL) is added and the mixture is stirred for 12 hours at 80° C. Again morpholine-4-carbonyl chloride (500 µL) is added and the mixture is stirred for 12 hours at 80° C. The mixture is partitioned between ethylacetate and hydrochloric acid (1 M). The organic phase is dried ($MgSO_4$) and concentrated. The residue is purified by HPLC on reversed phase to give the title compound. LC (method 1): $t_R$=0.96 min; Mass spectrum (ESI$^+$): m/z=349 [M+H]$^+$.

Step 2: Piperidin-4-yl morpholine-4-carboxylate

The title compound is prepared from 1-(benzyloxycarbonyl)piperidin-4-yl morpholine-4-carboxylate following a procedure analogous to that described for Intermediate 22 Step 2.

Intermediate 25

1-(4-(6-Chloro-2-((3R,3aR,6R,6aR)-6-hydroxy-hexahydrofuro[3,2-b]furan-3-yloxy)-3-((2-(trimethylsilyl)ethoxy)methyl)-3H-imidazo[4,5-b]pyridin-5-yl)phenyl)piperidin-4-yl morpholine-4-carboxylate

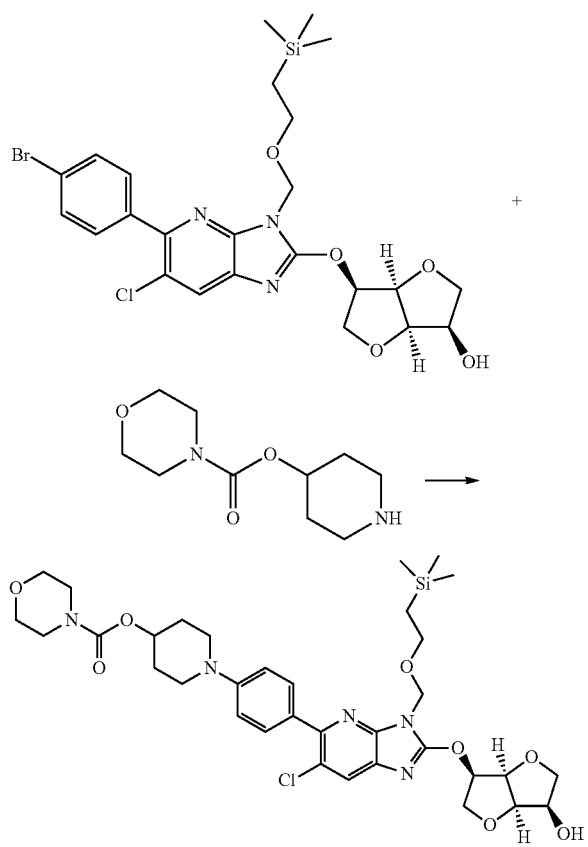

The title compound is prepared from (3R,3aR,6R,6aR)-6-(5-(4-bromophenyl)-6-chloro-3-((2-(trimethylsilyl)ethoxy)methyl)-3H-imidazo[4,5-b]pyridin-2-yloxy)hexahydrofuro[3,2-b]furan-3-ol and piperidin-4-yl morpholine-4-carboxylate following a procedure analogous to that described for Intermediate 23. LC (method 1): $t_R$=1.03 min; Mass spectrum (ESI$^+$): m/z=716 [M+H]$^+$.

Intermediate 26

Isopropyl piperidin-4-ylcarbamate

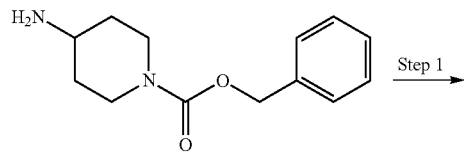

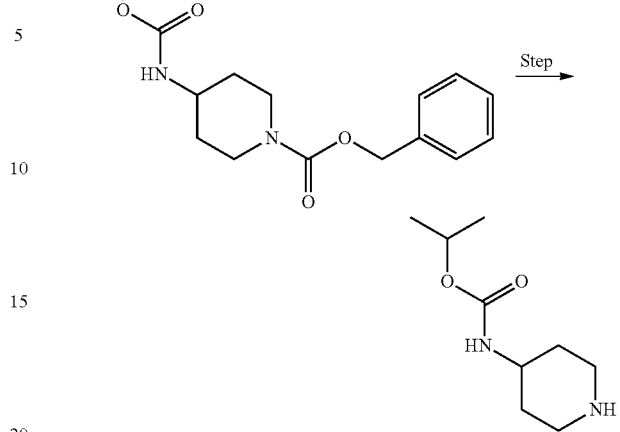

Step 1: Benzyl 4-(isopropoxycarbonylamino)piperidine-1-carboxylate

Benzyl 4-aminopiperidine-1-carboxylate (100 mg) and triethylamine (190 μL) are dissolved in dichloromethane (2 mL), treated with isopropyl chloroformate (920 μL, 1 M solution in toluene) and stirred for 2 hours at room temperature. The mixture is partitioned between dichloromethane and saturated aqueous NH$_4$Cl solution. The organic phase is dried (MgSO$_4$) and concentrated. The residue is purified by HPLC on reversed phase to give the title compound. LC (method 1): $t_R$=1.02 min; Mass spectrum (ESI$^+$): m/z=321 [M+H]$^+$.

Step 2: Isopropyl piperidin-4-ylcarbamate

The title compound is prepared from benzyl 4-(isopropoxycarbonylamino)piperidine-1-carboxylate following a procedure analogous to that described for Intermediate 22 Step 2. Mass spectrum (ESI$^+$): m/z=187 [M+H]$^+$.

Intermediate 27

Isopropyl 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-ylcarbamate

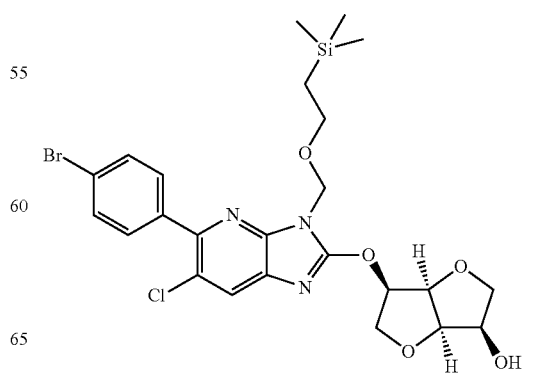

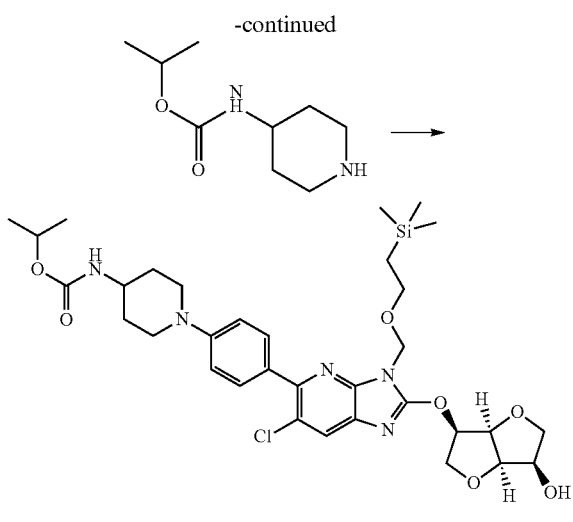

The title compound is prepared from (3R,3aR,6R,6aR)-6-(5-(4-bromophenyl)-6-chloro-3-((2-(trimethylsilyl)ethoxy)methyl)-3H-imidazo[4,5-b]pyridin-2-yloxy)hexahydrofuro[3,2-b]furan-3-ol and isopropyl piperidin-4-ylcarbamate following a procedure analogous to that described for Intermediate 23. LC (method 1): $t_R$=1.04 min; Mass spectrum (ESI⁺): m/z=688 [M+H]⁺.

Intermediate 28

Methyl piperidin-4-ylcarbamate

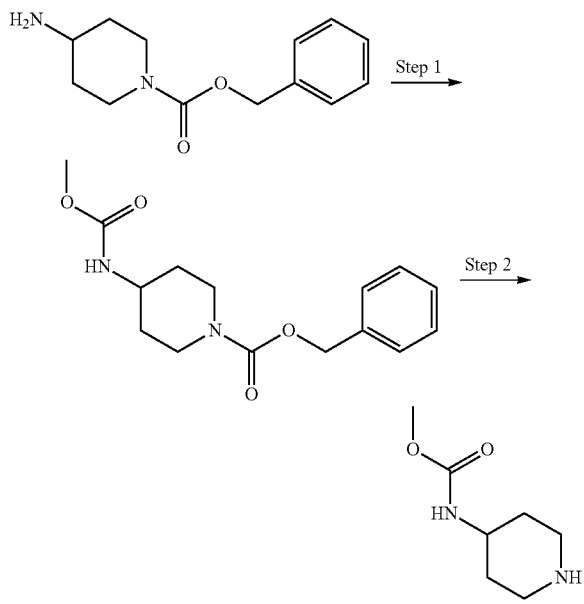

Step 1: Benzyl 4-(methoxycarbonylamino)piperidine-1-carboxylate

The title compound is prepared from benzyl 4-aminopiperidine-1-carboxylate and methyl chloroformate following a procedure analogous to that described for Intermediate 26 Step 1. LC (method 1): $t_R$=0.92 min; Mass spectrum (ESI⁺): m/z=293 [M+H]⁺.

Step 2: Methyl piperidin-4-ylcarbamate

The title compound is prepared from benzyl 4-(methoxycarbonylamino)piperidine-1-carboxylate following a procedure analogous to that described for Intermediate 22 Step 2.

Intermediate 29

Methyl 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-ylcarbamate The title compound is prepared from (3R,3aR,6R,6aR)-6-(5-(4-bromophenyl)-6-chloro-3-((2-(trimethylsilyl)ethoxy)methyl)-3H-imidazo[4,5-b]pyridin-2-yloxy)hexahydrofuro[3,2-b]furan-3-ol and methyl piperidin-4-ylcarbamate following a procedure analogous to that described for Intermediate 23. LC (method 1): $t_R$=0.97 min; Mass spectrum (ESI⁺): m/z=660 [M+H]⁺.

77
Intermediate 30

Cyclopentyl piperidin-4-ylcarbamate

78
Intermediate 31

Cyclopentyl 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-ylcarbamate

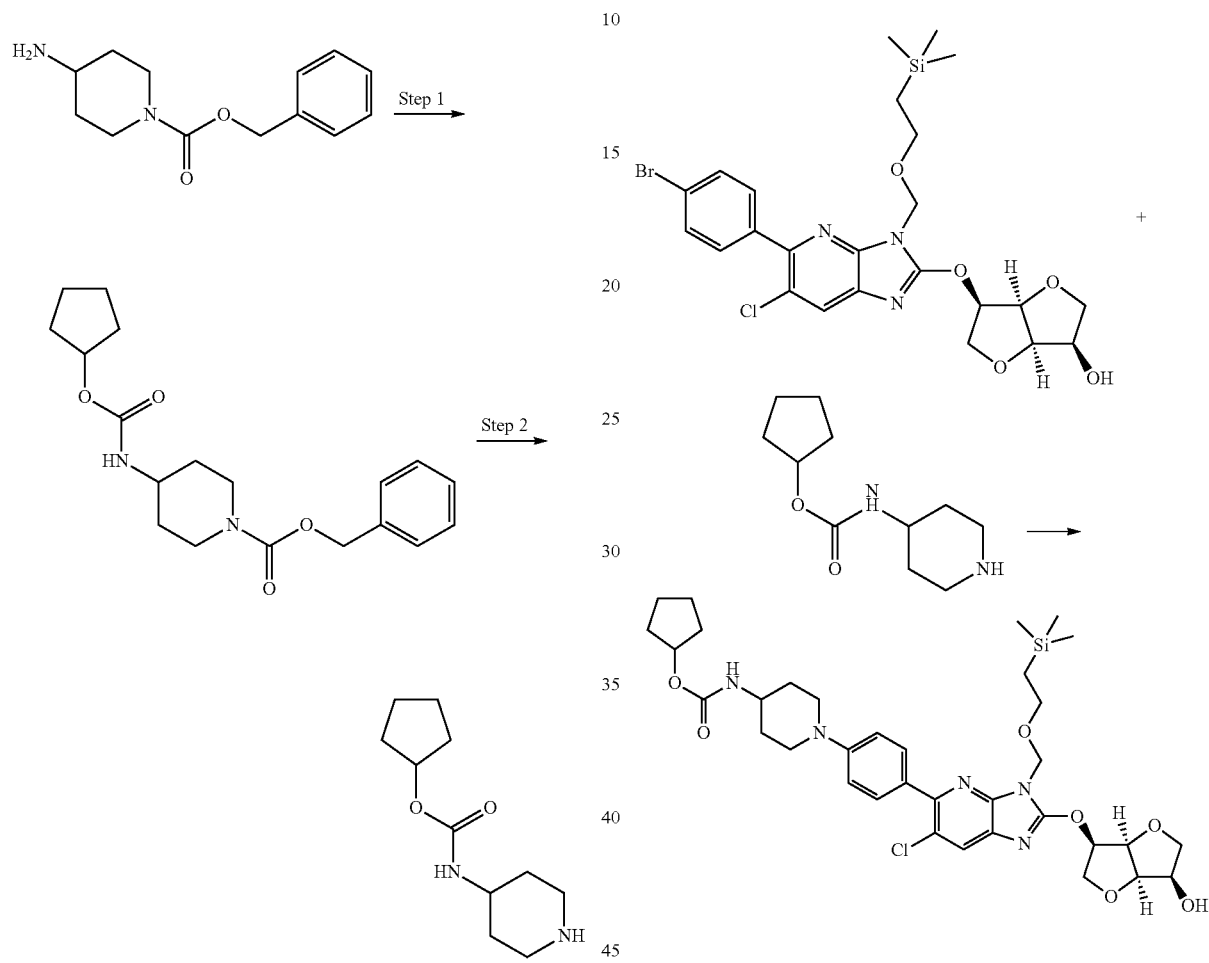

The title compound is prepared from (3R,3aR,6R,6aR)-6-(5-(4-bromophenyl)-6-chloro-3-((2-(trimethylsilyl)ethoxy)methyl)-3H-imidazo[4,5-b]pyridin-2-yloxy)hexahydrofuro[3,2-b]furan-3-ol and cyclopentyl piperidin-4-ylcarbamate following a procedure analogous to that described for Intermediate 23. LC (method 1): $t_R$=1.09 min; Mass spectrum (ESI$^+$): m/z=714 [M+H]$^+$.

Step 1: Benzyl 4-(cyclopentyloxycarbonylamino)piperidine-1-carboxylate

The title compound is prepared from benzyl 4-aminopiperidine-1-carboxylate and cyclopentyl chloroformate following a procedure analogous to that described for Intermediate 26 Step 1. LC (method 1): $t_R$=1.06 min; Mass spectrum (ESI$^+$): m/z=347 [M+H]$^+$.

Step 2: Cyclopentyl piperidin-4-ylcarbamate

The title compound is prepared from benzyl 4-(cyclopentyloxycarbonylamino)piperidine-1-carboxylate following a procedure analogous to that described for Intermediate 22 Step 2.

Intermediate 32

Tetrahydro-2H-pyran-4-yl piperidin-4-ylcarbamate

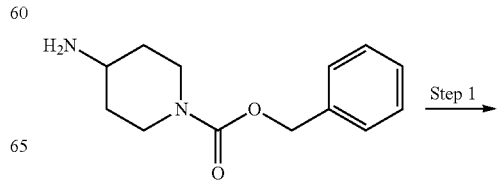

Intermediate 33

Tetrahydro-2H-pyran-4-yl 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-ylcarbamate

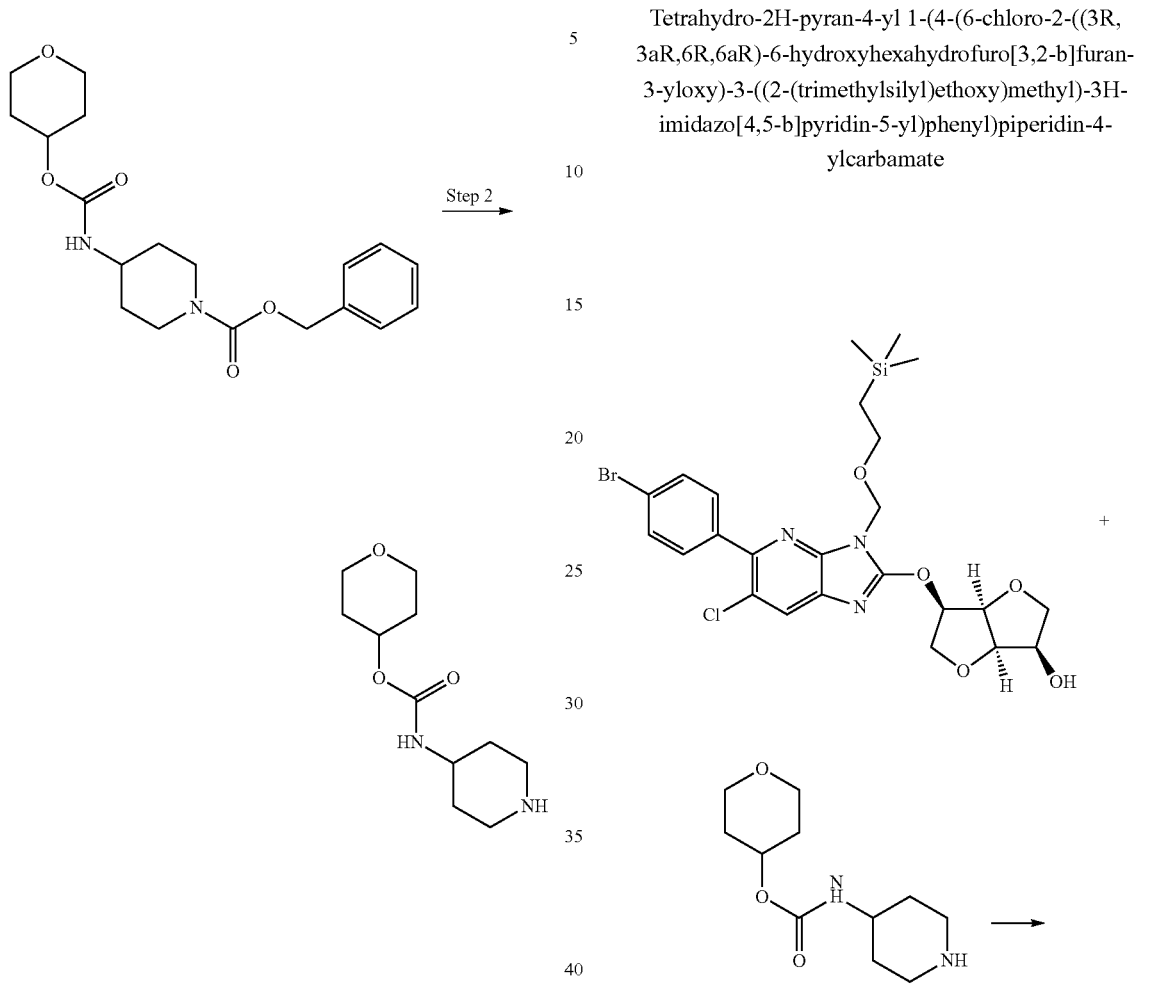

Step 1: Benzyl 4-((tetrahydro-2H-pyran-4-yloxy)carbonylamino)piperidine-1-carboxylate Benzyl 4-aminopiperidine-1-carboxylate (100 mg) is dissolved in toluene (1 mL), treated dropwise with a solution of diphosgene (52 µL) in toluene (1 mL) and stirred for 12 hours at 80° C. Tetrahydro-2H-pyran-4-ol (41 µL) is added and the mixture is heated for 3 hours at 80° C. The mixture is partitioned between ethylacetate and saturated aqueous NH$_4$Cl solution. The organic phase is dried (MgSO$_4$) and concentrated. The residue is purified by HPLC on reversed phase to give the title compound. LC (method 1): $t_R$=0.95 min; Mass spectrum (ESI$^+$): m/z=363 [M+H]$^+$.

Step 2: Tetrahydro-2H-pyran-4-yl piperidin-4-ylcarbamate

The title compound is prepared from benzyl 4-((tetrahydro-2H-pyran-4-yloxy)carbonylamino)piperidine-1-carboxylate following a procedure analogous to that described for Intermediate 22 Step 2.

The title compound is prepared from (3R,3aR,6R,6aR)-6-(5-(4-bromophenyl)-6-chloro-3-((2-(trimethylsilyl)ethoxy)methyl)-3H-imidazo[4,5-b]pyridin-2-yloxy)hexahydrofuro[3,2-b]furan-3-ol and tetrahydro-2H-pyran-4-yl piperidin-4-ylcarbamate following a procedure analogous to that described for Intermediate 23. LC (method 1): $t_R$=0.99 min; Mass spectrum (ESI$^+$): m/z=730 [M+H]$^+$.

Intermediate 34
(trans)-4-(4-(2-(((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanamine
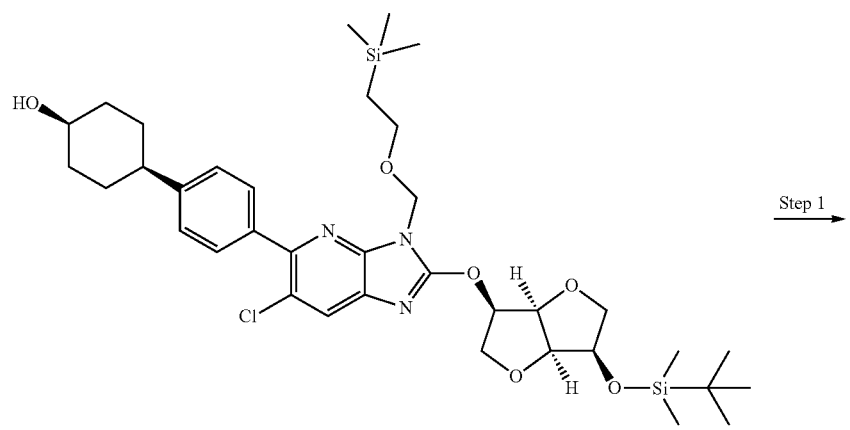
Step 1
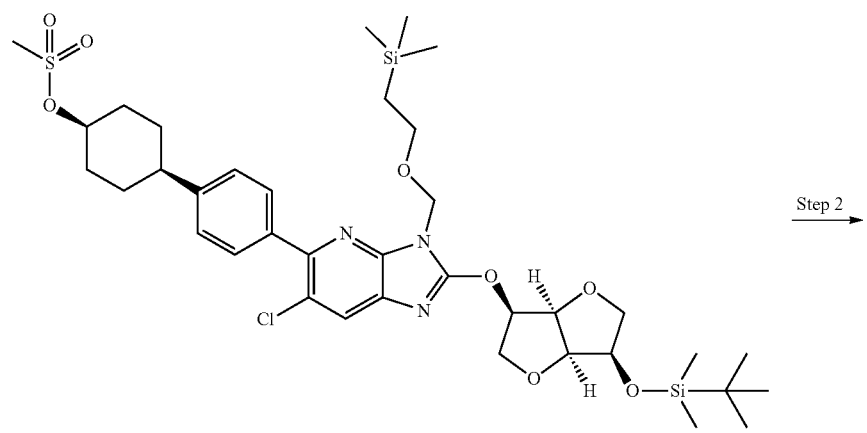
Step 2
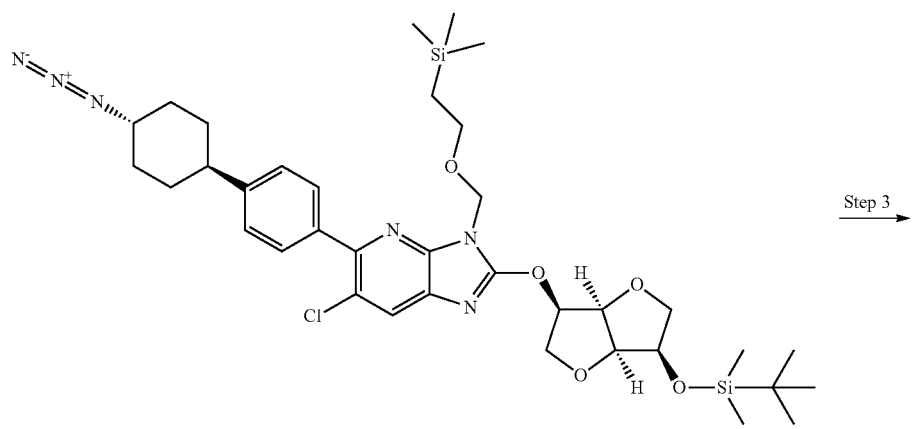
Step 3

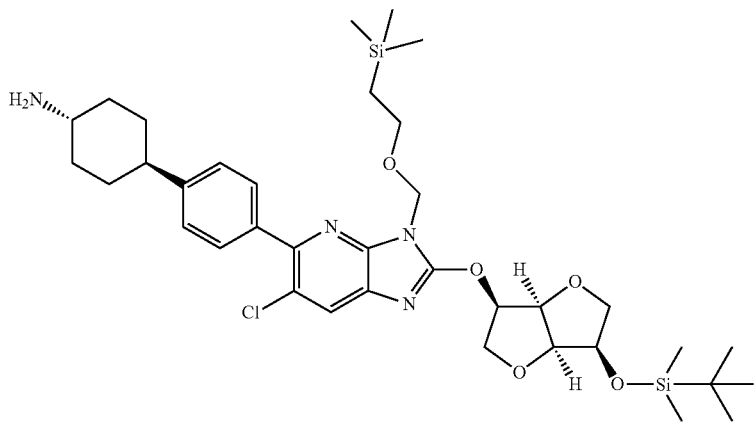

Step 1: (cis)-4-(4-(2-((3R,3aR,6R,6aS)-6-(tert-butyldimethylsilyloxy)hexahydrofuro-[3,2-b]furan-3-yloxy)-6-chloro-3-((2-(trimethylsilyl)ethoxy)methyl)-3H-imidazo[4,5-b]-pyridin-5-yl)phenyl) cyclohexyl methanesulfonate (cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanol (250 mg) and triethylamine (240 µL) are dissolved in dichloromethane (2 mL), treated with methanesulfonyl chloride (40 µL) and stirred for 12 hours at room temperature. The mixture is partitioned between ethylacetate and water. The organic phase is washed with brine, dried (MgSO$_4$) and concentrated to give the title compound, which is used directly in the next step. LC (method 5): t$_R$=1.19 min; Mass spectrum (ESI$^+$): m/z=794 [M+H]$^+$.

Step 2: 5-(4-((trans)-4-Azidocyclohexyl)phenyl)-2-((3R,3aR,6R,6aS)-6-(tert-butyldimethylsilyloxy)hexahydrofuro[3,2-b]furan-3-yloxy)-6-chloro-3-((2-(trimethylsilyl)-ethoxy)methyl)-3H-imidazo[4,5-b]pyridine (cis)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl) cyclohexyl methanesulfonate (295 mg) is dissolved in N,N-dimethylformamide (5 mL), treated with sodium azide (52 mg) and stirred for 12 hours at 80° C. The mixture is partitioned between ethylacetate and saturated aqueous NH$_4$Cl solution. The organic phase is dried (MgSO$_4$) and concentrated. The residue is chromatographed on silica gel (cyclohexane/ethyl acetate 90:10→60:40) to give the title compound. LC (method 5): t$_R$=1.33 min; Mass spectrum (ESI$^+$): m/z=741 [M+H]$^+$.

Step 3: (trans)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl) cyclohexanamine 5-(4-((trans)-4-Azidocyclohexyl)phenyl)-2-((3R,3aR,6R,6aS)-6-(tert-butyldimethyl-silyloxy)hexahydrofuro[3,2-b]furan-3-yloxy)-6-chloro-3-((2-(trimethylsilyl)ethoxy)methyl)-3H-imidazo[4,5-b]pyridine (130 mg) is dissolved in tetrahydrofurane (1 mL), treated with triphenylphosphine (57 mg) and stirred for 24 hours at 40° C. Then water (220 µL) is added and the mixture is stirred for 12 hours at 80° C. The mixture is partitioned between ethylacetate and saturated aqueous NH$_4$Cl solution. The organic phase is dried (MgSO$_4$) and concentrated. The residue is purified by HPLC on reversed phase to give the product, which is partitioned between 1 M aqueous NaOH solution and ethylacetate. The organic phase is washed with brine and dried (MgSO$_4$). The residue is concentrated to give the title compound. LC (method 1): t$_R$=1.24 min; Mass spectrum (ESI$^+$): m/z=715 [M+H]$^+$.

Intermediate 35

Isopropyl (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]-pyridin-5-yl)phenyl)cyclohexylcarbamate

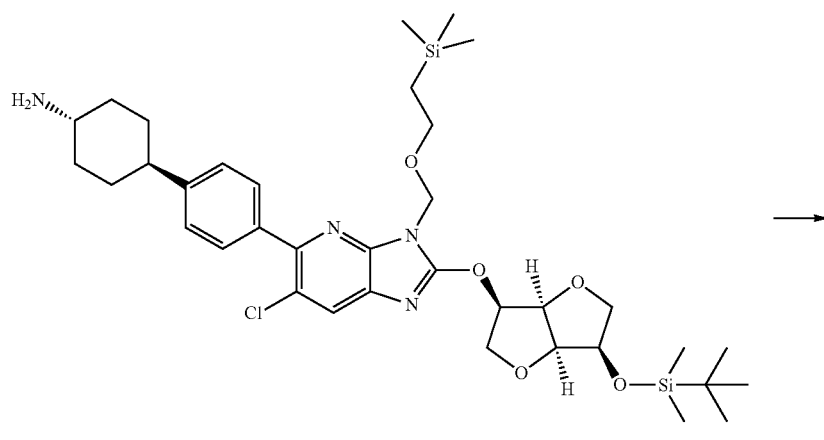

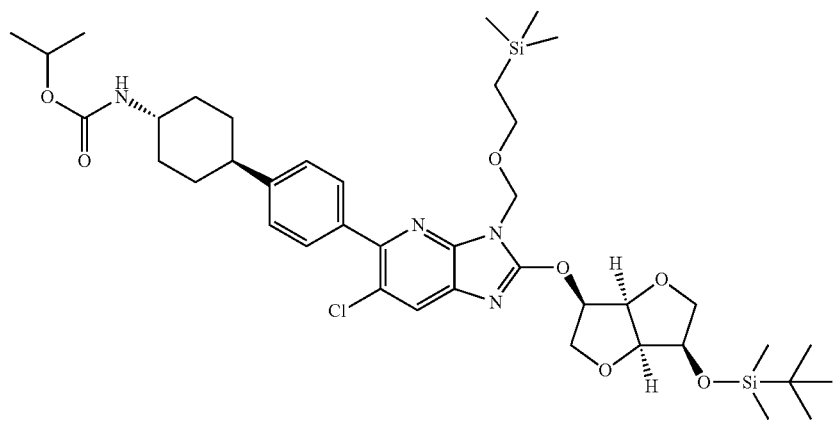

(trans)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanamine (10 mg) and triethylamine (6 μL) are dissolved in dichloromethane (1 mL), treated with isopropyl chloroformate (28 μL, 1 M solution in toluene) and stirred for 12 hours at room temperature. The mixture is partitioned between ethylacetate and saturated aqueous NH$_4$Cl solution. The organic phase is washed with brine, dried (MgSO$_4$) and concentrated to give the title compound, which is used directly in the next step. LC (method 5): t$_R$=1.27 min.

Intermediate 36

Methyl (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate

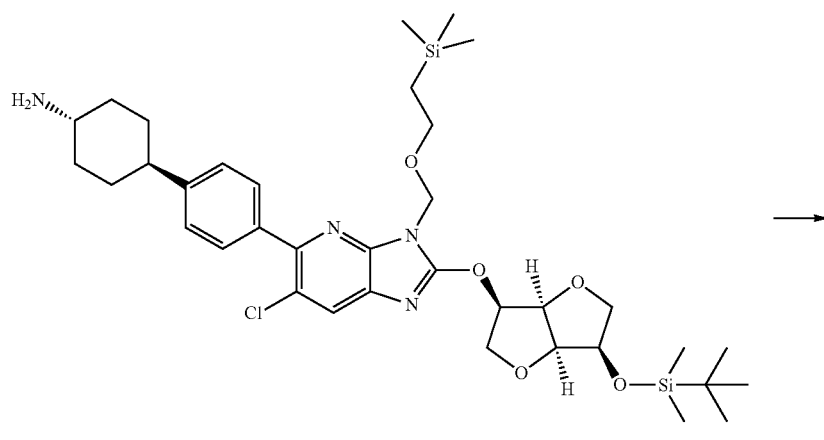

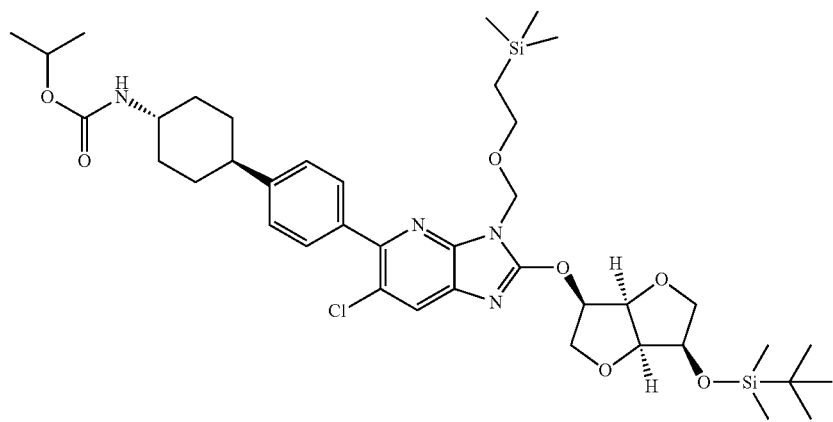

(trans)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanamine (20 mg) and triethylamine (12 μL) are dissolved in dichloromethane (2 mL), treated with methyl chloroformate (4.5 μL) and stirred for 12 hours at room temperature. Triethylamine (12 μL) and methyl chloroformate (4.5 μL) are added and the mixture is stirred for 5 hours at room temperature. The mixture is partitioned between dichloromethane and saturated aqueous $NH_4Cl$ solution. The organic phase is washed with brine, dried ($MgSO_4$) and concentrated to give the title compound, which is directly used in the next step. LC (method 5): $t_R$=1.20 min; Mass spectrum (ESI$^+$): m/z=773 [M+H]$^+$.

Intermediate 37

Cyclopentyl (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate

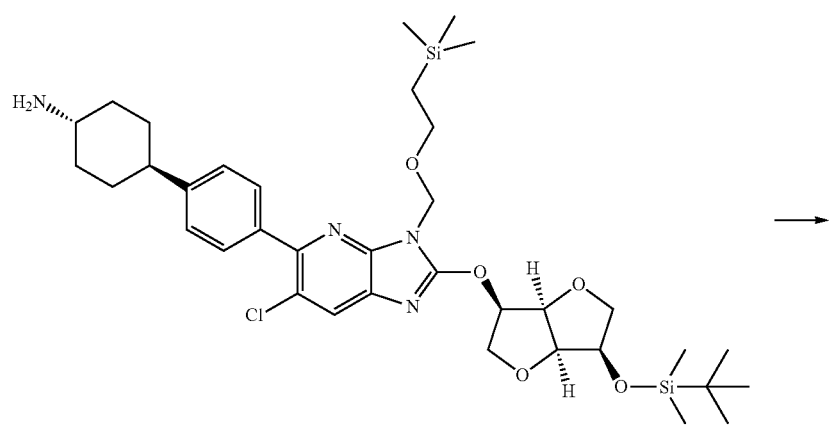

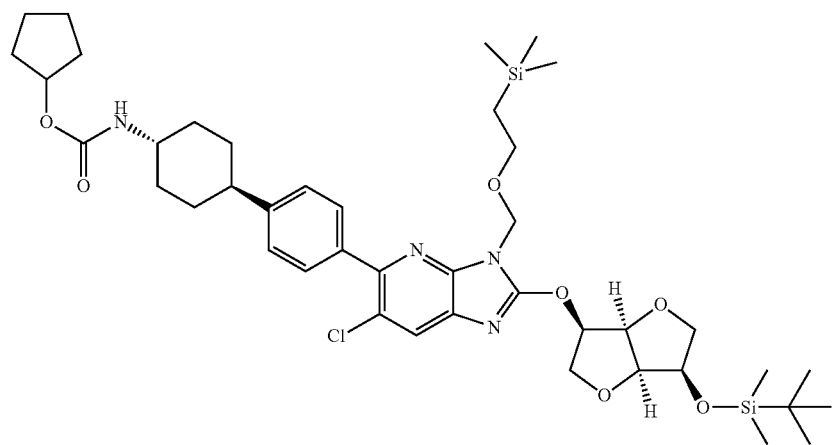

(trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsi-lyl)ethoxy)methyl)-3H-imidazo[4,5-b]pyridin-5-yl)phenyl)cyclohexanamine (20 mg) and triethylamine (12 μL) are dissolved in dichloromethane (2 mL), treated with cyclopentyl chloroformate (7.3 μL) and stirred for 12 hours at room temperature. Triethylamine (12 μL) and cyclopentyl chloroformate (7.3 μL) are added and the mixture is stirred for 5 hours at room temperature. The mixture is partitioned between dichloromethane and saturated aqueous NH$_4$Cl solution. The organic phase is washed with brine, dried (MgSO$_4$) and concentrated to give the title compound, which is directly used in the next step. LC (method 5): t$_R$=1.30 min.

Intermediate 38

Tetrahydro-2H-pyran-4-yl (trans)-4-(4-(2-((3R,3aR, 6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate

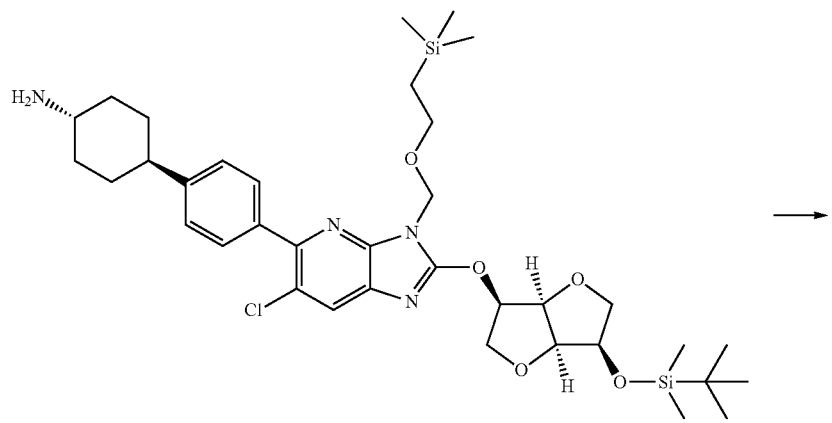

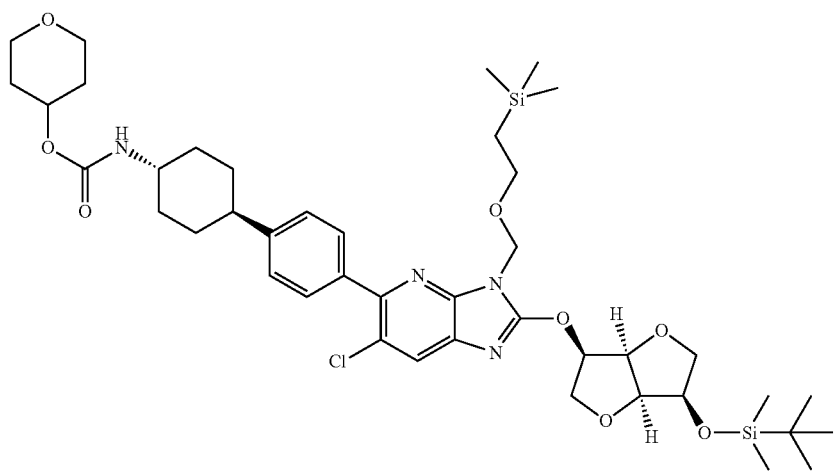

(trans)-4-(4-(2-((3R,3aR,6R,6aS)-6-(tert-Butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexanamine (20 mg) is dissolved in toluene (2 mL), treated dropwise with a solution of diphosgene (3.4 µL) in toluene (1 mL) and stirred for 12 hours at 60° C. Tetrahydro-2H-pyran-4-ol (2.7 µL) is added and the mixture is heated for 12 hours at 60° C. The mixture is partitioned between ethylacetate and saturated aqueous NH$_4$Cl solution. The organic phase is washed with brine, dried (MgSO$_4$) and concentrated to give the title compound. LC (method 5): t$_R$=1.22 min.

Example 1

Ethyl 1-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)piperidin-4-ylcarbamate

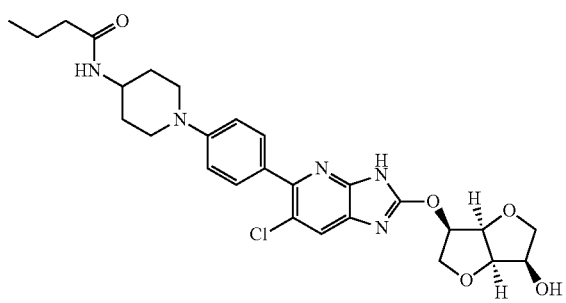 [SMILES: CCCC(=O)NC1CCN(c2ccc(-c3nc4[nH]c(O[C@@H]5CO[C@H]6[C@@H]5OC[C@H]6O)nc4cc3Cl)cc2)CC1]

A mixture of ethyl 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-ylcarbamate (44 mg) and $KHSO_4$ (2 M aqueous solution, 40 μL) in formic acid (3 mL) is stirred for 3 hours at 60° C. After diluting with water and cooling to 0° C. NaOH (10 M aqueous solution) is added until the pH >11. Tetrahydrofurane (3 mL) is added and the mixture is stirred for 1 hour at room temperature. Hydrochloric acid (4 N) is added until pH=6. Then the mixture is partitioned between water and ethylacetate and the organic phase is washed with brine and dried ($MgSO_4$). The solvents are evaporated in vacuo and the residue is purified by HPLC on reversed phase to give the title compound. LC (method 1): $t_R$=0.81 min; Mass spectrum ($ESI^+$): m/z=544 $[M+H]^+$.

Example 2

1-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)piperidin-4-yl dimethylcarbamate

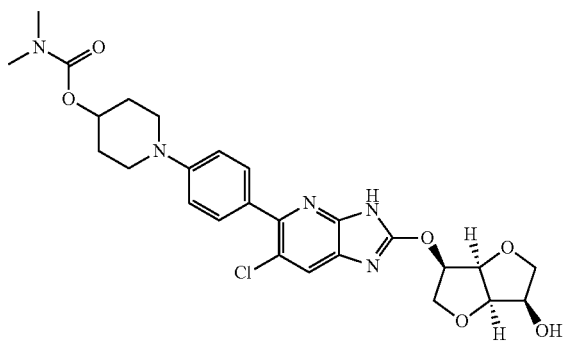 [SMILES: CN(C)C(=O)OC1CCN(c2ccc(-c3nc4[nH]c(O[C@@H]5CO[C@H]6[C@@H]5OC[C@H]6O)nc4cc3Cl)cc2)CC1]

The title compound is prepared from 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-yl dimethylcarbamate following a procedure analogous to that described for Example 1. LC (method 1): $t_R$=0.79 min; Mass spectrum ($ESI^+$): m/z=544 $[M+H]^+$.

Example 3

Cyclopentyl (cis)-4-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)cyclohexylcarbamate

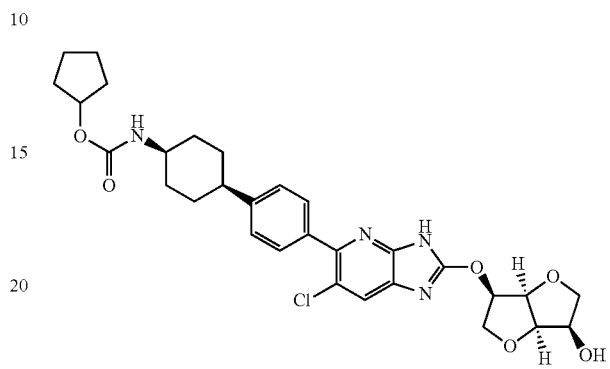

The title compound is prepared from cyclopentyl (cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate following a procedure analogous to that described for Example 1. LC (method 1): $t_R$=1.05 min; Mass spectrum ($ESI^+$): m/z=583 $[M+H]^+$.

Example 4

Isopropyl (cis)-4-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)cyclohexylcarbamate

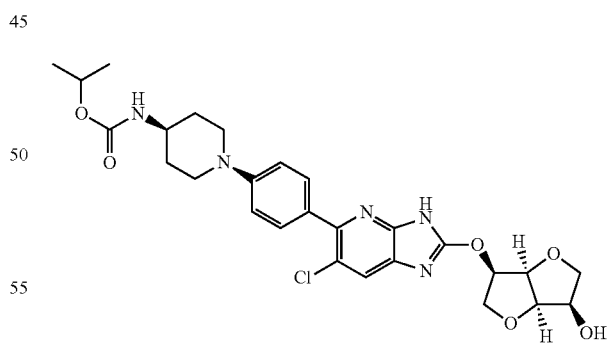

The title compound is prepared from isopropyl (cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate following a procedure analogous to that described for Example 1. LC (method 1): $t_R$=1.00 min; Mass spectrum ($ESI^+$): m/z=557 $[M+H]^+$.

Example 5

Tetrahydro-2H-pyran-4-yl (cis)-4-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)cyclohexylcarbamate

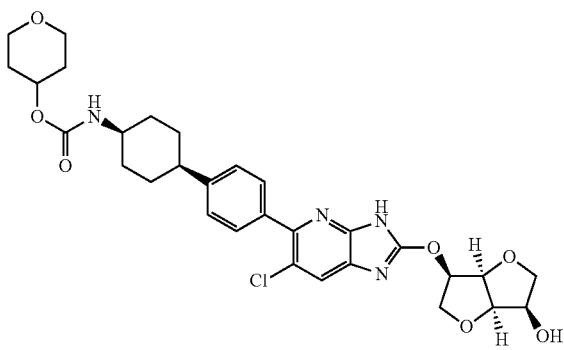 [SMILES: O=C(N[C@H]1CC[C@@H](c2ccc(-c3nc4[nH]c(O[C@@H]5CO[C@H]6[C@@H]5OC[C@H]6O)nc4cc3Cl)cc2)CC1)OC1CCOCC1]

The title compound is prepared from tetrahydro-2H-pyran-4-yl (cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)-cyclohexylcarbamate following a procedure analogous to that described for Example 1. LC (method 1): $t_R$=0.96 min; Mass spectrum (ESI$^+$): m/z=599 [M+H]$^+$.

Example 6

(trans)-4-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)cyclohexyl morpholine-4-carboxylate

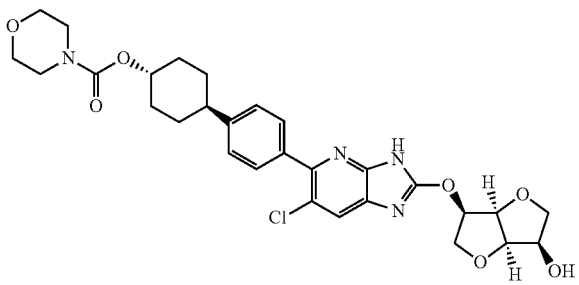 [SMILES: O=C(O[C@H]1CC[C@H](c2ccc(-c3nc4[nH]c(O[C@@H]5CO[C@H]6[C@@H]5OC[C@H]6O)nc4cc3Cl)cc2)CC1)N1CCOCC1]

The title compound is prepared from (trans)-4-(4-(2-((3R,3aR,6R,6aS)-6-(tert-butyldimethylsilyloxy)hexahydrofuro[3,2-b]furan-3-yloxy)-6-chloro-3-((2-(trimethyl-silyl)ethoxy)methyl)-3H-imidazo[4,5-b]pyridin-5-yl)phenyl)cyclohexyl morpholine-4-carboxylate following a procedure analogous to that described for Example 1. LC (method 1): $t_R$=0.98 min; Mass spectrum (ESI$^+$): m/z=585 [M+H]$^+$.

Example 7

(trans)-4-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)cyclohexyl ethylcarbamate

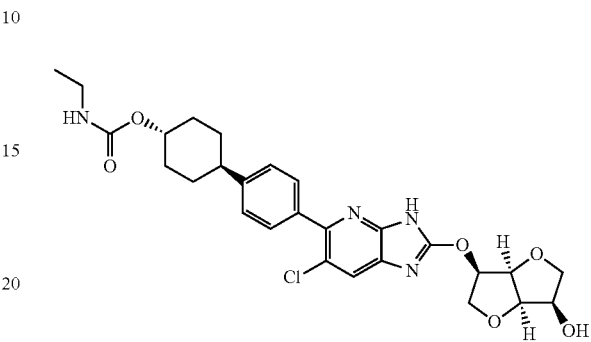

The title compound is prepared from (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl ethylcarbamate following a procedure analogous to that described for Example 1. LC (method 3): $t_R$=0.94 min; Mass spectrum (ESI$^+$): m/z=543 [M+H]$^+$.

Example 8

(trans)-4-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)cyclohexyl isopropylcarbamate

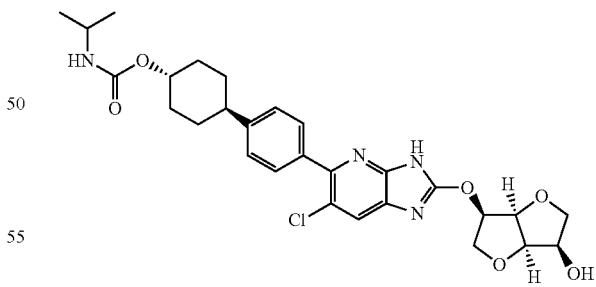

The title compound is prepared from (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl isopropylcarbamate following a procedure analogous to that described for Example 1. LC (method 3): $t_R$=0.98 min; Mass spectrum (ESI$^+$): m/z=557 [M+H]$^+$.

Example 9

(trans)-4-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)cyclohexyl pyrrolidine-1-carboxylate

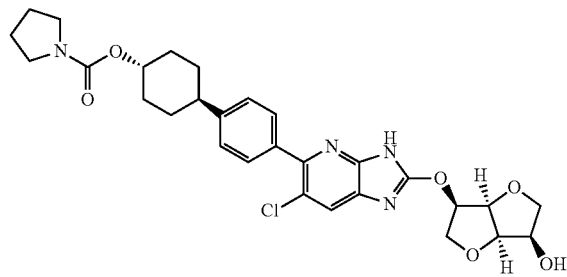 [SMILES: O=C(O[C@H]1CC[C@H](c2ccc(-c3nc4[nH]c(O[C@@H]5CO[C@H]6[C@@H]5OC[C@H]6O)nc4cc3Cl)cc2)CC1)N1CCCC1]

The title compound is prepared from (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl pyrrolidine-1-carboxylate following a procedure analogous to that described for Example 1. LC (method 1): $t_R$=1.04 min; Mass spectrum (ESI$^+$): m/z=569 [M+H]$^+$.

Example 10

(cis)-4-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)cyclohexyl ethylcarbamate

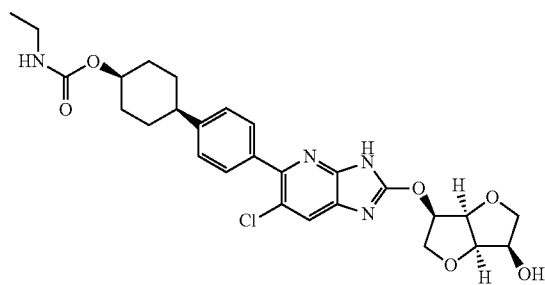 [SMILES: CCNC(=O)O[C@H]1CC[C@@H](c2ccc(-c3nc4[nH]c(O[C@@H]5CO[C@H]6[C@@H]5OC[C@H]6O)nc4cc3Cl)cc2)CC1]

The title compound is prepared from (cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl ethylcarbamate following a procedure analogous to that described for Example 1. LC (method 1): $t_R$=0.95 min; Mass spectrum (ESI$^+$): m/z=543 [M+H]$^+$.

Example 11

(cis)-4-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)cyclohexyl isopropylcarbamate

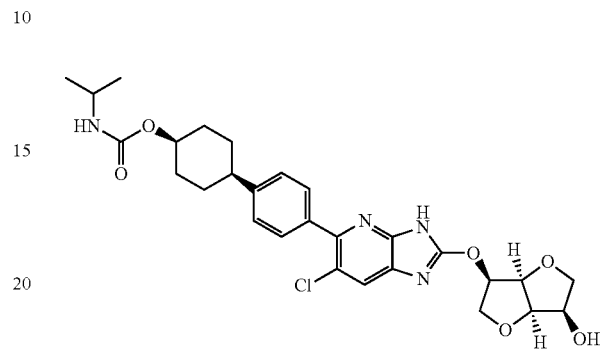

The title compound is prepared from (cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl isopropylcarbamate following a procedure analogous to that described for Example 1. LC (method 1): $t_R$=0.99 min; Mass spectrum (ESI$^+$): m/z=557 [M+H]$^+$.

Example 12

(cis)-4-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)cyclohexyl morpholine-4-carboxylate

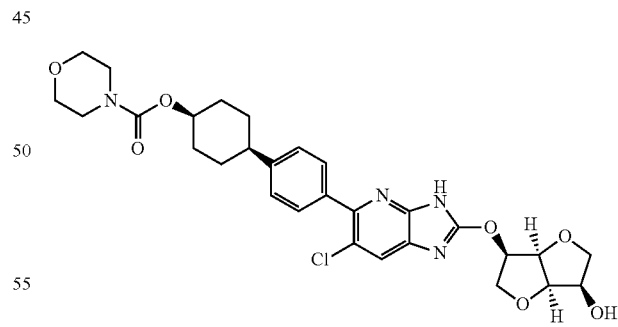

The title compound is prepared from (cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl morpholine-4-carboxylate following a procedure analogous to that described for Example 1. LC (method 1): $t_R$=0.95 min; Mass spectrum (ESI$^+$): m/z=585 [M+H]$^+$.

Example 13

(cis)-4-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)cyclohexyl pyrrolidine-1-carboxylate

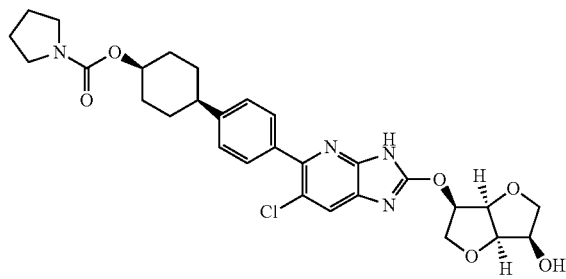 [SMILES: O=C(O[C@H]1CC[C@@H](c2ccc(-c3nc4[nH]c(O[C@@H]5CO[C@H]6[C@@H]5OC[C@H]6O)nc4cc3Cl)cc2)CC1)N1CCCC1]

The title compound is prepared from (cis)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexyl pyrrolidine-1-carboxylate following a procedure analogous to that described for Example 1. LC (method 1): $t_R$=0.99 min; Mass spectrum (ESI$^+$): m/z=569 [M+H]$^+$.

Example 14

1-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)piperidin-4-yl isopropylcarbamate

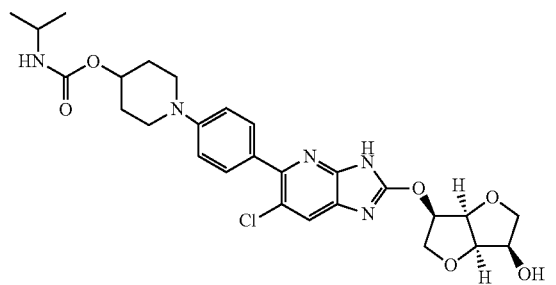 [SMILES: CC(C)NC(=O)OC1CCN(c2ccc(-c3nc4[nH]c(O[C@@H]5CO[C@H]6[C@@H]5OC[C@H]6O)nc4cc3Cl)cc2)CC1]

The title compound is prepared from 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-yl isopropylcarbamate following a procedure analogous to that described for Example 1. LC (method 1): $t_R$=0.82 min; Mass spectrum (ESI$^+$): m/z=558 [M+H]$^+$.

Example 15

1-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)piperidin-4-yl morpholine-4-carboxylate

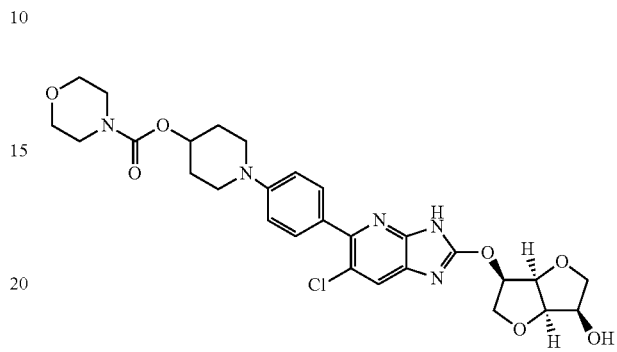

The title compound is prepared from 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-yl morpholine-4-carboxylate following a procedure analogous to that described for Example 1. LC (method 1): $t_R$=0.73 min; Mass spectrum (ESI$^+$): m/z=586 [M+H]$^+$.

Example 16

Isopropyl 1-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)piperidin-4-ylcarbamate

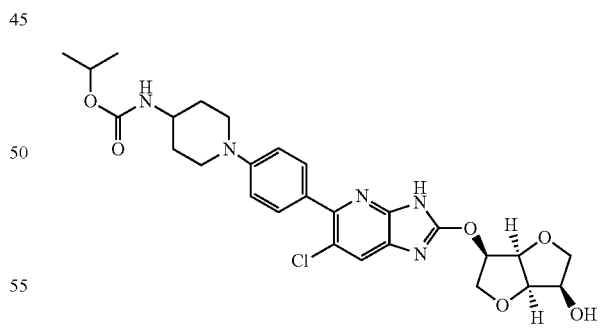

The title compound is prepared from isopropyl 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-ylcarbamate following a procedure analogous to that described for Example 1. LC (method 1): $t_R$=0.81 min; Mass spectrum (ESI$^+$): m/z=558 [M+H]$^+$.

Example 17

Cyclopentyl 1-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)piperidin-4-ylcarbamate

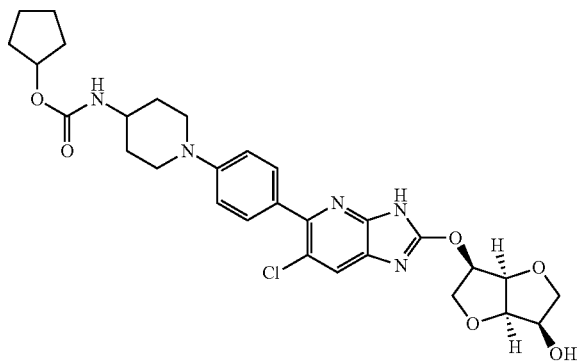 [SMILES: O=C(NC1CCN(c2ccc(-c3nc4[nH]c(O[C@@H]5CO[C@H]6[C@@H]5OC[C@H]6O)nc4cc3Cl)cc2)CC1)OC1CCCC1]

The title compound is prepared from cyclopentyl 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-ylcarbamate following a procedure analogous to that described for Example 1. LC (method 1): $t_R$=0.86 min; Mass spectrum (ESI$^+$): m/z=584 [M+H]$^+$.

Example 18

Tetrahydro-2H-pyran-4-yl 1-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)piperidin-4-ylcarbamate

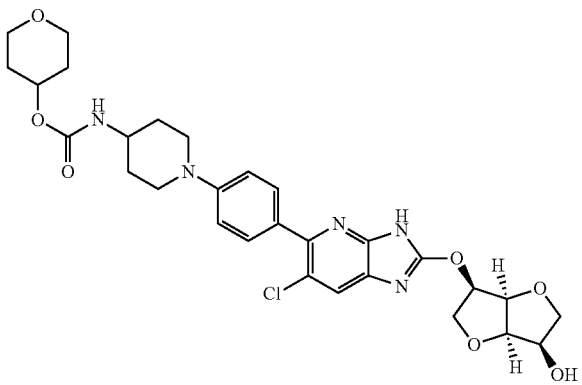 [SMILES: O=C(NC1CCN(c2ccc(-c3nc4[nH]c(O[C@@H]5CO[C@H]6[C@@H]5OC[C@H]6O)nc4cc3Cl)cc2)CC1)OC1CCOCC1]

The title compound is prepared from tetrahydro-2H-pyran-4-yl 1-(4-(6-chloro-2-((3R,3aR,6R,6aR)-6-hydroxyhexahydrofuro[3,2-b]furan-3-yloxy)-3-((2-(trimethylsilyl)ethoxy)methyl)-3H-imidazo[4,5-b]pyridin-5-yl)phenyl)piperidin-4-ylcarbamate following a procedure analogous to that described for Example 1. LC (method 1): $t_R$=0.76 min; Mass spectrum (ESI$^+$): m/z=600 [M+H]$^+$.

Example 19

Isopropyl (trans)-4-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)cyclohexylcarbamate

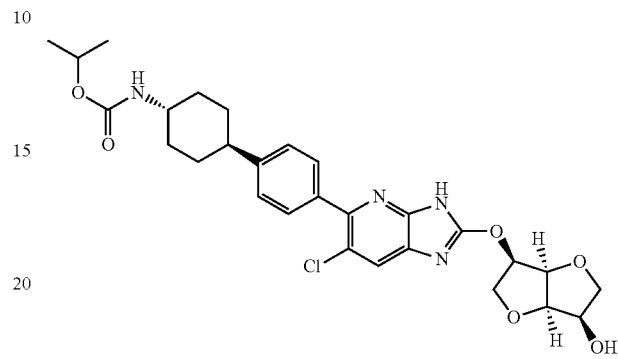

The title compound is prepared from isopropyl (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate following a procedure analogous to that described for Example 1. LC (method 1): $t_R$=1.00 min; Mass spectrum (ESI$^+$): m/z=557 [M+H]$^+$.

Example 20

Cyclopentyl (trans)-4-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)cyclohexylcarbamate

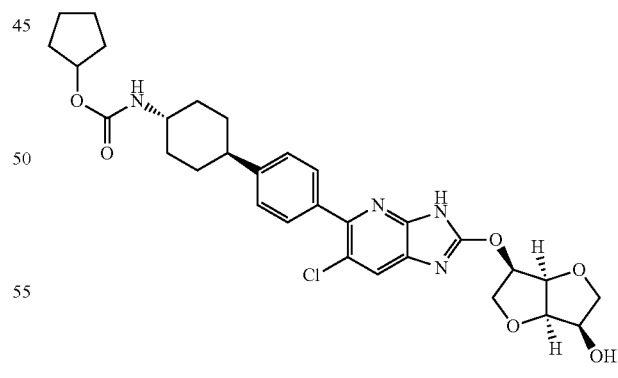

The title compound is prepared from cyclopentyl (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate following a procedure analogous to that described for Example 1. LC (method 1): $t_R$=1.04 min; Mass spectrum (ESI$^+$): m/z=583 [M+H]$^+$.

Example 21

Tetrahydro-2H-pyran-4-yl (trans)-4-(4-(6-chloro-2-((3R,3aR,6R,6aR)-6-hydroxyhexahydrofuro[3,2-b]furan-3-yloxy)-3H-imidazo[4,5-b]pyridin-5-yl)phenyl)cyclohexylcarbamate

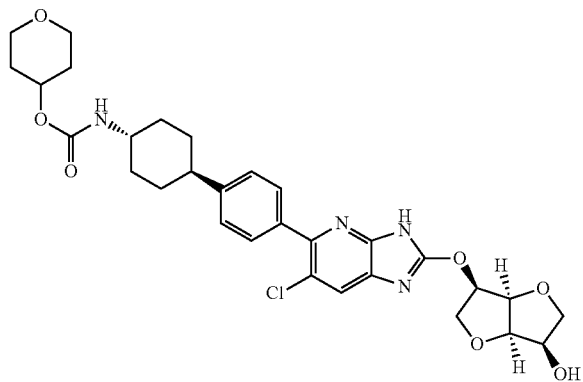 [SMILES: O=C(N[C@H]1CC[C@H](c2ccc(-c3nc4[nH]c(O[C@@H]5CO[C@H]6[C@@H]5OC[C@H]6O)nc4cc3Cl)cc2)CC1)OC1CCOCC1]

The title compound is prepared from tetrahydro-2H-pyran-4-yl (trans)-4-(4-(2-((3R,3aR,6R,6aS)-6-(tert-butyldimethylsilyloxy)hexahydrofuro[3,2-b]furan-3-yloxy)-6-chloro-3-((2-(trimethylsilyl)ethoxy)methyl)-3H-imidazo[4,5-b]pyridin-5-yl)phenyl)cyclohexylcarbamate following a procedure analogous to that described for Example 1. LC (method 1): $t_R$=0.93 min; Mass spectrum (ESI$^+$): m/z=599 [M+H]$^+$.

The invention claimed is:
1. A compound of formula I

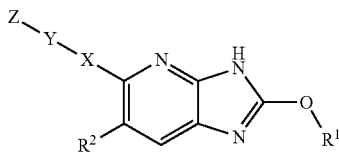

wherein $R^1$ is selected from the group $R^1$-G1 consisting of $C_{3-10}$-cycloalkyl and heterocyclyl, both optionally substituted with 1 to 3 groups independently selected from HO—, NC—, HO$_2$C—, HO$_2$C—H$_2$C—, $C_{1-4}$-alkyl, $C_{1-4}$-alkyl-O—, and HO—$C_{1-4}$-alkyl-,
  wherein heterocyclyl denotes a saturated mono-, bi- or spirocyclic ring system having 5 to 10 ring member atoms of which 1 or 2 not vicinal ring members are O atoms;

$R^2$ is selected from the group $R^2$-G1 consisting of F, Cl, Br, $C_{1-4}$-alkyl, and $C_{1-4}$-alkyl-O—, wherein any alkyl group and subgroup is optionally substituted with 1 or more F atoms;

X is selected from the group X-G1 consisting of an arylene, and a heteroarylene group,
  wherein said arylene and heteroarylene groups are optionally substituted with 1 to 3 groups independently selected from F, Cl, Br, I, NC—, HO—, HO$_2$C—, $C_{1-4}$-alkyl, $C_{1-4}$-alkyl-O—, F$_3$C—, and F$_3$CO—;

Y is selected from the group Y-G1 consisting of a $C_{4-7}$-cycloalkylene, $C_{5-7}$-cycloalkenylene and heterocycloalkylene,
  wherein said cycloalkylene, cycloalkenylene and heterocycloalkylene groups are optionally substituted with 1 to 3 groups independently selected from F, NC—, $C_{1-4}$-alkyl and $C_{1-4}$-alkyl-O—,
  and wherein heterocycloalkylene denotes a 5- to 12-membered bivalent saturated monocyclic or bicyclic fused, bridged or spiro group wherein one ring member is N or NR$^N$ and any other ring members are C atoms,
    wherein R$^N$ is selected from H, $C_{1-4}$-alkyl, $C_{3-7}$-cycloalkyl, $C_{3-7}$-cycloalkyl-CH$_2$—, heterocyclyl, and heterocyclyl-CH$_2$—,
    wherein any alkyl, cycloalkyl and heterocyclyl group or subgroup is optionally substituted with 1 to 3 groups independently selected from $C_{1-3}$-alkyl-O—, ($C_{1-3}$-alkyl)$_2$-N—, HO$_2$C—, $C_{1-3}$-alkyl-C(O)—, and $C_{1-3}$-alkyl-S(O)$_2$—;

Z is selected from the group Z-G1 consisting of (R$^N$R$^{N'}$)N—C(O)—O— and R$^O$O—C(O)—N(R$^{N''}$)—,
  wherein R$^N$ and R$^{N'}$ independently are selected from H, $C_{1-4}$-alkyl, $C_{3-7}$-cycloalkyl, $C_{3-7}$-cycloalkyl-CH$_2$—, heterocyclyl, and heterocyclyl-CH$_2$—, with the proviso that only one of R$^N$ and R$^{N'}$denotes H,
    wherein any alkyl, cycloalkyl and heterocyclyl group or subgroup is optionally substituted with 1 to 3 groups independently selected from $C_{1-3}$-alkyl-O—, ($C_{1-3}$-alkyl)$_2$—N—, HO$_2$C—, $C_{1-3}$-alkyl-C(O)—, and $C_{1-3}$-alkyl-S(O)$_2$—, or
  wherein the group R$^N$(R$^{N'}$)N forms a heterocyclyl group linked via the N atom to the —C(O)—O— moiety,
    wherein said heterocyclyl group is optionally substituted with a group selected from F, H$_3$C— and CN,
  wherein R$^O$ is selected from $C_{2-4}$-alkyl, $C_{3-7}$-cycloalkyl, $C_{3-7}$-cycloalkyl-CH$_2$—, heterocyclyl, and heterocyclyl-CH$_2$—,
    wherein any alkyl, cycloalkyl and heterocyclyl group or subgroup is optionally substituted with 1 to 3 groups independently selected from $C_{1-3}$-alkyl-O—, ($C_{1-3}$-alkyl)$_2$N—, HO$_2$C—, $C_{1-3}$-alkyl-C(O)—, and $C_{1-3}$-alkyl-S(O)$_2$—, and
  wherein R$^{N''}$ is selected from H, H$_3$C—, H$_5$C$_2$—, and cyclopropyl;

wherein any heterocyclyl group mentioned hereinbefore, if not specified otherwise, denotes a saturated or partially unsaturated monocyclic or bicyclic fused, bridged or spiro group having 5 to 12 ring member atoms of which 4 to 11 ring members are C atoms and 1 to 3 ring members are heteroatoms selected from N and NR$^{N'''}$, or 1 or 2 ring members are heteroatoms selected from N and NR$^{N'''}$ and 1 ring member is selected from O and S(=O)$_r$ with r =0, 1 or 2, or 1 ring member is N and 2 ring members are independently selected from O and S(=O)$_r$ with r=0, 1 or 2, with the proviso that no O—O, S—S or S—O bond is formed,
  wherein 1 CH$_2$ ring member attached to a ring member N atom is optionally replaced by a —C(=O)— group,
  and wherein R$^{N'''}$ is selected from H, H$_3$C—, H$_5$C$_2$—, cyclopropyl, H$_3$C—C(O)—, and H$_3$C—S(O)$_2$—;

wherein any arylene group mentioned hereinbefore denotes a bivalent aryl group;
wherein any heteroarylene group mentioned hereinbefore denotes a bivalent heteroaryl group;
wherein any cycloalkylene group mentioned hereinbefore denotes a bivalent cycloalkyl group;

wherein any cycloalkenylene group mentioned hereinbefore denotes a bivalent cycloalkenyl group;

wherein any aryl group mentioned hereinbefore, if not specified otherwise, denotes a carbocyclic aromatic monocyclic group containing 6 carbon atoms which may be further fused to a second 5- or 6-membered carbocyclic group which may be aromatic, saturated or unsaturated;

wherein any heteroaryl group mentioned hereinbefore, if not specified otherwise, denotes tetrazolyl,
  a 5-membered heteroaromatic ring containing
    1 ring member selected from $NR^{N''}$, O and S, or
    1 N and 1 ring member selected from $NR^{N''}$, O and S, or
    1 $NR^{N''}$, O or S and 2 N,
      wherein $R^{N''}$ is defined as mentioned hereinbefore, or
  a 6-membered heteroaromatic ring containing 1 to 3 N atoms; and wherein in any definition mentioned hereinbefore and if not specified otherwise, any alkyl group or sub-group may be straight-chained or branched, or a salt thereof.

2. A compound according to claim 1, wherein
$R^1$ is selected from is selected from the group consisting of

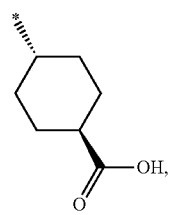

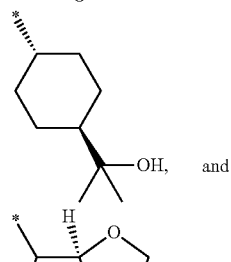

$R^2$ is selected from the group consisting of F, Cl, $H_3C$—;
Y is selected from the group consisting of cyclobutylene, cyclopentylene, cyclohexylene, cyclohexenylene, azetidinylene, pyrrolidinylene, piperidinylene,

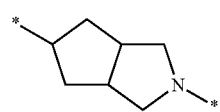

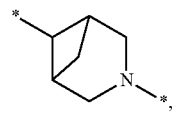

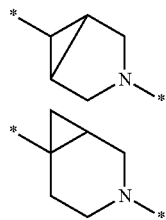

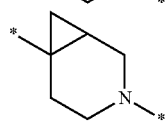

wherein any group containing an N atom as ring member is linked via the N-atom to group X, and
wherein said cyclobutylene, cyclopentylene, cyclohexylene, cyclohexenylene, azetidinylene, pyrrolidinylene, and piperidinylene groups are optionally substituted with $H_3C$—; and Z is $(R^N R^{N'})N$—C(O)—O—,
  wherein $R^N$ and $R^{N'}$, independently are selected from H, $H_3C$—, $H_5C_2$—, $H_3C$—$(CH_2)_2$—, $(H_3C)_2CH$—, $H_3C$—$(CH_2)_3$—, $(H_3C)_2CH$—$CH_2$—, $(H_3C)_3C$—, $H_3CO$—$(CH_2)_2$—, $(H_3C)_2N$—$(CH_2)_2$—, cyclopropyl, cyclobutyl, cyclopentyl, cyclohexyl, tetrahydrofuranyl, tetrahydropyranyl, pyrrolidinyl, and piperidinyl, with the proviso that only one of $R^N$ and $R^{N'}$ denotes H
    wherein any cyclobutyl, cyclopentyl and cyclohexyl group is optionally substituted with 1 or 2 groups independently selected from $H_3C$—, $H_3C$—O—, and $(H_3C)_2N$—, and
    wherein any pyrrolidinyl and piperidinyl group is optionally substituted with $H_3C$—, $H_3C$—C(O)—, or $H_3C$—$S(O)_2$—, or
  wherein the group $R^N(R^{N'})N$ forms an azetidinyl-, pyrrolidinyl-, or piperidinyl-, morpholinyl-group,
    wherein said azetidinyl-, pyrrolidinyl-, or piperidinyl-groups are optionally substituted with $H_3C$—, $H_5C_2$—, cyclopropyl, $H_3C$—C(O)—, or $H_3C$—S$(O)_2$—;

or a salt thereof.

3. A compound according to claim 1, wherein
$R^1$ is selected from is selected from the group consisting of

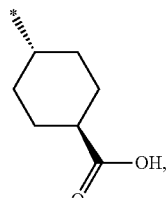

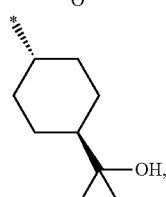

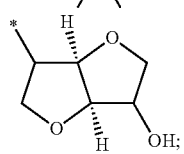

$R^2$ is Cl;
X is selected from the group consisting of phenylene and pyridinylene, bound via para positions and optionally substituted with F or $H_3C$—;

Y is selected from the group consisting of cyclobutylene, cyclopentylene, cyclohexylene,

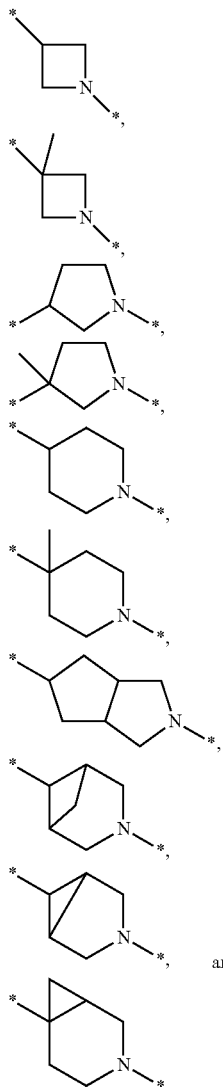

wherein any group containing an N atom as ring member is linked via the N-atom to group X; and Z is $(R^N R^{N'})N-C(O)-O-$,
  wherein $R^N$ and $R^{N'}$ independently are selected from H, $H_3C-$, $H_5C_2-$ and $(H_3C)_2CH-$,
  with the proviso that only one of $R^N$ and $R^{N'}$ denotes H, or
  wherein the group $R^N(R^{N'})N$ altogether is selected from

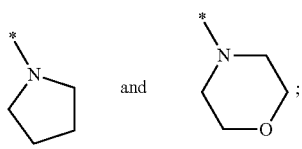 [SMILES: *N1CCCC1 ; *N1CCOCC1]

or a salt thereof.

4. A compound according to claim 1, wherein
Z is $R^O O-C(O)-N(R^{N''})-$, wherein $R^O$ and $R^{N''}$ are defined as in claim 1;
or a salt thereof.

5. A compound according to claim 1, wherein
$R^1$ is selected from is selected from the group consisting of

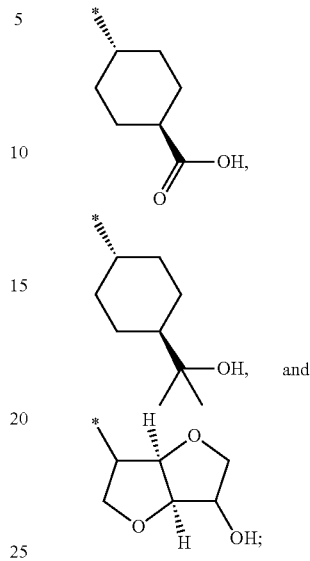

$R^2$ is selected from the group consisting of F, Cl, $H_3C-$;
Y is selected from the group consisting of cyclobutylene, cyclopentylene, cyclohexylene, cyclohexenylene, azetidinylene, pyrrolidinylene, piperidinylene,

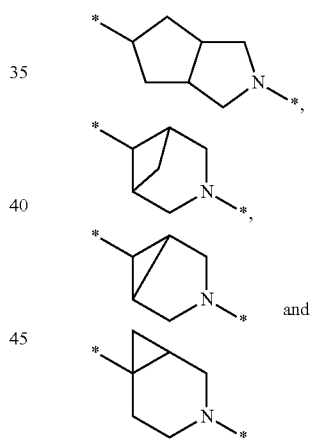

wherein any group containing an N atom as ring member is linked via the N-atom to group X, and wherein said cyclobutylene, cyclopentylene, cyclohexylene, cyclohexenylene, azetidinylene, pyrrolidinylene, and piperidinylene groups are optionally substituted and Z is $R^O O-C(O)-N(R^{N''})-$,
  wherein $R^O$ is selected from $H_5C_2-$, $H_3C-(CH_2)_2-$, $(H_3C)_2CH-$, $H_3C-(CH_2)_3-$, $(H_3C)_2CH-CH_2-$, $(H_3C)_3C-$, $H_3CO-(CH_2)_2-$, $(H_3C)_2N-(CH_2)_2-$, cyclopropyl, cyclobutyl, cyclopentyl, cyclohexyl, tetrahydrofuranyl, tetrahydropyranyl, pyrrolidinyl, and piperidinyl,
  wherein any cyclobutyl, cyclopentyl and cyclohexyl group is optionally substituted with 1 or 2 groups independently selected from $H_3C-$, $H_3C-O-$, and $(H_3C)_2N-$, and wherein any pyrrolidinyl and piperidinyl group is optionally substituted with H₃C—, H₃C—C(O)—, or H₃C—S(O)₂—, and
wherein $R^{N''}$ is selected from H, and H₃C—;
or a salt thereof.

6. A compound according to claim 1, wherein
$R^1$ is selected from is selected from the group consisting of

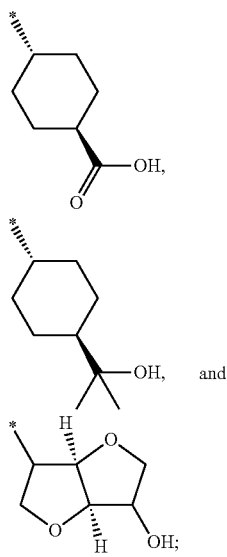

$R^2$ is Cl;
X is selected from the group consisting of phenylene and pyridinylene, bound via para positions and optionally substituted with F or H₃C—;
Y is selected from the group consisting of cyclobutylene, cyclopentylene, cyclohexylene,

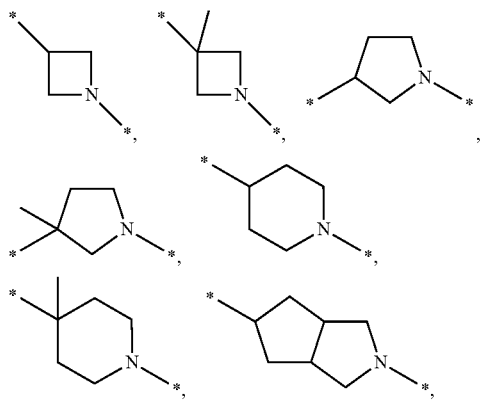

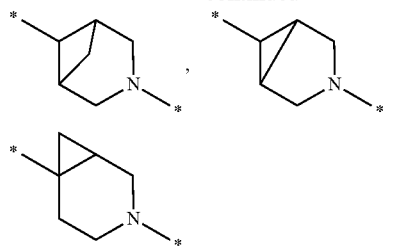

wherein any group containing an N atom as ring member is linked via the N-atom to group X; and and
Z is $R^O$O—C(O)—N(H)—,
wherein $R^O$ is selected from H₅C₂—, (H₃C)₂CH—, cyclopentyl and

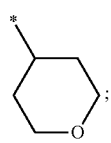

or a salt thereof.

7. A pharmaceutically acceptable salt of a compound according to claim 1.

8. A pharmaceutical composition comprising one or more compounds according to claim 1 or one or more pharmaceutically acceptable salts thereof, optionally together with one or more inert carriers and/or diluents.

9. A method for treating type 2 diabetes mellitus, and conditions associated with the disease, selected from a group consisting of insulin resistance, obesity, cardiovascular disease and dyslipidemia, comprising administering an effective amount of a compound of claim 1 or a pharmaceutically acceptable salt thereof, to a patient in need thereof.

10. A pharmaceutical composition comprising one or more compounds according to claim 1 or one or more pharmaceutically acceptable salts thereof and one or more additional therapeutic agents, optionally together with one or more inert carriers and/or diluents.

11. A pharmaceutical composition according to claim 10 wherein one additional therapeutic agent is selected from the group consisting of antidiabetic agents, agents for the treatment of overweight and/or obesity and agents for the treatment of high blood pressure, heart failure and/or atherosclerosis.

* * * * *